United States Patent
Witschel et al.

(10) Patent No.: US 10,221,137 B2
(45) Date of Patent: Mar. 5, 2019

(54) HERBICIDAL PHENYLPYRIDINES

(71) Applicant: BASF SE, Ludwigshafen (DE)

(72) Inventors: Matthias Witschel, Bad Duerkheim (DE); Tobias Seiser, Mannheim (DE); Manuel Johannes, Duesseldorf (DE); Dario Massa, Mannheim (DE); Trevor William Newton, Neustadt (DE); Richard Evans, Raleigh, NC (US); Raphael Aponte, Ludwigshafen (DE)

(73) Assignee: BASF SE, Ludwighsafen (DE)

( * ) Notice: Subject to any disclaimer, the term of this patent is extended or adjusted under 35 U.S.C. 154(b) by 0 days.

(21) Appl. No.: 15/546,446

(22) PCT Filed: Jan. 19, 2016

(86) PCT No.: PCT/EP2016/050946
§ 371 (c)(1),
(2) Date: Jul. 26, 2017

(87) PCT Pub. No.: WO2016/120116
PCT Pub. Date: Aug. 4, 2016

(65) Prior Publication Data
US 2018/0016234 A1    Jan. 18, 2018

(30) Foreign Application Priority Data

Jan. 29, 2015 (EP) .................... 15152970

(51) Int. Cl.
| | | |
|---|---|---|
| *A01N 25/02* | (2006.01) |
| *A01N 25/04* | (2006.01) |
| *A01N 25/08* | (2006.01) |
| *A01N 43/40* | (2006.01) |
| *A01N 43/44* | (2006.01) |
| *A01N 43/84* | (2006.01) |
| *C07D 213/61* | (2006.01) |
| *C07D 401/12* | (2006.01) |
| *C07D 405/12* | (2006.01) |
| *C07D 413/12* | (2006.01) |
| *C07D 417/12* | (2006.01) |
| *A01N 43/14* | (2006.01) |

(52) U.S. Cl.
CPC .......... *C07D 213/61* (2013.01); *A01N 43/14* (2013.01); *A01N 43/44* (2013.01); *A01N 43/84* (2013.01); *C07D 401/12* (2013.01); *C07D 405/12* (2013.01); *C07D 413/12* (2013.01); *C07D 417/12* (2013.01); *A01N 25/02* (2013.01); *A01N 25/04* (2013.01); *A01N 25/08* (2013.01)

(58) Field of Classification Search
CPC .. C07D 213/61; C07D 401/12; C07D 405/12; C07D 413/12; C07D 417/12; A01N 43/40; A01N 43/44; A01N 43/84; A01N 25/02; A01N 25/04; A01N 25/08
See application file for complete search history.

(56) References Cited

U.S. PATENT DOCUMENTS

| | | |
|---|---|---|
| 5,783,522 A | 7/1998 | Schaefer et al. |
| 6,165,941 A | 12/2000 | Schaefer et al. |
| 6,420,314 B1 | 7/2002 | Hamprecht et al. |

FOREIGN PATENT DOCUMENTS

| | | |
|---|---|---|
| WO | WO 95/02580 | 1/1995 |
| WO | WO 97/06143 | 2/1997 |
| WO | WO 98/54137 | 12/1998 |

OTHER PUBLICATIONS

International Search Report dated Feb. 17, 2016, prepared in International Application No. PCT/EP2016/050946.
International Preliminary Report on Patentability dated Aug. 1, 2017, prepared in International Application No. PCT/EP2016/050946.

*Primary Examiner* — John Pak
*Assistant Examiner* — Nathan W Schlientz
(74) *Attorney, Agent, or Firm* — Brinks Gilson & Lione

(57) ABSTRACT

The present invention relates to phenylpyridines of formula (I)

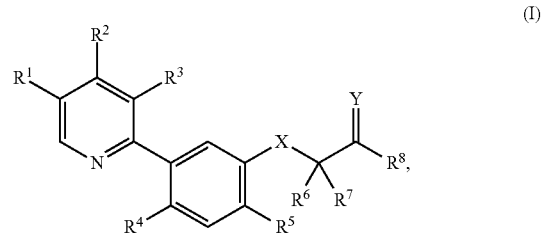

wherein the variables are defined according to the description, processes and intermediates for preparing the phenylpyridines of the formula (I), compositions comprising them and their use as herbicides, i.e. for controlling harmful plants, and also a method for controlling unwanted vegetation which comprises allowing a herbicidal effective amount of at least one phenylpyridine of the formula (I) to act on plants, their seed and/or their habitat.

19 Claims, No Drawings

HERBICIDAL PHENYLPYRIDINES

This application is a National Stage application of International Application No. PCT/EP2016/050946, filed Jan. 19, 2016. This application also claims priority under 35 U.S.C. § 119 to European Patent Application No. 15152970.8, filed Jan. 29, 2015.

The present invention relates to phenylpyridines of the general formula (I) defined below and to their use as herbicides. Moreover, the invention relates to compositions for crop protection and to a method for controlling unwanted vegetation.

WO 97/06143 describes structurally similar compounds for which herbicidal action is stated, which differ from the phenylpyridines according to the present invention that in the substituent in meta-position to the pyridine moiety is a (thio)ether, whereas the compounds according to the invention are substituted in the same position by a (thio)acetal moiety.

However, the herbicidal properties of these known compounds with regard to the harmful plants are not always entirely satisfactory.

It is therefore an object of the present invention to provide phenylpyridines of formula (I) having improved herbicidal action. To be provided are in particular phenylpyridines of formula (I) which have high herbicidal activity, in particular even at low application rates, and which are sufficiently compatible with crop plants for commercial utilization.

These and further objects are achieved by phenylpyridines of formula (I) as defined below, and by their agriculturally suitable salts.

Accordingly, the present invention provides phenylpyridines of formula (I)

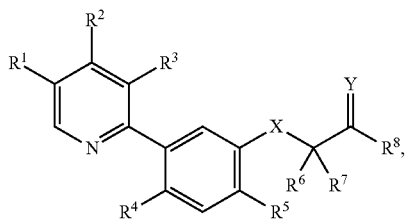

(I)

wherein the variables have the following meanings:
$R^1$ halogen, $C_1$-$C_4$-haloalkyl or $SO_2CH_3$;
$R^2$ H, $CH_3$ or $NH_2$;
$R^3$ halogen;
$R^4$ H or halogen;
$R^5$ halogen or CN;
$R^6$ H or $CH_3$;
$R^7$ $C_1$-$C_6$-alkoxy, $C_1$-$C_6$-haloalkoxy, $C_3$-$C_6$-alkenyloxy, $C_3$-$C_6$-alkynyloxy, $C_1$-$C_6$-alkylthio, $C_1$-$C_6$-haloalkylthio, $C_3$-$C_6$-alkenylthio or $C_3$-$C_6$-alkynylthio;
preferably $C_1$-$C_6$-alkoxy, $C_1$-$C_6$-haloalkoxy, $C_3$-$C_6$-alkenyloxy, $C_3$-$C_6$-alkynyloxy;
$R^8$ $OR^9$, $SR^9$, $NR^{10}R^{11}$, $NR^9S(O)R^{10}$, $NR^9S(O)_2R^{10}$, $NR^9S(O)NR^{10}R^{11}$, or $NR^9S(O)_2NR^{19}R^{11}$,
wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
—N=$CR^{12}R^{13}$, wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6-membered heteroaryl,
wherein each cycloalkyl, heterocyclyl, phenyl or heteroaryl ring can be substituted by one to four substituents selected from $R^{14}$ or a 3- to 7-membered carbocyclus,
which carbocyclus optionally has in addition to carbon atoms one or two ring members selected from the group consisting of —N($R^{12}$)—, —N=N—, —C(=O)—, —O— and —S—, and
which carbocyclus is optionally substituted with one to four substituents selected from $R^{14}$;
wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
$R^{10}$, $R^{11}$ independently of one another are $R^9$, or together form a 3- to 7-membered carbocyclus, which carbocyclus optionally has in addition to carbon atoms one or two ring members selected from the group consisting of —N($R^{12}$)—, —N=N—, —C(=O)—, —O— and —S—, and which carbocyclus is optionally substituted with one to four substituents selected from $R^{14}$;
X P or S; and
Y P or S;
including their agriculturally acceptable salts.

The present invention also provides agrochemical compositions comprising at least one phenylpyridine of formula (I) and auxiliaries customary for formulating crop protection agents.

The present invention also provides herbicidal compositions comprising at least one phenylpyridine of formula (I) (component A) and at least one further compound selected from the herbicidal compounds B (component B) and safeners C (component C).

The present invention also provides the use of phenylpyridines of formula (I) as herbicides, i.e. for controlling harmful plants.

The present invention furthermore provides a method for controlling unwanted vegetation where an herbicidal effective amount of at least one phenylpyridine of formula (I) is allowed to act on plants, their seeds and/or their habitat. Application can be done before, during and/or after, preferably during and/or after, the emergence of the undesirable plants.

Moreover, the invention relates to processes and intermediates for preparing phenylpyridines of formula (I).

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the phenylpyridines of formula (I), the herbicidal compounds B and/or the safeners C as described herein are capable of forming geometrical isomers, for example E/Z isomers, it is possible to use both, the pure isomers and mixtures thereof, in the compositions according to the invention.

If the phenylpyridines of formula (I), the herbicidal compounds B and/or the safeners C as described herein have one or more centres of chirality and, as a consequence, are present as enantiomers or diastereomers, it is possible to use both, the pure enantiomers and diastereomers and their mixtures, in the compositions according to the invention.

If the phenylpyridines of formula (I), the herbicidal compounds B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Herbicidal compounds B and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl) methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The organic moieties mentioned in the definition of the variables $R^1$ to $R^{14}$, are—like the term halogen—collective terms for individual enumerations of the individual group members. The term halogen denotes in each case fluorine, chlorine, bromine or iodine. All hydrocarbon chains, e.g. all alkyl, alkenyl, alkynyl, alkoxy chains, can be straight-chain or branched, the prefix $C_n$-$C_m$ denoting in each case the possible number of carbon atoms in the group.

Examples of such meanings are:

$C_1$-$C_4$-alkyl and also the $C_1$-$C_4$-alkyl moieties of phenyl-$C_1$-$C_4$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl, $C_3$-$C_6$-cycloalkyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl and also the $C_1$-$C_6$-haloalkyl moieties of $C_1$-$C_6$-haloalkylthio: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-alkenyl and also the $C_3$-$C_6$-alkenyl moieties of $C_3$-$C_6$-alkenyloxy, $C_3$-$C_6$-alkenylthio, $C_3$-$C_6$-alkenyloxy-$C_1$-$C_6$-alkyl, $C_3$-$C_6$-alkenyloxy-$C_1$-$C_6$-alkoxy-$C_1$-$C_6$-alkyl, $C_3$-$C_6$-alkenyloxycarbonyl-$C_1$-$C_6$-alkyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl and also the $C_3$-$C_6$-haloalkenyl moieties of $C_3$-$C_6$-haloalkenyloxy-$C_1$-$C_6$-alkyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl and also the $C_3$-$C_6$-alkynyl moieties of $C_3$-$C_6$-alkynyloxy, $C_3$-$C_6$-alkynylthio: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy and also the $C_1$-$C_4$-alkoxy moieties of $C_1$-$C_6$-alkoxycarbonyl: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkyoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_3$-$C_6$-alkenyloxy-$C_1$-$C_6$-alkoxy-$C_1$-$C_6$-alkyl, $C_1$-$C_6$-alkoxycarbonyl-$C_1$-$C_6$-alkyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy and also the $C_1$-$C_6$-haloalkoxy moieties of $C_1$-$C_6$-haloalkoxy-$C_1$-$C_6$-alkyl, $C_1$-$C_6$-haloalkoxycarbonyl-$C_1$-$C_6$-alkyl: a $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio and also the $C_1$-$C_6$-alkylthio moieties of $C_1$-$C_6$-alkylthio-$C_1$-$C_6$-alkyl: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-Alkyl-S(=O)—) and also the $C_1$-$C_6$-alkylsulfinyl moieties of $C_1$-$C_6$-alkylsulfinyl-$C_1$-$C_6$-alkyl, for example methylsulfinyl, ethylsulfinyl, propylsulfinyl, 1-methylethylsulfinyl, butylsulfinyl, 1-methylpropylsulfinyl, 2-methylpropylsulfinyl, 1,1-di-methylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentyl-sulfinyl, 1,1-dimethylbutylsulfinyl, 1,2-di methylbutylsulfinyl, 1,3-dimethylbutyl-sulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—) and also the $C_1$-$C_6$-alkylsulfonyl moieties of $C_1$-$C_6$-alkylsulfonyl-$C_1$-$C_6$-alkyl, for example methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methyl pentylsulfonyl, 1,1-dimethylbutylsulfonyl, 1,2-dimethylbutylsulfonyl, 1,3-dimethylbutylsulfonyl, 2,2-di methylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

($C_1$-$C_4$-alkyl)amino: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino and also the ($C_1$-$C_6$-alkyl)amino moieties of ($C_1$-$C_6$-alkyl)amino-$C_1$-$C_6$-alkyl, ($C_1$-$C_6$-alkyl)aminocarbonyl-$C_1$-$C_6$-alkyl: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_6$-alkyl)amino and also the di($C_1$-$C_6$-alkyl)amino moieties of di($C_1$-$C_6$-alkyl)amino-$C_1$-$C_6$-alkyl, di($C_1$-$C_6$-alkyl)aminocarbonyl-$C_1$-$C_6$-alkyl: di($C_1$-$C_4$-alkyl) amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclo-pentyl and cyclohexyl;

$C_3$-$C_6$-heterocyclyl: aliphatic heterocycle having 3 to 6 ring members which, in addition to carbon atoms, contains 1 to 4 nitrogen atoms, or 1 to 3 nitrogen atoms and an oxygen or sulphur atom, or an oxygen or a sulphur atom, for example three- or four-membered heterocycles like 2-oxetanyl, 3-oxetanyl, 2-thietanyl, 3-thietanyl, 1-azetidinyl, 2-azetidinyl, 1-azetinyl, 2-azetinyl; five-membered saturated heterocycles like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4-thiadiazolidin-5-yl, 1,2,4- triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, 1,3,4-triazolidin-2-yl; six-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, 2-morpholinyl, 3-morpholinyl;

- 5- or 6 membered heteroaryl: aromatic heteroaryl having 5 or 6 ring members which, in addition to carbon atoms, contains 1 to 4 nitrogen atoms, or 1 to 3 nitrogen atoms and an oxygen or sulphur atom, or an oxygen or a sulphur atom, for example 5-membered aromatic rings like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl); 1-tetrazolyl; 6-membered aromatic rings like pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl);
- 3- to 7-membered carbocyclus: a three- to seven-membered monocyclic, saturated, partial unsaturated or aromatic cycle having three to seven ring members which comprises apart from carbon atoms optionally one or two ring members selected from the group consisting of —N($R^{12}$)—, —N=N—, —C(=O)—, —O— and —S—.

The preferred embodiments of the invention mentioned herein below have to be understood as being preferred either independently from each other or in combination with one another.

According to a preferred embodiment of the invention preference is given to those phenylpyridines of formula (I), wherein the variables, either independently of one another or in combination with one another, have the following meanings:

Preferred are the phenylpyridines of formula (I), wherein
$R^1$ is halogen or $C_1$-$C_4$-haloalkyl;
particularly preferred Cl, $CF_3$ or $CF_2H$;
also particularly preferred $C_1$-$C_4$-haloalkyl;
especially preferred $CF_3$ or $CF_2H$;
more preferred $CF_3$.

Also preferred are the phenylpyridines of formula (I) wherein
$R^2$ is H or $CH_3$;
particularly preferred H;
also particularly preferred $CH_3$.

Also preferred are the phenylpyridines of formula (I) wherein
$R^3$ is F, Cl or Br;
preferably F or Cl;
particularly preferred F;
also particularly preferred Cl.

Also preferred are the phenylpyridines of formula (I) wherein
$R^4$ is H, F or Cl;
particularly preferred H or F;
especially preferred H;
also particularly preferred H or Cl;
especially preferred Cl;
also particularly preferred F or Cl;
especially preferred F.

Also preferred are the phenylpyridines of formula (I) wherein
$R^5$ is F, Cl, Br or CN;
particularly preferred F, Cl or CN;
especially preferred Cl or CN;
more preferred Cl;
also more preferred CN;
also especially preferred F or Cl;
more preferred F.

Also preferred are the phenylpyridines of formula (I) wherein
$R^6$ is H;
also preferred $CH_3$.

Also preferred are the phenylpyridines of formula (I) wherein
$R^7$ is $C_1$-$C_6$-alkoxy, $C_1$-$C_6$-haloalkoxy, $C_3$-$C_6$-alkenyloxy, $C_3$-$C_6$-alkynyloxy;
preferably $C_1$-$C_6$-alkoxy or $C_1$-$C_6$-haloalkoxy;
particularly preferred $C_1$-$C_4$-alkoxy or $C_1$-$C_4$-haloalkoxy;
also particularly preferred $C_1$-$C_6$-alkoxy;
especially preferred $C_1$-$C_4$-alkoxy;
more preferred $OCH_3$ or $OC_2H_5$;
most preferred is $OCH_3$.

Also preferred are the phenylpyridines of formula (I) wherein
$R^8$ is $OR^9$, $SR^9$, $NR^{10}R^{11}$, $NR^9S(O)_2R^9$ or $NR^9S(O)_2NR^{10}R^{11}$;
particularly preferred $OR^9$, $NR^{10}R^{11}$, $NR^9S(O)_2R^9$ or $NR^9S(O)_2NR^{10}R^{11}$;
especially preferred $OR^9$ or $NR^9S(O)_2R^9$.

Also preferred are the phenylpyridines of formula (I) wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, amino, ($C_1$-$C_6$-alkyl)amino, di($C_1$-$C_6$-alkyl)

amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
—N═$CR^{12}R^{13}$, wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, phenyl, phenyl-$C_1$-$C_4$-alkyl or a 5- or 6 membered heteroaryl,
  wherein each cycloalkyl, heterocyclyl, phenyl or heteroaryl ring can be substituted by one to four substituents selected from $R^{14}$ or a 3- to 7-membered carbocyclus,
    which carbocyclus optionally has in addition to carbon atoms one or two ring members selected from the group consisting of —N($R^{12}$)—, —N═N—, —C(═O)—, —O— and —S—, and
    which carbocyclus is optionally substituted with one to four substituents selected from $R^{14}$;
      wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
preferably hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
particularly preferred hydrogen, $C_1$-$C_6$-alkyl, $C_3$-$C_6$-alkenyl, $C_3$-$C_6$-alkynyl or $C_1$-$C_6$-haloalkyl;
especially preferred hydrogen, $C_1$-$C_6$-alkyl, or $C_3$-$C_6$-alkynyl;
more preferred hydrogen, $CH_3$, $C_2H_5$ or $CH_2C≡CH$.
Also preferred are the phenylpyridines of formula (I) wherein
$R^{10}$ is H or $C_1$-$C_6$-alkyl;
more preferred H;
also more preferred $C_1$-$C_6$-alkyl.
Also preferred are the phenylpyridines of formula (I) wherein
$R^{11}$ is $C_1$-$C_6$-alkyl.
Also preferred are the phenylpyridines of formula (I) wherein
$R^{12}$ is phenyl or $CH_3$;
particularly preferred phenyl;
also particularly preferred $C_1$-$C_4$-alkyl.
Also preferred are the phenylpyridines of formula (I) wherein
$R^{13}$ is phenyl or $CH_3$;
particularly preferred phenyl;
also particularly preferred $C_1$-$C_4$-alkyl.
Also preferred are the phenylpyridines of formula (I) wherein
$R^{14}$ is halogen or $C_1$-$C_6$-alkyl;
particularly preferred F, Cl or $CH_3$;
also particularly preferred halogen;
especially preferred F or Cl;
also particularly preferred $C_1$-$C_6$-alkyl;
especially preferred $CH_3$.
Also preferred are the phenylpyridines of formula (I) wherein
X is O;
also preferred S.

Also preferred are the phenylpyridines of formula (I) wherein
Y is O;
also preferred S.
Also preferred are the phenylpyridines of formula (I) wherein
$R^1$ is halogen or $C_1$-$C_4$-haloalkyl;
particularly preferred Cl, $CF_3$ or $CF_2H$;
also particularly preferred $C_1$-$C_4$-haloalkyl;
especially preferred $CF_3$ or $CF_2H$;
more preferred $CF_3$;
$R^2$ is H or $CH_3$;
particularly preferred H;
also particularly preferred $CH_3$;
$R^3$ is F or Cl;
particularly preferred F;
also particularly preferred Cl;
$R^4$ is H, F or Cl;
particularly preferred H or F;
especially preferred H;
also particularly preferred H or Cl;
especially preferred Cl;
also particularly preferred F or Cl;
especially preferred F;
$R^5$ is F, Cl, Br or CN;
particularly preferred F, Cl or CN;
especially preferred Cl or CN;
more preferred Cl;
also more preferred CN;
also especially preferred F or Cl;
more preferred F;
$R^6$ is H;
also preferred $CH_3$;
$R^7$ is $C_1$-$C_6$-alkoxy or $C_1$-$C_6$-haloalkoxy;
particularly preferred $C_1$-$C_4$-alkoxy or $C_1$-$C_4$-haloalkoxy;
also particularly preferred $C_1$-$C_6$-alkoxy;
especially preferred $C_1$-$C_4$-alkoxy;
more preferred $OCH_3$ or $OC_2H_5$;
most preferred is $OCH_3$;
$R^8$ is $OR^9$, $SR^9$, $NR^{10}R^{11}$, $NR^9S(O)_2R^9$ or $NR^9S(O)_2NR^{10}R^{11}$;
particularly preferred $OR^9$, $NR^{10}R^{11}$, $NR^9S(O)_2R^9$ or $NR^9S(O)_2NR^{10}R^{11}$;
especially preferred $OR^9$ or $NR^9S(O)_2R^9$;
$R^9$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
particularly preferred hydrogen, $C_1$-$C_6$-alkyl, $C_3$-$C_6$-alkenyl, $C_3$-$C_6$-alkynyl or $C_1$-$C_6$-haloalkyl;
especially preferred hydrogen, $C_1$-$C_6$-alkyl, or $C_3$-$C_6$-alkynyl;
more preferred hydrogen, $CH_3$, $C_2H_5$ or $CH_2C≡CH$;
$R^{10}$ is H or $C_1$-$C_6$-alkyl;
more preferred H;
also more preferred $C_1$-$C_6$-alkyl;
$R^{11}$ is $C_1$-$C_6$-alkyl;
$R^{12}$ is phenyl or $CH_3$;
particularly preferred phenyl;
also particularly preferred $C_1$-$C_4$-alkyl;
$R^{13}$ is phenyl or $CH_3$;
particularly preferred phenyl;
also particularly preferred $C_1$-$C_4$-alkyl;
$R^{14}$ is halogen or $C_1$-$C_6$-alkyl;
particularly preferred F, Cl or $CH_3$;
also particularly preferred halogen;

especially preferred F or Cl;
also particularly preferred $C_1$-$C_6$-alkyl;
especially preferred $CH_3$;
X is O;
   also preferred S; and
Y is O;
   also preferred S.
Also preferred are the phenylpyridines of formula (I) wherein
   $R^1$ is halogen or $C_1$-$C_4$-haloalkyl;
   $R^2$ is H;
   $R^3$ is Cl or F;
   $R^4$ is H or F;
   $R^5$ is Cl or CN;
   $R^6$ is H;
   $R^7$ is $C_1$-$C_6$-alkoxy;
   $R^8$ is $OR^9$, $NR^{10}R^{11}$, $NR^9S(O)_2R^9$ or $NR^9S(O)_2NR^{10}R^{11}$, wherein
      $R^9$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
      $R^{10}$ is H or $C_1$-$C_6$-alkyl; and
      $R^{11}$ is $C_1$-$C_6$-alkyl.
Also preferred are the phenylpyridines of formula (I) wherein
   $R^1$ is $C_1$-$C_4$-haloalkyl;
   $R^2$ and $R^6$ are H;
   $R^3$, $R^4$ and $R^5$ are halogen;
   $R^7$ is $C_1$-$C_6$-alkoxy; and
   $R^8$ is $OR^9$ or $NR^9S(O)_2R^9$, wherein $R^9$ is H, $C_1$-$C_6$-alkyl or $C_3$-$C_6$-alkynyl.
Particularly preferred are the phenylpyridines of formula (I) wherein
   $R^1$ is $CF_3$;
   $R^2$ and $R^6$ are H;
   $R^3$ and $R^5$ are Cl;
   $R^4$ is F;
   $R^7$ is $C_1$-$C_6$-alkoxy; and
   $R^8$ is $OR^9$ or $NR^9S(O)_2R^9$, wherein $R^9$ is H, $C_1$-$C_6$-alkyl or $C_3$-$C_6$-alkynyl.
Also particularly preferred are the phenylpyridines of formula (I) wherein
   $R^1$ is $CF_3$;
   $R^2$ and $R^6$ are H;
   $R^3$ and $R^5$ are Cl;
   $R^4$ is F;
   $R^7$ is $OCH_3$;
   $R^8$ is $OR^9$ or $NR^9S(O)_2R^9$, wherein $R^9$ is H, $CH_3$, $C_2CH_5$, $CH(CH_3)_2$ or $CH_2C{\equiv}CH$.
Particular preference is given to phenylpyridines of formula (I.a) (corresponds to phenylpyridines of formula (I), wherein $R^1$ is $CF_3$, $R^2$ is H, $R^5$ is Cl, $R^6$ is H, X and Y are O),

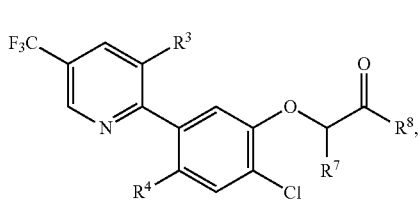

(I.a)

wherein the variables $R^3$, $R^4$, $R^7$ and $R^8$ have the meanings, in particular the preferred meanings, as defined above.

Special preference is given to the compounds of the formulae I.a.1 to I.a.264 of Table (I), where the definitions of the variables $R^3$, $R^4$, $R^7$ and $R^8$ are of particular importance for the compounds according to the invention not only in combination with one another but in each case also on their own:

TABLE (I)

| No. | $R^3$ | $R^4$ | $R^7$ | $R^8$ |
|---|---|---|---|---|
| I.a.1 | F | H | $OCH_3$ | OH |
| I.a.2 | F | H | $OCH_3$ | $OCH_3$ |
| I.a.3 | F | H | $OCH_3$ | $OCH_2CH_3$ |
| I.a.4 | F | H | $OCH_3$ | $OCH(CH_3)_2$ |
| I.a.5 | F | H | $OCH_3$ | $OCH_2CH_2CH_3$ |
| I.a.6 | F | H | $OCH_3$ | $OCH_2CH(CH_3)_2$ |
| I.a.7 | F | H | $OCH_3$ | $OCH_2CH{=}CH_2$ |
| I.a.8 | F | H | $OCH_3$ | $OCH_3C(CH_3){=}CH_2$ |
| I.a.9 | F | H | $OCH_3$ | $OCH_2C{\equiv}CH$ |
| I.a.10 | F | H | $OCH_3$ | $OCH_2CF_3$ |
| I.a.11 | F | H | $OCH_3$ | $OCH_2CHF_2$ |
| I.a.12 | F | H | $OCH_3$ | $OCH_2OCH_3$ |
| I.a.13 | F | H | $OCH_3$ | $OCH_2OCH_2CH_3$ |
| I.a.14 | F | H | $OCH_3$ | $OCH_2CH_2OCH_3$ |
| I.a.15 | F | H | $OCH_3$ | $OCH_2CH_2OCH_2CH_3$ |
| I.a.16 | F | H | $OCH_3$ | $OCH_2CH_2CH_2OCH_3$ |
| I.a.17 | F | H | $OCH_3$ | $OCH_2CH(OCH_3)_2$ |
| I.a.18 | F | H | $OCH_3$ | $OCH_2(CO)OCH_3$ |
| I.a.19 | F | H | $OCH_3$ | $OCH_2(CO)OCH_2CH_3$ |
| I.a.20 | F | H | $OCH_3$ | $OCH(CH_3)(CO)OCH_3$ |
| I.a.21 | F | H | $OCH_3$ | $OCH(CH_3)(CO)OCH_2CH_3$ |
| I.a.22 | F | H | $OCH_3$ | $OC(CH_3)_2(CO)OCH_3$ |
| I.a.23 | F | H | $OCH_3$ | $OC(CH_3)_2(CO)OCH_2CH_3$ |
| I.a.24 | F | H | $OCH_3$ | $OCH_2$-cyclopropyl |
| I.a.25 | F | H | $OCH_3$ | $OCH_2$-cyclobutyl |
| I.a.26 | F | H | $OCH_3$ | $NHCH_3$ |
| I.a.27 | F | H | $OCH_3$ | $N(CH_3)_2$ |
| I.a.28 | F | H | $OCH_3$ | $N(CH_3)(CH_2CH_3)$ |
| I.a.29 | F | H | $OCH_3$ | $N(CH_2CH_3)_2$ |
| I.a.30 | F | H | $OCH_3$ | $NHSO_2CH_3$ |
| I.a.31 | F | H | $OCH_3$ | $NHSO_2CH_2CH_3$ |
| I.a.32 | F | H | $OCH_3$ | $NHSO_2N(CH_3)_2$ |
| I.a.33 | F | H | $OCH_3$ | $NHSO_2N(CH_3)[CH(CH_3)_2]$ |
| I.a.34 | F | H | $OCH_2CH_3$ | OH |
| I.a.35 | F | H | $OCH_2CH_3$ | $OCH_3$ |
| I.a.36 | F | H | $OCH_2CH_3$ | $OCH_2CH_3$ |
| I.a.37 | F | H | $OCH_2CH_3$ | $OCH(CH_3)_2$ |
| I.a.38 | F | H | $OCH_2CH_3$ | $OCH_2CH_2CH_3$ |
| I.a.39 | F | H | $OCH_2CH_3$ | $OCH_2CH(CH_3)_2$ |
| I.a.40 | F | H | $OCH_2CH_3$ | $OCH_2CH{=}CH_2$ |
| I.a.41 | F | H | $OCH_2CH_3$ | $OCH_3C(CH_3){=}CH_2$ |
| I.a.42 | F | H | $OCH_2CH_3$ | $OCH_2C{\equiv}CH$ |
| I.a.43 | F | H | $OCH_2CH_3$ | $OCH_2CF_3$ |
| I.a.44 | F | H | $OCH_2CH_3$ | $OCH_2CHF_2$ |
| I.a.45 | F | H | $OCH_2CH_3$ | $OCH_2OCH_3$ |
| I.a.46 | F | H | $OCH_2CH_3$ | $OCH_2OCH_2CH_3$ |
| I.a.47 | F | H | $OCH_2CH_3$ | $OCH_2CH_2OCH_3$ |
| I.a.48 | F | H | $OCH_2CH_3$ | $OCH_2CH_2OCH_2CH_3$ |
| I.a.49 | F | H | $OCH_2CH_3$ | $OCH_2CH_2CH_2OCH_3$ |
| I.a.50 | F | H | $OCH_2CH_3$ | $OCH_2CH(OCH_3)_2$ |
| I.a.51 | F | H | $OCH_2CH_3$ | $OCH_2(CO)OCH_3$ |
| I.a.52 | F | H | $OCH_2CH_3$ | $OCH_2(CO)OCH_2CH_3$ |
| I.a.53 | F | H | $OCH_2CH_3$ | $OCH(CH_3)(CO)OCH_3$ |
| I.a.54 | F | H | $OCH_2CH_3$ | $OCH(CH_3)(CO)OCH_2CH_3$ |
| I.a.55 | F | H | $OCH_2CH_3$ | $OC(CH_3)_2(CO)OCH_3$ |
| I.a.56 | F | H | $OCH_2CH_3$ | $OC(CH_3)_2(CO)OCH_2CH_3$ |
| I.a.57 | F | H | $OCH_2CH_3$ | $OCH_2$-cyclopropyl |
| I.a.58 | F | H | $OCH_2CH_3$ | $OCH_2$-cyclobutyl |
| I.a.59 | F | H | $OCH_2CH_3$ | $NHCH_3$ |
| I.a.60 | F | H | $OCH_2CH_3$ | $N(CH_3)_2$ |
| I.a.61 | F | H | $OCH_2CH_3$ | $N(CH_3)(CH_2CH_3)$ |
| I.a.62 | F | H | $OCH_2CH_3$ | $N(CH_2CH_3)_2$ |
| I.a.63 | F | H | $OCH_2CH_3$ | $NHSO_2CH_3$ |
| I.a.64 | F | H | $OCH_2CH_3$ | $NHSO_2CH_2CH_3$ |
| I.a.65 | F | H | $OCH_2CH_3$ | $NHSO_2N(CH_3)_2$ |
| I.a.66 | F | H | $OCH_2CH_3$ | $NHSO_2N(CH_3)[CH(CH_3)_2]$ |

TABLE (I)-continued

| No. | $R^3$ | $R^4$ | $R^7$ | $R^8$ |
|---|---|---|---|---|
| I.a.67 | F | F | OCH$_3$ | OH |
| I.a.68 | F | F | OCH$_3$ | OCH$_3$ |
| I.a.69 | F | F | OCH$_3$ | OCH$_2$CH$_3$ |
| I.a.70 | F | F | OCH$_3$ | OCH(CH$_3$)$_2$ |
| I.a.71 | F | F | OCH$_3$ | OCH$_2$CH$_2$CH$_3$ |
| I.a.72 | F | F | OCH$_3$ | OCH$_2$CH(CH$_3$)$_2$ |
| I.a.73 | F | F | OCH$_3$ | OCH$_2$CH=CH$_2$ |
| I.a.74 | F | F | OCH$_3$ | OCH$_3$C(CH$_3$)=CH$_2$ |
| I.a.75 | F | F | OCH$_3$ | OCH$_2$C≡CH |
| I.a.76 | F | F | OCH$_3$ | OCH$_2$CF$_3$ |
| I.a.77 | F | F | OCH$_3$ | OCH$_2$CHF$_2$ |
| I.a.78 | F | F | OCH$_3$ | OCH$_2$OCH$_3$ |
| I.a.79 | F | F | OCH$_3$ | OCH$_2$OCH$_2$CH$_3$ |
| I.a.80 | F | F | OCH$_3$ | OCH$_2$CH$_2$OCH$_3$ |
| I.a.81 | F | F | OCH$_3$ | OCH$_2$CH$_2$OCH$_2$CH$_3$ |
| I.a.82 | F | F | OCH$_3$ | OCH$_2$CH$_2$CH$_2$OCH$_3$ |
| I.a.83 | F | F | OCH$_3$ | OCH$_2$CH(OCH$_3$)$_2$ |
| I.a.84 | F | F | OCH$_3$ | OCH$_2$(CO)OCH$_3$ |
| I.a.85 | F | F | OCH$_3$ | OCH$_2$(CO)OCH$_2$CH$_3$ |
| I.a.86 | F | F | OCH$_3$ | OCH(CH$_3$)(CO)OCH$_3$ |
| I.a.87 | F | F | OCH$_3$ | OCH(CH$_3$)(CO)OCH$_2$CH$_3$ |
| I.a.88 | F | F | OCH$_3$ | OC(CH$_3$)$_2$(CO)OCH$_3$ |
| I.a.89 | F | F | OCH$_3$ | OC(CH$_3$)$_2$(CO)OCH$_2$CH$_3$ |
| I.a.90 | F | F | OCH$_3$ | OCH$_2$-cyclopropyl |
| I.a.91 | F | F | OCH$_3$ | OCH$_2$-cyclobutyl |
| I.a.92 | F | F | OCH$_3$ | NHCH$_3$ |
| I.a.93 | F | F | OCH$_3$ | N(CH$_3$)$_2$ |
| I.a.94 | F | F | OCH$_3$ | N(CH$_3$)(CH$_2$CH$_3$) |
| I.a.95 | F | F | OCH$_3$ | N(CH$_2$CH$_3$)$_2$ |
| I.a.96 | F | F | OCH$_3$ | NHSO$_2$CH$_3$ |
| I.a.97 | F | F | OCH$_3$ | NHSO$_2$CH$_2$CH$_3$ |
| I.a.98 | F | F | OCH$_3$ | NHSO$_2$N(CH$_3$)$_2$ |
| I.a.99 | F | F | OCH$_3$ | NHSO$_2$N(CH$_3$)[CH(CH$_3$)$_2$] |
| I.a.100 | F | F | OCH$_2$CH$_3$ | OH |
| I.a.101 | F | F | OCH$_2$CH$_3$ | OCH$_3$ |
| I.a.102 | F | F | OCH$_2$CH$_3$ | OCH$_2$CH$_3$ |
| I.a.103 | F | F | OCH$_2$CH$_3$ | OCH(CH$_3$)$_2$ |
| I.a.104 | F | F | OCH$_2$CH$_3$ | OCH$_2$CH$_2$CH$_3$ |
| I.a.105 | F | F | OCH$_2$CH$_3$ | OCH$_2$CH(CH$_3$)$_2$ |
| I.a.106 | F | F | OCH$_2$CH$_3$ | OCH$_2$CH=CH$_2$ |
| I.a.107 | F | F | OCH$_2$CH$_3$ | OCH$_3$C(CH$_3$)=CH$_2$ |
| I.a.108 | F | F | OCH$_2$CH$_3$ | OCH$_2$C≡CH |
| I.a.109 | F | F | OCH$_2$CH$_3$ | OCH$_2$CF$_3$ |
| I.a.110 | F | F | OCH$_2$CH$_3$ | OCH$_2$CHF$_2$ |
| I.a.111 | F | F | OCH$_2$CH$_3$ | OCH$_2$OCH$_3$ |
| I.a.112 | F | F | OCH$_2$CH$_3$ | OCH$_2$OCH$_2$CH$_3$ |
| I.a.113 | F | F | OCH$_2$CH$_3$ | OCH$_2$CH$_2$OCH$_3$ |
| I.a.114 | F | F | OCH$_2$CH$_3$ | OCH$_2$CH$_2$OCH$_2$CH$_3$ |
| I.a.115 | F | F | OCH$_2$CH$_3$ | OCH$_2$CH$_2$CH$_2$OCH$_3$ |
| I.a.116 | F | F | OCH$_2$CH$_3$ | OCH$_2$CH(OCH$_3$)$_2$ |
| I.a.117 | F | F | OCH$_2$CH$_3$ | OCH$_2$(CO)OCH$_3$ |
| I.a.118 | F | F | OCH$_2$CH$_3$ | OCH$_2$(CO)OCH$_2$CH$_3$ |
| I.a.119 | F | F | OCH$_2$CH$_3$ | OCH(CH$_3$)(CO)OCH$_3$ |
| I.a.120 | F | F | OCH$_2$CH$_3$ | OCH(CH$_3$)(CO)OCH$_2$CH$_3$ |
| I.a.121 | F | F | OCH$_2$CH$_3$ | OC(CH$_3$)$_2$(CO)OCH$_3$ |
| I.a.122 | F | F | OCH$_2$CH$_3$ | OC(CH$_3$)$_2$(CO)OCH$_2$CH$_3$ |
| I.a.123 | F | F | OCH$_2$CH$_3$ | OCH$_2$-cyclopropyl |
| I.a.124 | F | F | OCH$_2$CH$_3$ | OCH$_2$-cyclobutyl |
| I.a.125 | F | F | OCH$_2$CH$_3$ | NHCH$_3$ |
| I.a.126 | F | F | OCH$_2$CH$_3$ | N(CH$_3$)$_2$ |
| I.a.127 | F | F | OCH$_2$CH$_3$ | N(CH$_3$)(CH$_2$CH$_3$) |
| I.a.128 | F | F | OCH$_2$CH$_3$ | N(CH$_2$CH$_3$)$_2$ |
| I.a.129 | F | F | OCH$_2$CH$_3$ | NHSO$_2$CH$_3$ |
| I.a.130 | F | F | OCH$_2$CH$_3$ | NHSO$_2$CH$_2$CH$_3$ |
| I.a.131 | F | F | OCH$_2$CH$_3$ | NHSO$_2$N(CH$_3$)$_2$ |
| I.a.132 | F | F | OCH$_2$CH$_3$ | NHSO$_2$N(CH$_3$)[CH(CH$_3$)$_2$] |
| I.a.133 | Cl | H | OCH$_3$ | OH |
| I.a.134 | Cl | H | OCH$_3$ | OCH$_3$ |
| I.a.135 | Cl | H | OCH$_3$ | OCH$_2$CH$_3$ |
| I.a.136 | Cl | H | OCH$_3$ | OCH(CH$_3$)$_2$ |
| I.a.137 | Cl | H | OCH$_3$ | OCH$_2$CH$_2$CH$_3$ |
| I.a.138 | Cl | H | OCH$_3$ | OCH$_2$CH(CH$_3$)$_2$ |
| I.a.139 | Cl | H | OCH$_3$ | OCH$_2$CH=CH$_2$ |
| I.a.140 | Cl | H | OCH$_3$ | OCH$_3$C(CH$_3$)=CH$_2$ |
| I.a.141 | Cl | H | OCH$_3$ | OCH$_2$C≡CH |
| I.a.142 | Cl | H | OCH$_3$ | OCH$_2$CF$_3$ |
| I.a.143 | Cl | H | OCH$_3$ | OCH$_2$CHF$_2$ |
| I.a.144 | Cl | H | OCH$_3$ | OCH$_2$OCH$_3$ |
| I.a.145 | Cl | H | OCH$_3$ | OCH$_2$OCH$_2$CH$_3$ |
| I.a.146 | Cl | H | OCH$_3$ | OCH$_2$CH$_2$OCH$_3$ |
| I.a.147 | Cl | H | OCH$_3$ | OCH$_2$CH$_2$OCH$_2$CH$_3$ |
| I.a.148 | Cl | H | OCH$_3$ | OCH$_2$CH$_2$CH$_2$OCH$_3$ |
| I.a.149 | Cl | H | OCH$_3$ | OCH$_2$CH(OCH$_3$)$_2$ |
| I.a.150 | Cl | H | OCH$_3$ | OCH$_2$(CO)OCH$_3$ |
| I.a.151 | Cl | H | OCH$_3$ | OCH$_2$(CO)OCH$_2$CH$_3$ |
| I.a.152 | Cl | H | OCH$_3$ | OCH(CH$_3$)(CO)OCH$_3$ |
| I.a.153 | Cl | H | OCH$_3$ | OCH(CH$_3$)(CO)OCH$_2$CH$_3$ |
| I.a.154 | Cl | H | OCH$_3$ | OC(CH$_3$)$_2$(CO)OCH$_3$ |
| I.a.155 | Cl | H | OCH$_3$ | OC(CH$_3$)$_2$(CO)OCH$_2$CH$_3$ |
| I.a.156 | Cl | H | OCH$_3$ | OCH$_2$-cyclopropyl |
| I.a.157 | Cl | H | OCH$_3$ | OCH$_2$-cyclobutyl |
| I.a.158 | Cl | H | OCH$_3$ | NHCH$_3$ |
| I.a.159 | Cl | H | OCH$_3$ | N(CH$_3$)$_2$ |
| I.a.160 | Cl | H | OCH$_3$ | N(CH$_3$)(CH$_2$CH$_3$) |
| I.a.161 | Cl | H | OCH$_3$ | N(CH$_2$CH$_3$)$_2$ |
| I.a.162 | Cl | H | OCH$_3$ | NHSO$_2$CH$_3$ |
| I.a.163 | Cl | H | OCH$_3$ | NHSO$_2$CH$_2$CH$_3$ |
| I.a.164 | Cl | H | OCH$_3$ | NHSO$_2$N(CH$_3$)$_2$ |
| I.a.165 | Cl | H | OCH$_3$ | NHSO$_2$N(CH$_3$)[CH(CH$_3$)$_2$] |
| I.a.166 | Cl | H | OCH$_2$CH$_3$ | OH |
| I.a.167 | Cl | H | OCH$_2$CH$_3$ | OCH$_3$ |
| I.a.168 | Cl | H | OCH$_2$CH$_3$ | OCH$_2$CH$_3$ |
| I.a.169 | Cl | H | OCH$_2$CH$_3$ | OCH(CH$_3$)$_2$ |
| I.a.170 | Cl | H | OCH$_2$CH$_3$ | OCH$_2$CH$_2$CH$_3$ |
| I.a.171 | Cl | H | OCH$_2$CH$_3$ | OCH$_2$CH(CH$_3$)$_2$ |
| I.a.172 | Cl | H | OCH$_2$CH$_3$ | OCH$_2$CH=CH$_2$ |
| I.a.173 | Cl | H | OCH$_2$CH$_3$ | OCH$_3$C(CH$_3$)=CH$_2$ |
| I.a.174 | Cl | H | OCH$_2$CH$_3$ | OCH$_2$C≡CH |
| I.a.175 | Cl | H | OCH$_2$CH$_3$ | OCH$_2$CF$_3$ |
| I.a.176 | Cl | H | OCH$_2$CH$_3$ | OCH$_2$CHF$_2$ |
| I.a.177 | Cl | H | OCH$_2$CH$_3$ | OCH$_2$OCH$_3$ |
| I.a.178 | Cl | H | OCH$_2$CH$_3$ | OCH$_2$OCH$_2$CH$_3$ |
| I.a.179 | Cl | H | OCH$_2$CH$_3$ | OCH$_2$CH$_2$OCH$_3$ |
| I.a.180 | Cl | H | OCH$_2$CH$_3$ | OCH$_2$CH$_2$OCH$_2$CH$_3$ |
| I.a.181 | Cl | H | OCH$_2$CH$_3$ | OCH$_2$CH$_2$CH$_2$OCH$_3$ |
| I.a.182 | Cl | H | OCH$_2$CH$_3$ | OCH$_2$CH(OCH$_3$)$_2$ |
| I.a.183 | Cl | H | OCH$_2$CH$_3$ | OCH$_2$(CO)OCH$_3$ |
| I.a.184 | Cl | H | OCH$_2$CH$_3$ | OCH$_2$(CO)OCH$_2$CH$_3$ |
| I.a.185 | Cl | H | OCH$_2$CH$_3$ | OCH(CH$_3$)(CO)OCH$_3$ |
| I.a.186 | Cl | H | OCH$_2$CH$_3$ | OCH(CH$_3$)(CO)OCH$_2$CH$_3$ |
| I.a.187 | Cl | H | OCH$_2$CH$_3$ | OC(CH$_3$)$_2$(CO)OCH$_3$ |
| I.a.188 | Cl | H | OCH$_2$CH$_3$ | OC(CH$_3$)$_2$(CO)OCH$_2$CH$_3$ |
| I.a.189 | Cl | H | OCH$_2$CH$_3$ | OCH$_2$-cyclopropyl |
| I.a.190 | Cl | H | OCH$_2$CH$_3$ | OCH$_2$-cyclobutyl |
| I.a.191 | Cl | H | OCH$_2$CH$_3$ | NHCH$_3$ |
| I.a.192 | Cl | H | OCH$_2$CH$_3$ | N(CH$_3$)$_2$ |
| I.a.193 | Cl | H | OCH$_2$CH$_3$ | N(CH$_3$)(CH$_2$CH$_3$) |
| I.a.194 | Cl | H | OCH$_2$CH$_3$ | N(CH$_2$CH$_3$)$_2$ |
| I.a.195 | Cl | H | OCH$_2$CH$_3$ | NHSO$_2$CH$_3$ |
| I.a.196 | Cl | H | OCH$_2$CH$_3$ | NHSO$_2$CH$_2$CH$_3$ |
| I.a.197 | Cl | H | OCH$_2$CH$_3$ | NHSO$_2$N(CH$_3$)$_2$ |
| I.a.198 | Cl | H | OCH$_2$CH$_3$ | NHSO$_2$N(CH$_3$)[CH(CH$_3$)$_2$] |
| I.a.199 | Cl | F | OCH$_3$ | OH |
| I.a.200 | Cl | F | OCH$_3$ | OCH$_3$ |
| I.a.201 | Cl | F | OCH$_3$ | OCH$_2$CH$_3$ |
| I.a.202 | Cl | F | OCH$_3$ | OCH(CH$_3$)$_2$ |
| I.a.203 | Cl | F | OCH$_3$ | OCH$_2$CH$_2$CH$_3$ |
| I.a.204 | Cl | F | OCH$_3$ | OCH$_2$CH(CH$_3$)$_2$ |
| I.a.205 | Cl | F | OCH$_3$ | OCH$_2$CH=CH$_2$ |
| I.a.206 | Cl | F | OCH$_3$ | OCH$_3$C(CH$_3$)=CH$_2$ |
| I.a.207 | Cl | F | OCH$_3$ | OCH$_2$C≡CH |
| I.a.208 | Cl | F | OCH$_3$ | OCH$_2$CF$_3$ |
| I.a.209 | Cl | F | OCH$_3$ | OCH$_2$CHF$_2$ |
| I.a.210 | Cl | F | OCH$_3$ | OCH$_2$OCH$_3$ |
| I.a.211 | Cl | F | OCH$_3$ | OCH$_2$OCH$_2$CH$_3$ |
| I.a.212 | Cl | F | OCH$_3$ | OCH$_2$CH$_2$OCH$_3$ |
| I.a.213 | Cl | F | OCH$_3$ | OCH$_2$CH$_2$OCH$_2$CH$_3$ |
| I.a.214 | Cl | F | OCH$_3$ | OCH$_2$CH$_2$CH$_2$OCH$_3$ |
| I.a.215 | Cl | F | OCH$_3$ | OCH$_2$CH(OCH$_3$)$_2$ |
| I.a.216 | Cl | F | OCH$_3$ | OCH$_2$(CO)OCH$_3$ |
| I.a.217 | Cl | F | OCH$_3$ | OCH$_2$(CO)OCH$_2$CH$_3$ |
| I.a.218 | Cl | F | OCH$_3$ | OCH(CH$_3$)(CO)OCH$_3$ |
| I.a.219 | Cl | F | OCH$_3$ | OCH(CH$_3$)(CO)OCH$_2$CH$_3$ |
| I.a.220 | Cl | F | OCH$_3$ | OC(CH$_3$)$_2$(CO)OCH$_3$ |
| I.a.221 | Cl | F | OCH$_3$ | OC(CH$_3$)$_2$(CO)OCH$_2$CH$_3$ |
| I.a.222 | Cl | F | OCH$_3$ | OCH$_2$-cyclopropyl |

TABLE (I)-continued

| No. | R³ | R⁴ | R⁷ | R⁸ |
|---|---|---|---|---|
| I.a.223 | Cl | F | OCH₃ | OCH₂-cyclobutyl |
| I.a.224 | Cl | F | OCH₃ | NHCH₃ |
| I.a.225 | Cl | F | OCH₃ | N(CH₃)₂ |
| I.a.226 | Cl | F | OCH₃ | N(CH₃)(CH₂CH₃) |
| I.a.227 | Cl | F | OCH₃ | N(CH₂CH₃)₂ |
| I.a.228 | Cl | F | OCH₃ | NHSO₂CH₃ |
| I.a.229 | Cl | F | OCH₃ | NHSO₂CH₂CH₃ |
| I.a.230 | Cl | F | OCH₃ | NHSO₂N(CH₃)₂ |
| I.a.231 | Cl | F | OCH₃ | NHSO₂N(CH₃)[CH(CH₃)₂] |
| I.a.232 | Cl | F | OCH₂CH₃ | OH |
| I.a.233 | Cl | F | OCH₂CH₃ | OCH₃ |
| I.a.234 | Cl | F | OCH₂CH₃ | OCH₂CH₃ |
| I.a.235 | Cl | F | OCH₂CH₃ | OCH(CH₃)₂ |
| I.a.236 | Cl | F | OCH₂CH₃ | OCH₂CH₂CH₃ |
| I.a.237 | Cl | F | OCH₂CH₃ | OCH₂CH(CH₃)₂ |
| I.a.238 | Cl | F | OCH₂CH₃ | OCH₂CH=CH₂ |
| I.a.239 | Cl | F | OCH₂CH₃ | OCH₃C(CH₃)=CH₂ |
| I.a.240 | Cl | F | OCH₂CH₃ | OCH₂C≡CH |
| I.a.241 | Cl | F | OCH₂CH₃ | OCH₂CF₃ |
| I.a.242 | Cl | F | OCH₂CH₃ | OCH₂CHF₂ |
| I.a.243 | Cl | F | OCH₂CH₃ | OCH₂OCH₃ |
| I.a.244 | Cl | F | OCH₂CH₃ | OCH₂OCH₂CH₃ |
| I.a.245 | Cl | F | OCH₂CH₃ | OCH₂CH₂OCH₃ |
| I.a.246 | Cl | F | OCH₂CH₃ | OCH₂CH₂OCH₂CH₃ |
| I.a.247 | Cl | F | OCH₂CH₃ | OCH₂CH₂CH₂OCH₃ |
| I.a.248 | Cl | F | OCH₂CH₃ | OCH₂CH(OCH₃)₂ |
| I.a.249 | Cl | F | OCH₂CH₃ | OCH₂(CO)OCH₃ |
| I.a.250 | Cl | F | OCH₂CH₃ | OCH₂(CO)OCH₂CH₃ |
| I.a.251 | Cl | F | OCH₂CH₃ | OCH(CH₃)(CO)OCH₃ |
| I.a.252 | Cl | F | OCH₂CH₃ | OCH(CH₃)(CO)OCH₂CH₃ |
| I.a.253 | Cl | F | OCH₂CH₃ | OC(CH₃)₂(CO)OCH₃ |
| I.a.254 | Cl | F | OCH₂CH₃ | OC(CH₃)₂(CO)OCH₂CH₃ |
| I.a.255 | Cl | F | OCH₂CH₃ | OCH₂-cyclopropyl |
| I.a.256 | Cl | F | OCH₂CH₃ | OCH₂-cyclobutyl |
| I.a.257 | Cl | F | OCH₂CH₃ | NHCH₃ |
| I.a.258 | Cl | F | OCH₂CH₃ | N(CH₃)₂ |
| I.a.259 | Cl | F | OCH₂CH₃ | N(CH₃)(CH₂CH₃) |
| I.a.260 | Cl | F | OCH₂CH₃ | N(CH₂CH₃)₂ |
| I.a.261 | Cl | F | OCH₂CH₃ | NHSO₂CH₃ |
| I.a.262 | Cl | F | OCH₂CH₃ | NHSO₂CH₂CH₃ |
| I.a.263 | Cl | F | OCH₂CH₃ | NHSO₂N(CH₃)₂ |
| I.a.264 | Cl | F | OCH₂CH₃ | NHSO₂N(CH₃)[CH(CH₃)₂] |

Also preferred are the phenylpyridines of formula (I.b), particularly preferred the phenylpyridines of formulae (I.b.1) to (I.b.264), which differ from the corresponding phenylpyridines of formulae (I.a) as well as (I.a.1) to (I.a.264) only in that R⁵ is CN:

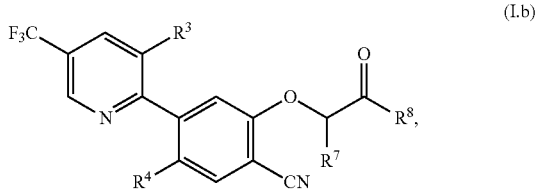

(I.b)

Also preferred are the phenylpyridines of formula (I.c), particularly preferred the phenylpyridines of formulae (I.c.1) to (I.c.264), which differ from the corresponding phenylpyridines of formulae (I.a) as well as (I.a.1) to (I.a.264) only in that R⁵ is F:

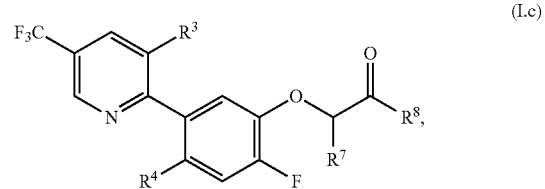

(I.c)

The phenylpyridines of formula (I) according to the invention can be prepared by standard processes of organic chemistry (e.g. WO 97/06143; U.S. Pat. No. 5,968,874), for example by the following processes:

Process A)

The phenylpyridines of formula (I) are obtained from acid chlorides (II) by reaction with compounds (III) in the presence of a base:

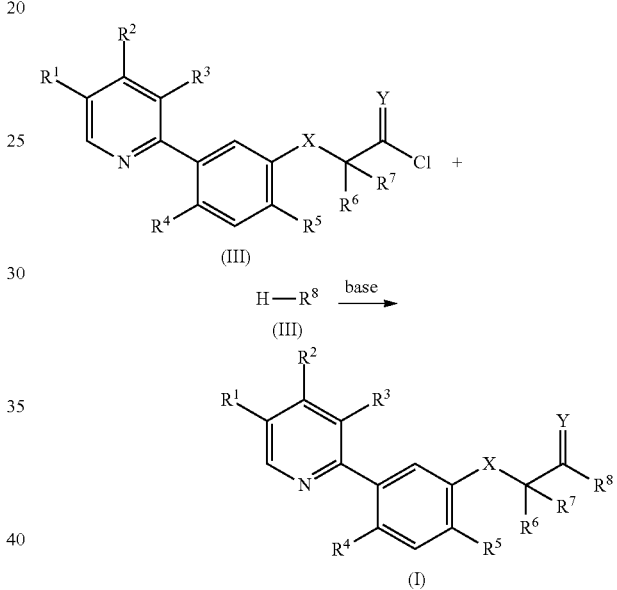

Instead of the acid chlorides (II), also the respective acid in combination with an activating reagent, like carbonyldiimidazole, DCC, EDC or N-methyl-2-chloropyridinium chloride can be used. The reaction conditions are the same as described for the acid chlorides (II).

The compounds (III) can also be employed in the form of their salts, in particular the sodium and potassium salts, in which case the presence of a base is not necessary.

The reaction of acid chlorides (II) with compounds (III) is usually carried out at from 0° C. to the boiling point of the reaction mixture, preferably at from 0° C. to 100° C., particularly preferably at from 0° C. to 40° C., in an inert organic solvent in the presence of a base.

The reaction may in principle be carried out in substance. However, preference is given to reacting the acid chlorides (II) with the compounds (III) in an organic solvent.

Suitable in principle are all solvents which are capable of dissolving the acid chlorides (II) and the compounds (III) at least partly and preferably fully under reaction conditions.

Examples of suitable solvents are aliphatic hydrocarbons such as pentane, hexane, cyclohexane, nitromethane and mixtures of C₅-C₈-alkanes; aromatic hydrocarbons such as benzene, chlorobenzene, tolene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tert-butyl methyl ketone, cyclohexanone; dipolar aprotic solvents such as sulfolane, dimethylsulfoxide, N,N-dimethylformamide (DM F), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are halogenated hydrocarbons as mentioned above.

It is also possible to use mixtures of the solvents mentioned.

Examples of suitable bases include metal-containing bases and nitrogen-containing bases. Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal carbonates such as lithium carbonate, sodium carbonate, potassium carbonate, magnesium carbonate, and calcium carbonate; alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; and furthermore organic bases, such as tertiary amines such as trimethylamine, triethylamine, diisopropylethylamine, tributylamine and N-methylpiperidine, pyridine, substituted pyridines such as collidinge, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal carbonates and nitrogen-containing bases as defined above; especially preferred triethylamine, pyridine or sodium carbonate.

The term base as used herein also includes mixtures of two or more, preferably two of the above compounds. Particular preference is given to the use of one base.

The bases are generally employed in catalytic amounts, however they can also be employed in equimolar amounts, in excess or, if appropriate, be used as solvent.

The bases are generally used in excess, more preferably with from 1 to 3 equivalents based on the acid chloride (II), and they may also be used as the solvent.

For the reaction, the acid chlorides (II), the compounds (III) and the base can be brought into contact in any way per se.

Accordingly the reaction partners and the base may be introduced into the reaction vessel and reacted separately, simultaneously or successively.

The reactants are generally employed in equimolar amounts. It might be advantageous using one of the reactants may be advantageous, for example with a view to as complete as possible a reaction of the other reactant.

The reaction can be carried out at atmospheric pressure, reduced pressure or under elevated pressure, if appropriate under an inert gas, continuously or batchwise.

The end of the reaction can easily be determined by the skilled worker by means of routine methods.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature.

If the intermediates and the end products are obtained as solid, purification can also be carried out by recrystallisation or digestion.

The acid chlorides (II) required for the preparation of phenylpyridines of formula (I) can be prepared in accordance with EP 726352 by chlorinating the corresponding free carboxylic acids or their alkali metal salts.

Suitable chlorinating agents are, for example, thionyl chloride, oxalyl chloride, phosphorus trichloride, phosphorus pentachloride, phosphorus oxychloride, phosgene, diphosgene or triphosgene.

More information for carrying out such chlorination reactions can be found in the following references, which are referred to by way of example: A. J. Meyers and M. E. Flanagan, Org. Synth. 71, 107 (1992); H. J. Scheifele Jr. and D. F. DeTar, Org. Synth. Coll. Vol. IV, page 34 (1963); G. H. Coleman et al., Org. Synth. Coll. Vol. III, page 712 (1955); H. Henecka in Houben-Weyl, Methoden der Organischen Chemie [Methods in Organic Chemistry], Vol. VIII, 4th Edition, Stuttgart 1952, page 463 et seq.

The free carboxylic acids or their alkali metal salts required for the preparation of the corresponding acid chlorides (II) can be prepared in accordance with EP 726352.

The compounds (III) required for the preparation of phenylpyridines of formula (I) are known and can be prepared as described in EP 726352.

Process B)

The phenylpyridines of formula (I) are also obtained by reacting (thio)phenols (IV) with alkylating agents (V) in the presence of a base:

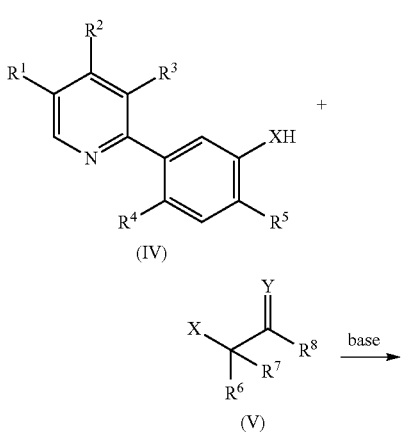

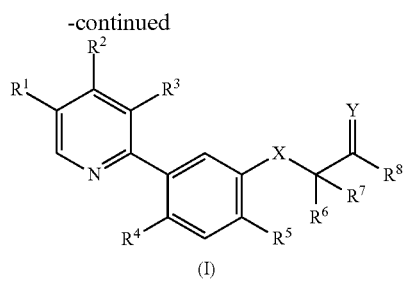

L is a nucleophilically displaceable leaving group such as halogen, $C_1$-$C_6$-alkoxy, $C_1$-$C_6$-alkylsulfonyl or $C_1$-$C_6$-haloalkylsulfonyl;

preferably Cl, Br, I or $OCH_3$;

more preferably Cl or Br.

The reaction of (thio)phenols (IV) with alkylating agents (V) is usually carried out at from −78° C. to the boiling point of the reaction mixture, preferably at from −20° C. to 100° C., particularly preferably at from 0° C. to 50° C., in an inert organic solvent in the presence of a base (e.g. WO 2011/137088).

The reaction may in principle be carried out in substance. However, preference is given to reacting the acid chlorides (II) with the compounds (III) in an organic solvent.

Suitable in principle are all solvents which are capable of dissolving the acid chlorides (II) and the compounds (III) at least partly and preferably fully under reaction conditions.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, tolene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tert-butyl methyl ketone, cyclohexanone; dipolar aprotic solvents such as sulfolane, dimethylsulfoxide, N,N-dimethylformamide (DM F), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are halogenated hydrocarbons as mentioned above.

It is also possible to use mixtures of the solvents mentioned.

Examples of suitable bases include metal-containing bases and nitrogen-containing bases. Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal carbonates such as lithium carbonate, sodium carbonate, potassium carbonate, magnesium carbonate, and calcium carbonate; alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; and furthermore organic bases, such as tertiary amines such as trimethylamine, triethylamine, diisopropylethylamine, tributylamine and N-methylpiperidine, pyridine, substituted pyridines such as collidinge, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal carbonates and nitrogen-containing bases as defined above; especially preferred triethylamine, pyridine or sodium carbonate.

The term base as used herein also includes mixtures of two or more, preferably two of the above compounds. Particular preference is given to the use of one base.

The bases are generally employed in catalytic amounts; however they can also be employed in equimolar amounts, in excess or, if appropriate, be used as solvent.

The bases are generally used in excess, more preferably with from 1 to 3 equivalents based on the acid chloride (II), and they may also be used as the solvent.

The end of the reaction can easily be determined by the skilled worker by means of routine methods.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature.

If the intermediates and the end products are obtained as solid, purification can also be carried out by recrystallisation or digestion.

The (thio)phenols (IV) required for the preparation of phenylpyridines of formula (I) are known from the literature (WO 95/02590) or they can be prepared in accordance with the literature cited.

The alkylating agents (V) required for the preparation of phenylpyridines of formula (I) are known from the literature (e.g. Lowell, Andrew N. et al, Tetrahedron, 6(30), 5573-5582; 2010, WO 2011/137088 or they can be prepared in accordance with the literature cited and/or are commercially available.

The acid chlorides of formula (II) are novel compounds and as shown above suitable intermediates for the preparation of the phenylpyridines of formula (I) according to the present invention.

Therefore the present invention also provides acid chlorides of formula (II)

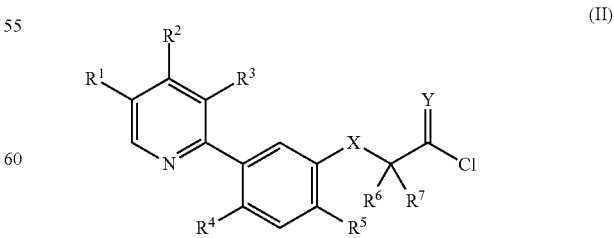

wherein the variables have the following meanings:
$R^1$ halogen, $C_1$-$C_4$-haloalkyl or $SO_2CH_3$;
$R^2$ H, $CH_3$ or $NH_2$;

R³ halogen;
R⁴ H or halogen;
R⁵ halogen or CN;
R⁶ H or CH₃;
R⁷ C₁-C₆-alkoxy, C₁-C₆-haloalkoxy, C₃-C₆-alkenyloxy, C₃-C₆-alkynyloxy, C₁-C₆-alkylthio, C₁-C₆-haloalkylthio, C₃-C₆-alkenylthio or C₃-C₆-alkynylthio;
X O or S; and
Y is O or S.

With respect to the variables, the particularly preferred embodiments of the intermediate compounds, the acid chlorides of formula (II) correspond, either independently of one another or in combination with one another, to those of the variables of R¹, R², R³, R⁴, R⁵, R⁶, R⁷ and Y of the phenylpyridines formula (I) as mentioned herein.

Particular preference is given to acid chlorides of formula (II.a) (correspond to acid chlorides of formula (II), wherein R¹ is CF₃, R² is H, R⁵ is Cl, R⁶ is H and Y is O),

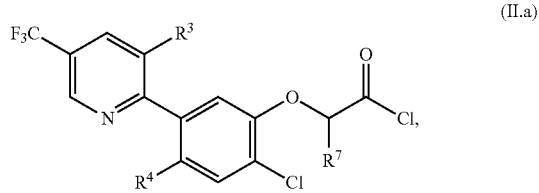

(II.a)

wherein the variables R³, R⁴ and R⁷ have the meanings, in particular the preferred meanings, as defined above.

Special preference is given to the acid chlorides of the formulae II.a.1 to II.a.8 of Table (II), where the definitions of the variables R³, R⁴ and R⁷ are of particular importance for the compounds according to the invention not only in combination with one another but in each case also on their own:

TABLE (II)

| No. | R³ | R⁴ | R⁷ |
|---|---|---|---|
| II.a.1 | F | H | OCH₃ |
| II.a.2 | F | H | OCH₂CH₃ |
| II.a.3 | F | F | OCH₃ |
| II.a.4 | F | F | OCH₂CH₃ |
| II.a.5 | Cl | H | OCH₃ |
| II.a.6 | Cl | H | OCH₂CH₃ |
| II.a.7 | Cl | F | OCH₃ |
| II.a.8 | Cl | F | OCH₂CH₃ |

Also preferred are the acid chlorides of formula (II.b), particularly preferred the acid chlorides of formulae (II.b.1) to (II.b.8), which differ from the corresponding acid chlorides of formulae (II.a) as well as (II.a.1) to (II.a.8) only in that R⁵ is CN:

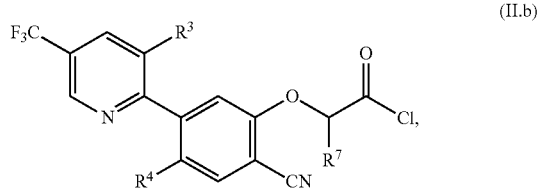

(II.b)

Also preferred are the acid chlorides of formula (II.c), particularly preferred the acid chlorides of formulae (II.c.1) to (II.c.8), which differ from the corresponding acid chlorides of formulae (II.a) as well as (II.a.1) to (II.a.8) only in that R⁵ is F:

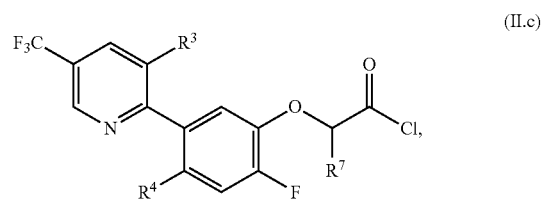

(II.c)

To widen the spectrum of action and to achieve synergistic effects, the phenylpyridines of formula (I) may be mixed with a large number of representatives of other herbicidal or growth-regulating active ingredient groups and then applied concomitantly. Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the phenylpyridines of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

In one embodiment of the present invention the compositions according to the present invention comprise at least one phenylpyridine of formula (I) (compound A) and at least one further active compound selected from herbicides B, preferably herbicides B of class b1) to b15), and safeners C (compound C).

In another embodiment of the present invention the compositions according to the present invention comprise at least one phenylpyridine of formula (I) and at least one further active compound B (herbicide B).

The further herbicidal compound B (component B) is preferably selected from the herbicides of class b1) to b15):
B) herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors, b5) bleacher herbicides;
b6) enolpyruvyl shikimate 3-phosphate synthase inhibitors (EPSP inhibitors);
b7) glutamine synthetase inhibitors;

b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives.

Preference is given to those compositions according to the present invention comprising at least one herbicide B selected from herbicides of class b2, b3, b4, b5, b6, B7, b9 b10 and b13.

Specific preference is given to those compositions according to the present invention which comprise at least one herbicide B selected from the herbicides of class b4, b6, b7, b9, b10 and b13.

Particular preference is given to those compositions according to the present invention which comprise at least one herbicide B selected from the herbicides of class b4, b6, b10 and b13.

Examples of herbicides B which can be used in combination with the phenylpyridines of formula (I) according to the present invention are:
b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6, 6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, clomazone, fenquintrione, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

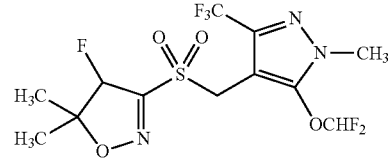

II.1

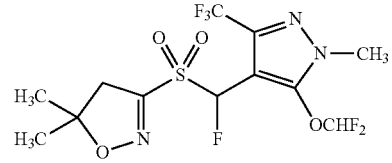

II.2

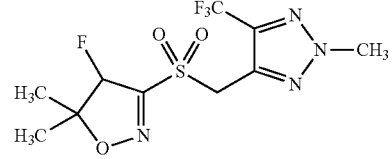

II.3

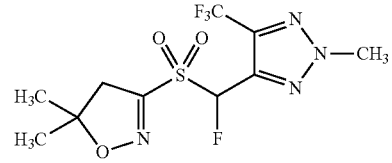

II.4

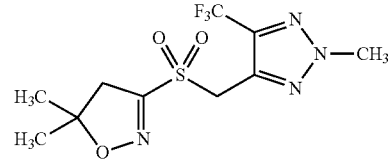

II.5

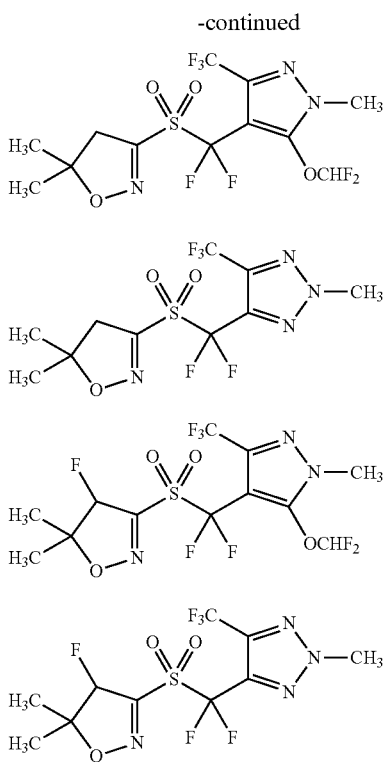

II.6
II.7
II.8
II.9 the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:

chlorthiamid, dichlobenil, flupoxam, isoxaben and 1-Cyclohexyl-5-pentafluorphenyloxy-1$^4$-[1,2,4,6]thiatriazin-3-ylamine;

b12) from the group of the decoupler herbicides:

dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of glyphosate are for example glyphosate-ammonium, glyphosate-diammonium, glyphosate-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Particularly preferred herbicides B are the herbicides B as defined above; in particular the herbicides B.1-B.189 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |

TABLE B-continued

Herbicide B

| | |
|---|---|
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | saflufenacil |
| B.93 | sulfentrazone |
| B.94 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate (CAS 353292-31-6) |
| B.95 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.96 | benzobicyclon |
| B.97 | clomazone |
| B.98 | diflufenican |
| B.99 | flurochloridone |
| B.100 | isoxaflutole |
| B.101 | mesotrione |
| B.102 | norflurazon |
| B.103 | picolinafen |
| B.104 | sulcotrione |
| B.105 | tefuryltrione |
| B.106 | tembotrione |
| B.107 | topramezone |
| B.108 | topramezone-sodium |
| B.109 | bicyclopyrone |
| B.110 | amitrole |
| B.111 | fluometuron |
| B.112 | fenquintrione |
| B.113 | glyphosate |
| B.114 | glyphosate-ammonium |
| B.115 | glyphosate-dimethylammonium |
| B.116 | glyphosate-isopropylammonium |
| B.117 | glyphosate-trimesium (sulfosate) |
| B.118 | glyphosate-potassium |
| B.119 | glufosinate |
| B.120 | glufosinate-ammonium |
| B.121 | glufosinate-P |
| B.122 | glufosinate-P-ammonium |
| B.123 | pendimethalin |
| B.124 | trifluralin |
| B.125 | acetochlor |
| B.126 | butachlor |
| B.127 | cafenstrole |
| B.128 | dimethenamid-P |
| B.129 | fentrazamide |
| B.130 | flufenacet |
| B.131 | mefenacet |
| B.132 | metazachlor |
| B.133 | metolachlor |
| B.134 | S-metolachlor |
| B.135 | pretilachlor |
| B.136 | fenoxasulfone |
| B.137 | isoxaben |
| B.138 | ipfencarbazone |
| B.139 | pyroxasulfone |
| B.140 | 2,4-D |
| B.141 | 2,4-D-isobutyl |
| B.142 | 2,4-D-dimethylammonium |
| B.143 | 2,4-D-N,N,N-trimethylethanolammonium |
| B.144 | aminopyralid |
| B.145 | aminopyralid-methyl |
| B.146 | aminopyralid-dimethyl-ammonium |
| B.147 | aminopyralid-tris(2-hydroxypropyl)ammonium |
| B.148 | clopyralid |
| B.149 | clopyralid-methyl |
| B.150 | clopyralid-olamine |
| B.151 | dicamba |
| B.152 | dicamba-butotyl |
| B.153 | dicamba-diglycolamine |
| B.154 | dicamba-dimethylammonium |
| B.155 | dicamba-diolamine |
| B.156 | dicamba-isopropylammonium |
| B.157 | dicamba-potassium |
| B.158 | dicamba-sodium |
| B.159 | dicamba-trolamine |
| B.160 | dicamba,N,N-bis-(3-aminopropyl)methylamine |
| B.161 | dicamba-diethylenetriamine |
| B.162 | fluroxypyr |
| B.163 | fluroxypyr-meptyl |
| B.164 | MCPA |
| B.165 | MCPA-2-ethylhexyl |
| B.166 | MCPA-dimethylammonium |
| B.167 | quinclorac |
| B.168 | quinclorac-dimethylammonium |
| B.169 | quinmerac |
| B.170 | quinmerac-dimethylammonium |
| B.171 | aminocyclopyrachlor |
| B.172 | aminocyclopyrachlor-potassium |

TABLE B-continued

| | Herbicide B |
|---|---|
| B.173 | aminocyclopyrachlor-methyl |
| B.174 | diflufenzopyr |
| B.175 | diflufenzopyr-sodium |
| B.176 | dymron |
| B.177 | indanofan |
| B.178 | indaziflam |
| B.179 | oxaziclomefone |
| B.180 | triaziflam |
| B.181 | II.1 |
| B.182 | II.2 |
| B.183 | II.3 |
| B.184 | II.4 |
| B.185 | II.5 |
| B.186 | II.6 |
| B.187 | II.7 |
| B.188 | II.8 |
| B.189 | II.9 |

Moreover, it may be useful to apply the phenylpyridines of formula (I) in combination with safeners. Safeners are chemical compounds which prevent or reduce damage on useful plants without having a major impact on the herbicidal action of the phenylpyridines of the formula (I) towards unwanted plants. They can be applied either before sowings (e.g. on seed treatments, shoots or seedlings) or in the pre-emergence application or post-emergence application of the useful plant.

The safeners and the phenylpyridines of formula (I) and optionally the herbicides B can be applied simultaneously or in succession.

In another embodiment of the present invention the compositions according to the present invention comprise at least one phenylpyridine of formula (I) and at least one safener C (component C).

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diary)-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |

TABLE C-continued

| | Safener C |
|---|---|
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | N-(2-Methoxybenzoyl)-4-[(methylaminocarbonyl)amino]benzenesulfonamide (CAS 129531-12-0) |

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as herbicidal active compounds B or component B at least four, preferably exactly four herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one, preferably exactly one compound of formula (I), preferably of formula (I.a), especially preferred the compound (I.a.200), and as component B at least one, preferably exactly one, herbicide B.

According to another preferred embodiment of the invention, the composition comprises as component A at least one, preferably exactly one compound of formula (I), preferably of formula (I.a), especially preferred the compound (I.a.200), and at least two, preferably exactly two, herbicides B different from each other.

According to another preferred embodiment of the invention, the composition comprises as component A at least one, preferably exactly one compound of formula (I), preferably of formula (I.a), especially preferred the compound (I.a.200), and at least three, preferably exactly three, herbicides B different from each other.

According to another preferred embodiment of the invention, the composition comprises as component A at least one, preferably exactly one compound of formula (I), preferably of formula (I.a), especially preferred the compound (I.a.200), and at least four, preferably exactly four, herbicides B different from each other.

According to another preferred embodiment of the invention, the composition comprises as component A at least one, preferably exactly one compound of formula (I), preferably of formula (I.a), especially preferred the compound (I.a.200), and as component C at least one, preferably exactly one, safener C.

According to another preferred embodiment of the invention, the composition comprises as component A at least one, preferably exactly one compound of formula (I), preferably of formula (I.a), especially preferred the compound (I.a.200), as component B at least one, preferably exactly one, herbicide B, and as component C at least one, preferably exactly one safener C.

According to another preferred embodiment of the invention, the composition comprises as component A at least one, preferably exactly one compound of formula (I), preferably of formula (I.a), especially preferred the compound (I.a.200), at least two, preferably exactly two herbicides B different from each other, and as component C at least one, preferably exactly one, safener C.

According to another preferred embodiment of the invention, the composition comprises as component A at least one, preferably exactly one compound of formula (I), preferably of formula (I.a), especially preferred the compound (I.a.200), at least three, preferably exactly three herbicides B different from each other, and as component C at least one, preferably exactly one, safener C.

According to another preferred embodiment of the invention, the composition comprises, in addition to a phenylpyridine of formula (I), especially an active compound from the group consisting of (I.a.200), (I.a.207), (I.a.214), (I.a.228) and (I.a.234), at least one and especially exactly one herbicidally active compound from group b4), in particular selected from the group consisting of flumioxazin, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione.

According to another preferred embodiment of the invention, the composition comprises, in addition to a phenylpyridine of formula (I), especially an active compound from the group consisting of (I.a.200), (I.a.207), (I.a.214), (I.a.228) and (I.a.234), at least one and especially exactly one herbicidally active compound from group b6), in particular selected from the group consisting of glyphosate, glyphosate-isopropylammonium and glyphosate-trimesium (sulfosate).

According to another preferred embodiment of the invention, the composition comprises, in addition to a phenylpyridine of formula (I), especially an active compound from the group consisting of (I.a.200), (I.a.207), (I.a.214), (I.a.228) and (I.a.234), at least one and especially exactly one herbicidally active compound from group b7), in particular selected from the group consisting of glufosinate, glufosinate-P and glufosinate-ammonium.

According to another preferred embodiment of the invention, the composition comprises, in addition to a phenylpyridine of formula (I), especially an active compound from the group consisting of (I.a.200), (I.a.207), (I.a.214), (I.a.228) and (I.a.234), at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a phenylpyridine of formula (I), especially an active compound from the group consisting of (I.a.200), (I.a.207), (I.a.214), (I.a.228) and (I.a.234), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a phenylpyridine of formula (I), especially an active compound from the group consisting of (I.a.200), (I.a.207), (I.a.214), (I.a.228) and (I.a.234), at least one and especially exactly one herbicidally active compound from group b13), in particular selected from the group consisting of 2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, fluroxypyr-meptyl, quinclorac and quinmerac.

Here and below, the term "binary compositions" includes compositions comprising one or more, for example 1, 2 or 3, active compounds of the formula (I) and either one or more, for example 1, 2 or 3, herbicides B or one or more safeners C.

Correspondingly, the term "ternary compositions" includes compositions comprising one or more, for example 1, 2 or 3, active compounds of the formula (I), one or more, for example 1, 2 or 3, herbicides B and one or more, for example 1, 2 or 3, safeners C.

In binary compositions comprising at least one compound of the formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one phenylpyridine of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given herein, in particular within the preferred limits.

Particularly preferred are the compositions mentioned below comprising the phenylpyridines of formula (I) as defined and the substance(s) as defined in the respective row of table 1;

especially preferred comprising as only herbicidal active compounds the phenylpyridines of formula (I) as defined and the substance(s) as defined in the respective row of table 1;

most preferably comprising as only active compounds the phenylpyridines of formula (I) as defined and the substance(s) as defined in the respective row of table 1.

Particularly preferred are compositions 1.1 to 1.3419, comprising the phenylpyridine of formula (I.a.200) and the substance(s) as defined in the respective row of table 1:

TABLE 1

(compositions 1.1 to 1.3419):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |

TABLE 1-continued (compositions 1.1 to 1.3419):

| comp. no. | herbicide B | safener C |
|---|---|---|
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |

TABLE 1-continued (compositions 1.1 to 1.3419):

| comp. no. | herbicide B | safener C |
|---|---|---|
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.1 | C.1 |
| 1.191 | B.2 | C.1 |
| 1.192 | B.3 | C.1 |
| 1.193 | B.4 | C.1 |
| 1.194 | B.5 | C.1 |
| 1.195 | B.6 | C.1 |
| 1.196 | B.7 | C.1 |
| 1.197 | B.8 | C.1 |
| 1.198 | B.9 | C.1 |
| 1.199 | B.10 | C.1 |
| 1.200 | B.11 | C.1 |
| 1.201 | B.12 | C.1 |
| 1.202 | B.13 | C.1 |
| 1.203 | B.14 | C.1 |
| 1.204 | B.15 | C.1 |
| 1.205 | B.16 | C.1 |
| 1.206 | B.17 | C.1 |
| 1.207 | B.18 | C.1 |
| 1.208 | B.19 | C.1 |
| 1.209 | B.20 | C.1 |
| 1.210 | B.21 | C.1 |
| 1.211 | B.22 | C.1 |
| 1.212 | B.23 | C.1 |
| 1.213 | B.24 | C.1 |
| 1.214 | B.25 | C.1 |
| 1.215 | B.26 | C.1 |
| 1.216 | B.27 | C.1 |
| 1.217 | B.28 | C.1 |
| 1.218 | B.29 | C.1 |
| 1.219 | B.30 | C.1 |
| 1.220 | B.31 | C.1 |
| 1.221 | B.32 | C.1 |
| 1.222 | B.33 | C.1 |
| 1.223 | B.34 | C.1 |
| 1.224 | B.35 | C.1 |
| 1.225 | B.36 | C.1 |
| 1.226 | B.37 | C.1 |
| 1.227 | B.38 | C.1 |
| 1.228 | B.39 | C.1 |
| 1.229 | B.40 | C.1 |
| 1.230 | B.41 | C.1 |
| 1.231 | B.42 | C.1 |
| 1.232 | B.43 | C.1 |
| 1.233 | B.44 | C.1 |
| 1.234 | B.45 | C.1 |
| 1.235 | B.46 | C.1 |
| 1.236 | B.47 | C.1 |

TABLE 1-continued (compositions 1.1 to 1.3419):

| comp. no. | herbicide B | safener C |
|---|---|---|
| 1.237 | B.48 | C.1 |
| 1.238 | B.49 | C.1 |
| 1.239 | B.50 | C.1 |
| 1.240 | B.51 | C.1 |
| 1.241 | B.52 | C.1 |
| 1.242 | B.53 | C.1 |
| 1.243 | B.54 | C.1 |
| 1.244 | B.55 | C.1 |
| 1.245 | B.56 | C.1 |
| 1.246 | B.57 | C.1 |
| 1.247 | B.58. | C.1 |
| 1.248 | B.59 | C.1 |
| 1.249 | B.60 | C.1 |
| 1.250 | B.61 | C.1 |
| 1.251 | B.62 | C.1 |
| 1.252 | B.63 | C.1 |
| 1.253 | B.64 | C.1 |
| 1.254 | B.65 | C.1 |
| 1.255 | B.66 | C.1 |
| 1.256 | B.67 | C.1 |
| 1.257 | B.68 | C.1 |
| 1.258 | B.69 | C.1 |
| 1.259 | B.70 | C.1 |
| 1.260 | B.71 | C.1 |
| 1.261 | B.72 | C.1 |
| 1.262 | B.73 | C.1 |
| 1.263 | B.74 | C.1 |
| 1.264 | B.75 | C.1 |
| 1.265 | B.76 | C.1 |
| 1.266 | B.77 | C.1 |
| 1.267 | B.78 | C.1 |
| 1.268 | B.79 | C.1 |
| 1.269 | B.80 | C.1 |
| 1.270 | B.81 | C.1 |
| 1.271 | B.82 | C.1 |
| 1.272 | B.83 | C.1 |
| 1.273 | B.84 | C.1 |
| 1.274 | B.85 | C.1 |
| 1.275 | B.86 | C.1 |
| 1.276 | B.87 | C.1 |
| 1.277 | B.88 | C.1 |
| 1.278 | B.89 | C.1 |
| 1.279 | B.90 | C.1 |
| 1.280 | B.91 | C.1 |
| 1.281 | B.92 | C.1 |
| 1.282 | B.93 | C.1 |
| 1.283 | B.94 | C.1 |
| 1.284 | B.95 | C.1 |
| 1.285 | B.96 | C.1 |
| 1.286 | B.97 | C.1 |
| 1.287 | B.98 | C.1 |
| 1.288 | B.99 | C.1 |
| 1.289 | B.100 | C.1 |
| 1.290 | B.101 | C.1 |
| 1.291 | B.102 | C.1 |
| 1.292 | B.103 | C.1 |
| 1.293 | B.104 | C.1 |
| 1.294 | B.105 | C.1 |
| 1.295 | B.106 | C.1 |
| 1.296 | B.107 | C.1 |
| 1.297 | B.108 | C.1 |
| 1.298 | B.109 | C.1 |
| 1.299 | B.110 | C.1 |
| 1.300 | B.111 | C.1 |
| 1.301 | B.112 | C.1 |
| 1.302 | B.113 | C.1 |
| 1.303 | B.114 | C.1 |
| 1.304 | B.115 | C.1 |
| 1.305 | B.116 | C.1 |
| 1.306 | B.117 | C.1 |
| 1.307 | B.118 | C.1 |
| 1.308 | B.119 | C.1 |
| 1.309 | B.120 | C.1 |
| 1.310 | B.121 | C.1 |
| 1.311 | B.122 | C.1 |
| 1.312 | B.123 | C.1 |
| 1.313 | B.124 | C.1 |
| 1.314 | B.125 | C.1 |
| 1.315 | B.126 | C.1 |
| 1.316 | B.127 | C.1 |
| 1.317 | B.128 | C.1 |
| 1.318 | B.129 | C.1 |
| 1.319 | B.130 | C.1 |
| 1.320 | B.131 | C.1 |
| 1.321 | B.132 | C.1 |
| 1.322 | B.133 | C.1 |
| 1.323 | B.134 | C.1 |
| 1.324 | B.135 | C.1 |
| 1.325 | B.136 | C.1 |
| 1.326 | B.137 | C.1 |
| 1.327 | B.138 | C.1 |
| 1.328 | B.139 | C.1 |
| 1.329 | B.140 | C.1 |
| 1.330 | B.141 | C.1 |
| 1.331 | B.142 | C.1 |
| 1.332 | B.143 | C.1 |
| 1.333 | B.144 | C.1 |
| 1.334 | B.145 | C.1 |
| 1.335 | B.146 | C.1 |
| 1.336 | B.147 | C.1 |
| 1.337 | B.148 | C.1 |
| 1.338 | B.149 | C.1 |
| 1.339 | B.150 | C.1 |
| 1.340 | B.151 | C.1 |
| 1.341 | B.152 | C.1 |
| 1.342 | B.153 | C.1 |
| 1.343 | B.154 | C.1 |
| 1.344 | B.155 | C.1 |
| 1.345 | B.156 | C.1 |
| 1.346 | B.157 | C.1 |
| 1.347 | B.158 | C.1 |
| 1.348 | B.159 | C.1 |
| 1.349 | B.160 | C.1 |
| 1.350 | B.161 | C.1 |
| 1.351 | B.162 | C.1 |
| 1.352 | B.163 | C.1 |
| 1.353 | B.164 | C.1 |
| 1.354 | B.165 | C.1 |
| 1.355 | B.166 | C.1 |
| 1.356 | B.167 | C.1 |
| 1.357 | B.168 | C.1 |
| 1.358 | B.169 | C.1 |
| 1.359 | B.170 | C.1 |
| 1.360 | B.171 | C.1 |
| 1.361 | B.172 | C.1 |
| 1.362 | B.173 | C.1 |
| 1.363 | B.174 | C.1 |
| 1.364 | B.175 | C.1 |
| 1.365 | B.176 | C.1 |
| 1.366 | B.177 | C.1 |
| 1.367 | B.178 | C.1 |
| 1.368 | B.179 | C.1 |
| 1.369 | B.180 | C.1 |
| 1.370 | B.181 | C.1 |
| 1.371 | B.182 | C.1 |
| 1.372 | B.183 | C.1 |
| 1.373 | B.184 | C.1 |
| 1.374 | B.185 | C.1 |
| 1.375 | B.186 | C.1 |
| 1.376 | B.187 | C.1 |
| 1.377 | B.188 | C.1 |
| 1.378 | B.189 | C.1 |
| 1.379 | B.1 | C.2 |
| 1.380 | B.2 | C.2 |
| 1.381 | B.3 | C.2 |
| 1.382 | B.4 | C.2 |
| 1.383 | B.5 | C.2 |
| 1.384 | B.6 | C.2 |
| 1.385 | B.7 | C.2 |
| 1.386 | B.8 | C.2 |
| 1.387 | B.9 | C.2 |
| 1.388 | B.10 | C.2 |

TABLE 1-continued (compositions 1.1 to 1.3419):

| comp. no. | herbicide B | safener C |
|---|---|---|
| 1.389 | B.11 | C.2 |
| 1.390 | B.12 | C.2 |
| 1.391 | B.13 | C.2 |
| 1.392 | B.14 | C.2 |
| 1.393 | B.15 | C.2 |
| 1.394 | B.16 | C.2 |
| 1.395 | B.17 | C.2 |
| 1.396 | B.18 | C.2 |
| 1.397 | B.19 | C.2 |
| 1.398 | B.20 | C.2 |
| 1.399 | B.21 | C.2 |
| 1.400 | B.22 | C.2 |
| 1.401 | B.23 | C.2 |
| 1.402 | B.24 | C.2 |
| 1.403 | B.25 | C.2 |
| 1.404 | B.26 | C.2 |
| 1.405 | B.27 | C.2 |
| 1.406 | B.28 | C.2 |
| 1.407 | B.29 | C.2 |
| 1.408 | B.30 | C.2 |
| 1.409 | B.31 | C.2 |
| 1.410 | B.32 | C.2 |
| 1.411 | B.33 | C.2 |
| 1.412 | B.34 | C.2 |
| 1.413 | B.35 | C.2 |
| 1.414 | B.36 | C.2 |
| 1.415 | B.37 | C.2 |
| 1.416 | B.38 | C.2 |
| 1.417 | B.39 | C.2 |
| 1.418 | B.40 | C.2 |
| 1.419 | B.41 | C.2 |
| 1.420 | B.42 | C.2 |
| 1.421 | B.43 | C.2 |
| 1.422 | B.44 | C.2 |
| 1.423 | B.45 | C.2 |
| 1.424 | B.46 | C.2 |
| 1.425 | B.47 | C.2 |
| 1.426 | B.48 | C.2 |
| 1.427 | B.49 | C.2 |
| 1.428 | B.50 | C.2 |
| 1.429 | B.51 | C.2 |
| 1.430 | B.52 | C.2 |
| 1.431 | B.53 | C.2 |
| 1.432 | B.54 | C.2 |
| 1.433 | B.55 | C.2 |
| 1.434 | B.56 | C.2 |
| 1.435 | B.57 | C.2 |
| 1.436 | B.58. | C.2 |
| 1.437 | B.59 | C.2 |
| 1.438 | B.60 | C.2 |
| 1.439 | B.61 | C.2 |
| 1.440 | B.62 | C.2 |
| 1.441 | B.63 | C.2 |
| 1.442 | B.64 | C.2 |
| 1.443 | B.65 | C.2 |
| 1.444 | B.66 | C.2 |
| 1.445 | B.67 | C.2 |
| 1.446 | B.68 | C.2 |
| 1.447 | B.69 | C.2 |
| 1.448 | B.70 | C.2 |
| 1.449 | B.71 | C.2 |
| 1.450 | B.72 | C.2 |
| 1.451 | B.73 | C.2 |
| 1.452 | B.74 | C.2 |
| 1.453 | B.75 | C.2 |
| 1.454 | B.76 | C.2 |
| 1.455 | B.77 | C.2 |
| 1.456 | B.78 | C.2 |
| 1.457 | B.79 | C.2 |
| 1.458 | B.80 | C.2 |
| 1.459 | B.81 | C.2 |
| 1.460 | B.82 | C.2 |
| 1.461 | B.83 | C.2 |
| 1.462 | B.84 | C.2 |
| 1.463 | B.85 | C.2 |
| 1.464 | B.86 | C.2 |
| 1.465 | B.87 | C.2 |
| 1.466 | B.88 | C.2 |
| 1.467 | B.89 | C.2 |
| 1.468 | B.90 | C.2 |
| 1.469 | B.91 | C.2 |
| 1.470 | B.92 | C.2 |
| 1.471 | B.93 | C.2 |
| 1.472 | B.94 | C.2 |
| 1.473 | B.95 | C.2 |
| 1.474 | B.96 | C.2 |
| 1.475 | B.97 | C.2 |
| 1.476 | B.98 | C.2 |
| 1.477 | B.99 | C.2 |
| 1.478 | B.100 | C.2 |
| 1.479 | B.101 | C.2 |
| 1.480 | B.102 | C.2 |
| 1.481 | B.103 | C.2 |
| 1.482 | B.104 | C.2 |
| 1.483 | B.105 | C.2 |
| 1.484 | B.106 | C.2 |
| 1.485 | B.107 | C.2 |
| 1.486 | B.108 | C.2 |
| 1.487 | B.109 | C.2 |
| 1.488 | B.110 | C.2 |
| 1.489 | B.111 | C.2 |
| 1.490 | B.112 | C.2 |
| 1.491 | B.113 | C.2 |
| 1.492 | B.114 | C.2 |
| 1.493 | B.115 | C.2 |
| 1.494 | B.116 | C.2 |
| 1.495 | B.117 | C.2 |
| 1.496 | B.118 | C.2 |
| 1.497 | B.119 | C.2 |
| 1.498 | B.120 | C.2 |
| 1.499 | B.121 | C.2 |
| 1.500 | B.122 | C.2 |
| 1.501 | B.123 | C.2 |
| 1.502 | B.124 | C.2 |
| 1.503 | B.125 | C.2 |
| 1.504 | B.126 | C.2 |
| 1.505 | B.127 | C.2 |
| 1.506 | B.128 | C.2 |
| 1.507 | B.129 | C.2 |
| 1.508 | B.130 | C.2 |
| 1.509 | B.131 | C.2 |
| 1.510 | B.132 | C.2 |
| 1.511 | B.133 | C.2 |
| 1.512 | B.134 | C.2 |
| 1.513 | B.135 | C.2 |
| 1.514 | B.136 | C.2 |
| 1.515 | B.137 | C.2 |
| 1.516 | B.138 | C.2 |
| 1.517 | B.139 | C.2 |
| 1.518 | B.140 | C.2 |
| 1.519 | B.141 | C.2 |
| 1.520 | B.142 | C.2 |
| 1.521 | B.143 | C.2 |
| 1.522 | B.144 | C.2 |
| 1.523 | B.145 | C.2 |
| 1.524 | B.146 | C.2 |
| 1.525 | B.147 | C.2 |
| 1.526 | B.148 | C.2 |
| 1.527 | B.149 | C.2 |
| 1.528 | B.150 | C.2 |
| 1.529 | B.151 | C.2 |
| 1.530 | B.152 | C.2 |
| 1.531 | B.153 | C.2 |
| 1.532 | B.154 | C.2 |
| 1.533 | B.155 | C.2 |
| 1.534 | B.156 | C.2 |
| 1.535 | B.157 | C.2 |
| 1.536 | B.158 | C.2 |
| 1.537 | B.159 | C.2 |
| 1.538 | B.160 | C.2 |
| 1.539 | B.161 | C.2 |
| 1.540 | B.162 | C.2 |

TABLE 1-continued (compositions 1.1 to 1.3419):

| comp. no. | herbicide B | safener C |
|---|---|---|
| 1.541 | B.163 | C.2 |
| 1.542 | B.164 | C.2 |
| 1.543 | B.165 | C.2 |
| 1.544 | B.166 | C.2 |
| 1.545 | B.167 | C.2 |
| 1.546 | B.168 | C.2 |
| 1.547 | B.169 | C.2 |
| 1.548 | B.170 | C.2 |
| 1.549 | B.171 | C.2 |
| 1.550 | B.172 | C.2 |
| 1.551 | B.173 | C.2 |
| 1.552 | B.174 | C.2 |
| 1.553 | B.175 | C.2 |
| 1.554 | B.176 | C.2 |
| 1.555 | B.177 | C.2 |
| 1.556 | B.178 | C.2 |
| 1.557 | B.179 | C.2 |
| 1.558 | B.180 | C.2 |
| 1.559 | B.181 | C.2 |
| 1.560 | B.182 | C.2 |
| 1.561 | B.183 | C.2 |
| 1.562 | B.184 | C.2 |
| 1.563 | B.185 | C.2 |
| 1.564 | B.186 | C.2 |
| 1.565 | B.187 | C.2 |
| 1.566 | B.188 | C.2 |
| 1.567 | B.189 | C.2 |
| 1.568 | B.1 | C.3 |
| 1.569 | B.2 | C.3 |
| 1.570 | B.3 | C.3 |
| 1.571 | B.4 | C.3 |
| 1.572 | B.5 | C.3 |
| 1.573 | B.6 | C.3 |
| 1.574 | B.7 | C.3 |
| 1.575 | B.8 | C.3 |
| 1.576 | B.9 | C.3 |
| 1.577 | B.10 | C.3 |
| 1.578 | B.11 | C.3 |
| 1.579 | B.12 | C.3 |
| 1.580 | B.13 | C.3 |
| 1.581 | B.14 | C.3 |
| 1.582 | B.15 | C.3 |
| 1.583 | B.16 | C.3 |
| 1.584 | B.17 | C.3 |
| 1.585 | B.18 | C.3 |
| 1.586 | B.19 | C.3 |
| 1.587 | B.20 | C.3 |
| 1.588 | B.21 | C.3 |
| 1.589 | B.22 | C.3 |
| 1.590 | B.23 | C.3 |
| 1.591 | B.24 | C.3 |
| 1.592 | B.25 | C.3 |
| 1.593 | B.26 | C.3 |
| 1.594 | B.27 | C.3 |
| 1.595 | B.28 | C.3 |
| 1.596 | B.29 | C.3 |
| 1.597 | B.30 | C.3 |
| 1.598 | B.31 | C.3 |
| 1.599 | B.32 | C.3 |
| 1.600 | B.33 | C.3 |
| 1.601 | B.34 | C.3 |
| 1.602 | B.35 | C.3 |
| 1.603 | B.36 | C.3 |
| 1.604 | B.37 | C.3 |
| 1.605 | B.38 | C.3 |
| 1.606 | B.39 | C.3 |
| 1.607 | B.40 | C.3 |
| 1.608 | B.41 | C.3 |
| 1.609 | B.42 | C.3 |
| 1.610 | B.43 | C.3 |
| 1.611 | B.44 | C.3 |
| 1.612 | B.45 | C.3 |
| 1.613 | B.46 | C.3 |
| 1.614 | B.47 | C.3 |
| 1.615 | B.48 | C.3 |
| 1.616 | B.49 | C.3 |
| 1.617 | B.50 | C.3 |
| 1.618 | B.51 | C.3 |
| 1.619 | B.52 | C.3 |
| 1.620 | B.53 | C.3 |
| 1.621 | B.54 | C.3 |
| 1.622 | B.55 | C.3 |
| 1.623 | B.56 | C.3 |
| 1.624 | B.57 | C.3 |
| 1.625 | B.58. | C.3 |
| 1.626 | B.59 | C.3 |
| 1.627 | B.60 | C.3 |
| 1.628 | B.61 | C.3 |
| 1.629 | B.62 | C.3 |
| 1.630 | B.63 | C.3 |
| 1.631 | B.64 | C.3 |
| 1.632 | B.65 | C.3 |
| 1.633 | B.66 | C.3 |
| 1.634 | B.67 | C.3 |
| 1.635 | B.68 | C.3 |
| 1.636 | B.69 | C.3 |
| 1.637 | B.70 | C.3 |
| 1.638 | B.71 | C.3 |
| 1.639 | B.72 | C.3 |
| 1.640 | B.73 | C.3 |
| 1.641 | B.74 | C.3 |
| 1.642 | B.75 | C.3 |
| 1.643 | B.76 | C.3 |
| 1.644 | B.77 | C.3 |
| 1.645 | B.78 | C.3 |
| 1.646 | B.79 | C.3 |
| 1.647 | B.80 | C.3 |
| 1.648 | B.81 | C.3 |
| 1.649 | B.82 | C.3 |
| 1.650 | B.83 | C.3 |
| 1.651 | B.84 | C.3 |
| 1.652 | B.85 | C.3 |
| 1.653 | B.86 | C.3 |
| 1.654 | B.87 | C.3 |
| 1.655 | B.88 | C.3 |
| 1.656 | B.89 | C.3 |
| 1.657 | B.90 | C.3 |
| 1.658 | B.91 | C.3 |
| 1.659 | B.92 | C.3 |
| 1.660 | B.93 | C.3 |
| 1.661 | B.94 | C.3 |
| 1.662 | B.95 | C.3 |
| 1.663 | B.96 | C.3 |
| 1.664 | B.97 | C.3 |
| 1.665 | B.98 | C.3 |
| 1.666 | B.99 | C.3 |
| 1.667 | B.100 | C.3 |
| 1.668 | B.101 | C.3 |
| 1.669 | B.102 | C.3 |
| 1.670 | B.103 | C.3 |
| 1.671 | B.104 | C.3 |
| 1.672 | B.105 | C.3 |
| 1.673 | B.106 | C.3 |
| 1.674 | B.107 | C.3 |
| 1.675 | B.108 | C.3 |
| 1.676 | B.109 | C.3 |
| 1.677 | B.110 | C.3 |
| 1.678 | B.111 | C.3 |
| 1.679 | B.112 | C.3 |
| 1.680 | B.113 | C.3 |
| 1.681 | B.114 | C.3 |
| 1.682 | B.115 | C.3 |
| 1.683 | B.116 | C.3 |
| 1.684 | B.117 | C.3 |
| 1.685 | B.118 | C.3 |
| 1.686 | B.119 | C.3 |
| 1.687 | B.120 | C.3 |
| 1.688 | B.121 | C.3 |
| 1.689 | B.122 | C.3 |
| 1.690 | B.123 | C.3 |
| 1.691 | B.124 | C.3 |
| 1.692 | B.125 | C.3 |

TABLE 1-continued (compositions 1.1 to 1.3419):

| comp. no. | herbicide B | safener C |
|---|---|---|
| 1.693 | B.126 | C.3 |
| 1.694 | B.127 | C.3 |
| 1.695 | B.128 | C.3 |
| 1.696 | B.129 | C.3 |
| 1.697 | B.130 | C.3 |
| 1.698 | B.131 | C.3 |
| 1.699 | B.132 | C.3 |
| 1.700 | B.133 | C.3 |
| 1.701 | B.134 | C.3 |
| 1.702 | B.135 | C.3 |
| 1.703 | B.136 | C.3 |
| 1.704 | B.137 | C.3 |
| 1.705 | B.138 | C.3 |
| 1.706 | B.139 | C.3 |
| 1.707 | B.140 | C.3 |
| 1.708 | B.141 | C.3 |
| 1.709 | B.142 | C.3 |
| 1.710 | B.143 | C.3 |
| 1.711 | B.144 | C.3 |
| 1.712 | B.145 | C.3 |
| 1.713 | B.146 | C.3 |
| 1.714 | B.147 | C.3 |
| 1.715 | B.148 | C.3 |
| 1.716 | B.149 | C.3 |
| 1.717 | B.150 | C.3 |
| 1.718 | B.151 | C.3 |
| 1.719 | B.152 | C.3 |
| 1.720 | B.153 | C.3 |
| 1.721 | B.154 | C.3 |
| 1.722 | B.155 | C.3 |
| 1.723 | B.156 | C.3 |
| 1.724 | B.157 | C.3 |
| 1.725 | B.158 | C.3 |
| 1.726 | B.159 | C.3 |
| 1.727 | B.160 | C.3 |
| 1.728 | B.161 | C.3 |
| 1.729 | B.162 | C.3 |
| 1.730 | B.163 | C.3 |
| 1.731 | B.164 | C.3 |
| 1.732 | B.165 | C.3 |
| 1.733 | B.166 | C.3 |
| 1.734 | B.167 | C.3 |
| 1.735 | B.168 | C.3 |
| 1.736 | B.169 | C.3 |
| 1.737 | B.170 | C.3 |
| 1.738 | B.171 | C.3 |
| 1.739 | B.172 | C.3 |
| 1.740 | B.173 | C.3 |
| 1.741 | B.174 | C.3 |
| 1.742 | B.175 | C.3 |
| 1.743 | B.176 | C.3 |
| 1.744 | B.177 | C.3 |
| 1.745 | B.178 | C.3 |
| 1.746 | B.179 | C.3 |
| 1.747 | B.180 | C.3 |
| 1.748 | B.181 | C.3 |
| 1.749 | B.182 | C.3 |
| 1.750 | B.183 | C.3 |
| 1.751 | B.184 | C.3 |
| 1.752 | B.185 | C.3 |
| 1.753 | B.186 | C.3 |
| 1.754 | B.187 | C.3 |
| 1.755 | B.188 | C.3 |
| 1.756 | B.189 | C.3 |
| 1.757 | B.1 | C.4 |
| 1.758 | B.2 | C.4 |
| 1.759 | B.3 | C.4 |
| 1.760 | B.4 | C.4 |
| 1.761 | B.5 | C.4 |
| 1.762 | B.6 | C.4 |
| 1.763 | B.7 | C.4 |
| 1.764 | B.8 | C.4 |
| 1.765 | B.9 | C.4 |
| 1.766 | B.10 | C.4 |
| 1.767 | B.11 | C.4 |
| 1.768 | B.12 | C.4 |
| 1.769 | B.13 | C.4 |
| 1.770 | B.14 | C.4 |
| 1.771 | B.15 | C.4 |
| 1.772 | B.16 | C.4 |
| 1.773 | B.17 | C.4 |
| 1.774 | B.18 | C.4 |
| 1.775 | B.19 | C.4 |
| 1.776 | B.20 | C.4 |
| 1.777 | B.21 | C.4 |
| 1.778 | B.22 | C.4 |
| 1.779 | B.23 | C.4 |
| 1.780 | B.24 | C.4 |
| 1.781 | B.25 | C.4 |
| 1.782 | B.26 | C.4 |
| 1.783 | B.27 | C.4 |
| 1.784 | B.28 | C.4 |
| 1.785 | B.29 | C.4 |
| 1.786 | B.30 | C.4 |
| 1.787 | B.31 | C.4 |
| 1.788 | B.32 | C.4 |
| 1.789 | B.33 | C.4 |
| 1.790 | B.34 | C.4 |
| 1.791 | B.35 | C.4 |
| 1.792 | B.36 | C.4 |
| 1.793 | B.37 | C.4 |
| 1.794 | B.38 | C.4 |
| 1.795 | B.39 | C.4 |
| 1.796 | B.40 | C.4 |
| 1.797 | B.41 | C.4 |
| 1.798 | B.42 | C.4 |
| 1.799 | B.43 | C.4 |
| 1.800 | B.44 | C.4 |
| 1.801 | B.45 | C.4 |
| 1.802 | B.46 | C.4 |
| 1.803 | B.47 | C.4 |
| 1.804 | B.48 | C.4 |
| 1.805 | B.49 | C.4 |
| 1.806 | B.50 | C.4 |
| 1.807 | B.51 | C.4 |
| 1.808 | B.52 | C.4 |
| 1.809 | B.53 | C.4 |
| 1.810 | B.54 | C.4 |
| 1.811 | B.55 | C.4 |
| 1.812 | B.56 | C.4 |
| 1.813 | B.57 | C.4 |
| 1.814 | B.58 | C.4 |
| 1.815 | B.59 | C.4 |
| 1.816 | B.60 | C.4 |
| 1.817 | B.61 | C.4 |
| 1.818 | B.62 | C.4 |
| 1.819 | B.63 | C.4 |
| 1.820 | B.64 | C.4 |
| 1.821 | B.65 | C.4 |
| 1.822 | B.66 | C.4 |
| 1.823 | B.67 | C.4 |
| 1.824 | B.68 | C.4 |
| 1.825 | B.69 | C.4 |
| 1.826 | B.70 | C.4 |
| 1.827 | B.71 | C.4 |
| 1.828 | B.72 | C.4 |
| 1.829 | B.73 | C.4 |
| 1.830 | B.74 | C.4 |
| 1.831 | B.75 | C.4 |
| 1.832 | B.76 | C.4 |
| 1.833 | B.77 | C.4 |
| 1.834 | B.78 | C.4 |
| 1.835 | B.79 | C.4 |
| 1.836 | B.80 | C.4 |
| 1.837 | B.81 | C.4 |
| 1.838 | B.82 | C.4 |
| 1.839 | B.83 | C.4 |
| 1.840 | B.84 | C.4 |
| 1.841 | B.85 | C.4 |
| 1.842 | B.86 | C.4 |
| 1.843 | B.87 | C.4 |
| 1.844 | B.88 | C.4 |

TABLE 1-continued (compositions 1.1 to 1.3419):

| comp. no. | herbicide B | safener C |
|---|---|---|
| 1.845 | B.89 | C.4 |
| 1.846 | B.90 | C.4 |
| 1.847 | B.91 | C.4 |
| 1.848 | B.92 | C.4 |
| 1.849 | B.93 | C.4 |
| 1.850 | B.94 | C.4 |
| 1.851 | B.95 | C.4 |
| 1.852 | B.96 | C.4 |
| 1.853 | B.97 | C.4 |
| 1.854 | B.98 | C.4 |
| 1.855 | B.99 | C.4 |
| 1.856 | B.100 | C.4 |
| 1.857 | B.101 | C.4 |
| 1.858 | B.102 | C.4 |
| 1.859 | B.103 | C.4 |
| 1.860 | B.104 | C.4 |
| 1.861 | B.105 | C.4 |
| 1.862 | B.106 | C.4 |
| 1.863 | B.107 | C.4 |
| 1.864 | B.108 | C.4 |
| 1.865 | B.109 | C.4 |
| 1.866 | B.110 | C.4 |
| 1.867 | B.111 | C.4 |
| 1.868 | B.112 | C.4 |
| 1.869 | B.113 | C.4 |
| 1.870 | B.114 | C.4 |
| 1.871 | B.115 | C.4 |
| 1.872 | B.116 | C.4 |
| 1.873 | B.117 | C.4 |
| 1.874 | B.118 | C.4 |
| 1.875 | B.119 | C.4 |
| 1.876 | B.120 | C.4 |
| 1.877 | B.121 | C.4 |
| 1.878 | B.122 | C.4 |
| 1.879 | B.123 | C.4 |
| 1.880 | B.124 | C.4 |
| 1.881 | B.125 | C.4 |
| 1.882 | B.126 | C.4 |
| 1.883 | B.127 | C.4 |
| 1.884 | B.128 | C.4 |
| 1.885 | B.129 | C.4 |
| 1.886 | B.130 | C.4 |
| 1.887 | B.131 | C.4 |
| 1.888 | B.132 | C.4 |
| 1.889 | B.133 | C.4 |
| 1.890 | B.134 | C.4 |
| 1.891 | B.135 | C.4 |
| 1.892 | B.136 | C.4 |
| 1.893 | B.137 | C.4 |
| 1.894 | B.138 | C.4 |
| 1.895 | B.139 | C.4 |
| 1.896 | B.140 | C.4 |
| 1.897 | B.141 | C.4 |
| 1.898 | B.142 | C.4 |
| 1.899 | B.143 | C.4 |
| 1.900 | B.144 | C.4 |
| 1.901 | B.145 | C.4 |
| 1.902 | B.146 | C.4 |
| 1.903 | B.147 | C.4 |
| 1.904 | B.148 | C.4 |
| 1.905 | B.149 | C.4 |
| 1.906 | B.150 | C.4 |
| 1.907 | B.151 | C.4 |
| 1.908 | B.152 | C.4 |
| 1.909 | B.153 | C.4 |
| 1.910 | B.154 | C.4 |
| 1.911 | B.155 | C.4 |
| 1.912 | B.156 | C.4 |
| 1.913 | B.157 | C.4 |
| 1.914 | B.158 | C.4 |
| 1.915 | B.159 | C.4 |
| 1.916 | B.160 | C.4 |
| 1.917 | B.161 | C.4 |
| 1.918 | B.162 | C.4 |
| 1.919 | B.163 | C.4 |
| 1.920 | B.164 | C.4 |
| 1.921 | B.165 | C.4 |
| 1.922 | B.166 | C.4 |
| 1.923 | B.167 | C.4 |
| 1.924 | B.168 | C.4 |
| 1.925 | B.169 | C.4 |
| 1.926 | B.170 | C.4 |
| 1.927 | B.171 | C.4 |
| 1.928 | B.172 | C.4 |
| 1.929 | B.173 | C.4 |
| 1.930 | B.174 | C.4 |
| 1.931 | B.175 | C.4 |
| 1.932 | B.176 | C.4 |
| 1.933 | B.177 | C.4 |
| 1.934 | B.178 | C.4 |
| 1.935 | B.179 | C.4 |
| 1.936 | B.180 | C.4 |
| 1.937 | B.181 | C.4 |
| 1.938 | B.182 | C.4 |
| 1.939 | B.183 | C.4 |
| 1.940 | B.184 | C.4 |
| 1.941 | B.185 | C.4 |
| 1.942 | B.186 | C.4 |
| 1.943 | B.187 | C.4 |
| 1.944 | B.188 | C.4 |
| 1.945 | B.189 | C.4 |
| 1.946 | B.1 | C.5 |
| 1.947 | B.2 | C.5 |
| 1.948 | B.3 | C.5 |
| 1.949 | B.4 | C.5 |
| 1.950 | B.5 | C.5 |
| 1.951 | B.6 | C.5 |
| 1.952 | B.7 | C.5 |
| 1.953 | B.8 | C.5 |
| 1.954 | B.9 | C.5 |
| 1.955 | B.10 | C.5 |
| 1.956 | B.11 | C.5 |
| 1.957 | B.12 | C.5 |
| 1.958 | B.13 | C.5 |
| 1.959 | B.14 | C.5 |
| 1.960 | B.15 | C.5 |
| 1.961 | B.16 | C.5 |
| 1.962 | B.17 | C.5 |
| 1.963 | B.18 | C.5 |
| 1.964 | B.19 | C.5 |
| 1.965 | B.20 | C.5 |
| 1.966 | B.21 | C.5 |
| 1.967 | B.22 | C.5 |
| 1.968 | B.23 | C.5 |
| 1.969 | B.24 | C.5 |
| 1.970 | B.25 | C.5 |
| 1.971 | B.26 | C.5 |
| 1.972 | B.27 | C.5 |
| 1.973 | B.28 | C.5 |
| 1.974 | B.29 | C.5 |
| 1.975 | B.30 | C.5 |
| 1.976 | B.31 | C.5 |
| 1.977 | B.32 | C.5 |
| 1.978 | B.33 | C.5 |
| 1.979 | B.34 | C.5 |
| 1.980 | B.35 | C.5 |
| 1.981 | B.36 | C.5 |
| 1.982 | B.37 | C.5 |
| 1.983 | B.38 | C.5 |
| 1.984 | B.39 | C.5 |
| 1.985 | B.40 | C.5 |
| 1.986 | B.41 | C.5 |
| 1.987 | B.42 | C.5 |
| 1.988 | B.43 | C.5 |
| 1.989 | B.44 | C.5 |
| 1.990 | B.45 | C.5 |
| 1.991 | B.46 | C.5 |
| 1.992 | B.47 | C.5 |
| 1.993 | B.48 | C.5 |
| 1.994 | B.49 | C.5 |
| 1.995 | B.50 | C.5 |
| 1.996 | B.51 | C.5 |

TABLE 1-continued (compositions 1.1 to 1.3419):

| comp. no. | herbicide B | safener C |
|---|---|---|
| 1.997 | B.52 | C.5 |
| 1.998 | B.53 | C.5 |
| 1.999 | B.54 | C.5 |
| 1.1000 | B.55 | C.5 |
| 1.1001 | B.56 | C.5 |
| 1.1002 | B.57 | C.5 |
| 1.1003 | B.58. | C.5 |
| 1.1004 | B.59 | C.5 |
| 1.1005 | B.60 | C.5 |
| 1.1006 | B.61 | C.5 |
| 1.1007 | B.62 | C.5 |
| 1.1008 | B.63 | C.5 |
| 1.1009 | B.64 | C.5 |
| 1.1010 | B.65 | C.5 |
| 1.1011 | B.66 | C.5 |
| 1.1012 | B.67 | C.5 |
| 1.1013 | B.68 | C.5 |
| 1.1014 | B.69 | C.5 |
| 1.1015 | B.70 | C.5 |
| 1.1016 | B.71 | C.5 |
| 1.1017 | B.72 | C.5 |
| 1.1018 | B.73 | C.5 |
| 1.1019 | B.74 | C.5 |
| 1.1020 | B.75 | C.5 |
| 1.1021 | B.76 | C.5 |
| 1.1022 | B.77 | C.5 |
| 1.1023 | B.78 | C.5 |
| 1.1024 | B.79 | C.5 |
| 1.1025 | B.80 | C.5 |
| 1.1026 | B.81 | C.5 |
| 1.1027 | B.82 | C.5 |
| 1.1028 | B.83 | C.5 |
| 1.1029 | B.84 | C.5 |
| 1.1030 | B.85 | C.5 |
| 1.1031 | B.86 | C.5 |
| 1.1032 | B.87 | C.5 |
| 1.1033 | B.88 | C.5 |
| 1.1034 | B.89 | C.5 |
| 1.1035 | B.90 | C.5 |
| 1.1036 | B.91 | C.5 |
| 1.1037 | B.92 | C.5 |
| 1.1038 | B.93 | C.5 |
| 1.1039 | B.94 | C.5 |
| 1.1040 | B.95 | C.5 |
| 1.1041 | B.96 | C.5 |
| 1.1042 | B.97 | C.5 |
| 1.1043 | B.98 | C.5 |
| 1.1044 | B.99 | C.5 |
| 1.1045 | B.100 | C.5 |
| 1.1046 | B.101 | C.5 |
| 1.1047 | B.102 | C.5 |
| 1.1048 | B.103 | C.5 |
| 1.1049 | B.104 | C.5 |
| 1.1050 | B.105 | C.5 |
| 1.1051 | B.106 | C.5 |
| 1.1052 | B.107 | C.5 |
| 1.1053 | B.108 | C.5 |
| 1.1054 | B.109 | C.5 |
| 1.1055 | B.110 | C.5 |
| 1.1056 | B.111 | C.5 |
| 1.1057 | B.112 | C.5 |
| 1.1058 | B.113 | C.5 |
| 1.1059 | B.114 | C.5 |
| 1.1060 | B.115 | C.5 |
| 1.1061 | B.116 | C.5 |
| 1.1062 | B.117 | C.5 |
| 1.1063 | B.118 | C.5 |
| 1.1064 | B.119 | C.5 |
| 1.1065 | B.120 | C.5 |
| 1.1066 | B.121 | C.5 |
| 1.1067 | B.122 | C.5 |
| 1.1068 | B.123 | C.5 |
| 1.1069 | B.124 | C.5 |
| 1.1070 | B.125 | C.5 |
| 1.1071 | B.126 | C.5 |
| 1.1072 | B.127 | C.5 |
| 1.1073 | B.128 | C.5 |
| 1.1074 | B.129 | C.5 |
| 1.1075 | B.130 | C.5 |
| 1.1076 | B.131 | C.5 |
| 1.1077 | B.132 | C.5 |
| 1.1078 | B.133 | C.5 |
| 1.1079 | B.134 | C.5 |
| 1.1080 | B.135 | C.5 |
| 1.1081 | B.136 | C.5 |
| 1.1082 | B.137 | C.5 |
| 1.1083 | B.138 | C.5 |
| 1.1084 | B.139 | C.5 |
| 1.1085 | B.140 | C.5 |
| 1.1086 | B.141 | C.5 |
| 1.1087 | B.142 | C.5 |
| 1.1088 | B.143 | C.5 |
| 1.1089 | B.144 | C.5 |
| 1.1090 | B.145 | C.5 |
| 1.1091 | B.146 | C.5 |
| 1.1092 | B.147 | C.5 |
| 1.1093 | B.148 | C.5 |
| 1.1094 | B.149 | C.5 |
| 1.1095 | B.150 | C.5 |
| 1.1096 | B.151 | C.5 |
| 1.1097 | B.152 | C.5 |
| 1.1098 | B.153 | C.5 |
| 1.1099 | B.154 | C.5 |
| 1.1100 | B.155 | C.5 |
| 1.1101 | B.156 | C.5 |
| 1.1102 | B.157 | C.5 |
| 1.1103 | B.158 | C.5 |
| 1.1104 | B.159 | C.5 |
| 1.1105 | B.160 | C.5 |
| 1.1106 | B.161 | C.5 |
| 1.1107 | B.162 | C.5 |
| 1.1108 | B.163 | C.5 |
| 1.1109 | B.164 | C.5 |
| 1.1110 | B.165 | C.5 |
| 1.1111 | B.166 | C.5 |
| 1.1112 | B.167 | C.5 |
| 1.1113 | B.168 | C.5 |
| 1.1114 | B.169 | C.5 |
| 1.1115 | B.170 | C.5 |
| 1.1116 | B.171 | C.5 |
| 1.1117 | B.172 | C.5 |
| 1.1118 | B.173 | C.5 |
| 1.1119 | B.174 | C.5 |
| 1.1120 | B.175 | C.5 |
| 1.1121 | B.176 | C.5 |
| 1.1122 | B.177 | C.5 |
| 1.1123 | B.178 | C.5 |
| 1.1124 | B.179 | C.5 |
| 1.1125 | B.180 | C.5 |
| 1.1126 | B.181 | C.5 |
| 1.1127 | B.182 | C.5 |
| 1.1128 | B.183 | C.5 |
| 1.1129 | B.184 | C.5 |
| 1.1130 | B.185 | C.5 |
| 1.1131 | B.186 | C.5 |
| 1.1132 | B.187 | C.5 |
| 1.1133 | B.188 | C.5 |
| 1.1134 | B.189 | C.5 |
| 1.1135 | B.1 | C.6 |
| 1.1136 | B.2 | C.6 |
| 1.1137 | B.3 | C.6 |
| 1.1138 | B.4 | C.6 |
| 1.1139 | B.5 | C.6 |
| 1.1140 | B.6 | C.6 |
| 1.1141 | B.7 | C.6 |
| 1.1142 | B.8 | C.6 |
| 1.1143 | B.9 | C.6 |
| 1.1144 | B.10 | C.6 |
| 1.1145 | B.11 | C.6 |
| 1.1146 | B.12 | C.6 |
| 1.1147 | B.13 | C.6 |
| 1.1148 | B.14 | C.6 |

TABLE 1-continued (compositions 1.1 to 1.3419):

| comp. no. | herbicide B | safener C |
|---|---|---|
| 1.1149 | B.15 | C.6 |
| 1.1150 | B.16 | C.6 |
| 1.1151 | B.17 | C.6 |
| 1.1152 | B.18 | C.6 |
| 1.1153 | B.19 | C.6 |
| 1.1154 | B.20 | C.6 |
| 1.1155 | B.21 | C.6 |
| 1.1156 | B.22 | C.6 |
| 1.1157 | B.23 | C.6 |
| 1.1158 | B.24 | C.6 |
| 1.1159 | B.25 | C.6 |
| 1.1160 | B.26 | C.6 |
| 1.1161 | B.27 | C.6 |
| 1.1162 | B.28 | C.6 |
| 1.1163 | B.29 | C.6 |
| 1.1164 | B.30 | C.6 |
| 1.1165 | B.31 | C.6 |
| 1.1166 | B.32 | C.6 |
| 1.1167 | B.33 | C.6 |
| 1.1168 | B.34 | C.6 |
| 1.1169 | B.35 | C.6 |
| 1.1170 | B.36 | C.6 |
| 1.1171 | B.37 | C.6 |
| 1.1172 | B.38 | C.6 |
| 1.1173 | B.39 | C.6 |
| 1.1174 | B.40 | C.6 |
| 1.1175 | B.41 | C.6 |
| 1.1176 | B.42 | C.6 |
| 1.1177 | B.43 | C.6 |
| 1.1178 | B.44 | C.6 |
| 1.1179 | B.45 | C.6 |
| 1.1180 | B.46 | C.6 |
| 1.1181 | B.47 | C.6 |
| 1.1182 | B.48 | C.6 |
| 1.1183 | B.49 | C.6 |
| 1.1184 | B.50 | C.6 |
| 1.1185 | B.51 | C.6 |
| 1.1186 | B.52 | C.6 |
| 1.1187 | B.53 | C.6 |
| 1.1188 | B.54 | C.6 |
| 1.1189 | B.55 | C.6 |
| 1.1190 | B.56 | C.6 |
| 1.1191 | B.57 | C.6 |
| 1.1192 | B.58. | C.6 |
| 1.1193 | B.59 | C.6 |
| 1.1194 | B.60 | C.6 |
| 1.1195 | B.61 | C.6 |
| 1.1196 | B.62 | C.6 |
| 1.1197 | B.63 | C.6 |
| 1.1198 | B.64 | C.6 |
| 1.1199 | B.65 | C.6 |
| 1.1200 | B.66 | C.6 |
| 1.1201 | B.67 | C.6 |
| 1.1202 | B.68 | C.6 |
| 1.1203 | B.69 | C.6 |
| 1.1204 | B.70 | C.6 |
| 1.1205 | B.71 | C.6 |
| 1.1206 | B.72 | C.6 |
| 1.1207 | B.73 | C.6 |
| 1.1208 | B.74 | C.6 |
| 1.1209 | B.75 | C.6 |
| 1.1210 | B.76 | C.6 |
| 1.1211 | B.77 | C.6 |
| 1.1212 | B.78 | C.6 |
| 1.1213 | B.79 | C.6 |
| 1.1214 | B.80 | C.6 |
| 1.1215 | B.81 | C.6 |
| 1.1216 | B.82 | C.6 |
| 1.1217 | B.83 | C.6 |
| 1.1218 | B.84 | C.6 |
| 1.1219 | B.85 | C.6 |
| 1.1220 | B.86 | C.6 |
| 1.1221 | B.87 | C.6 |
| 1.1222 | B.88 | C.6 |
| 1.1223 | B.89 | C.6 |
| 1.1224 | B.90 | C.6 |
| 1.1225 | B.91 | C.6 |
| 1.1226 | B.92 | C.6 |
| 1.1227 | B.93 | C.6 |
| 1.1228 | B.94 | C.6 |
| 1.1229 | B.95 | C.6 |
| 1.1230 | B.96 | C.6 |
| 1.1231 | B.97 | C.6 |
| 1.1232 | B.98 | C.6 |
| 1.1233 | B.99 | C.6 |
| 1.1234 | B.100 | C.6 |
| 1.1235 | B.101 | C.6 |
| 1.1236 | B.102 | C.6 |
| 1.1237 | B.103 | C.6 |
| 1.1238 | B.104 | C.6 |
| 1.1239 | B.105 | C.6 |
| 1.1240 | B.106 | C.6 |
| 1.1241 | B.107 | C.6 |
| 1.1242 | B.108 | C.6 |
| 1.1243 | B.109 | C.6 |
| 1.1244 | B.110 | C.6 |
| 1.1245 | B.111 | C.6 |
| 1.1246 | B.112 | C.6 |
| 1.1247 | B.113 | C.6 |
| 1.1248 | B.114 | C.6 |
| 1.1249 | B.115 | C.6 |
| 1.1250 | B.116 | C.6 |
| 1.1251 | B.117 | C.6 |
| 1.1252 | B.118 | C.6 |
| 1.1253 | B.119 | C.6 |
| 1.1254 | B.120 | C.6 |
| 1.1255 | B.121 | C.6 |
| 1.1256 | B.122 | C.6 |
| 1.1257 | B.123 | C.6 |
| 1.1258 | B.124 | C.6 |
| 1.1259 | B.125 | C.6 |
| 1.1260 | B.126 | C.6 |
| 1.1261 | B.127 | C.6 |
| 1.1262 | B.128 | C.6 |
| 1.1263 | B.129 | C.6 |
| 1.1264 | B.130 | C.6 |
| 1.1265 | B.131 | C.6 |
| 1.1266 | B.132 | C.6 |
| 1.1267 | B.133 | C.6 |
| 1.1268 | B.134 | C.6 |
| 1.1269 | B.135 | C.6 |
| 1.1270 | B.136 | C.6 |
| 1.1271 | B.137 | C.6 |
| 1.1272 | B.138 | C.6 |
| 1.1273 | B.139 | C.6 |
| 1.1274 | B.140 | C.6 |
| 1.1275 | B.141 | C.6 |
| 1.1276 | B.142 | C.6 |
| 1.1277 | B.143 | C.6 |
| 1.1278 | B.144 | C.6 |
| 1.1279 | B.145 | C.6 |
| 1.1280 | B.146 | C.6 |
| 1.1281 | B.147 | C.6 |
| 1.1282 | B.148 | C.6 |
| 1.1283 | B.149 | C.6 |
| 1.1284 | B.150 | C.6 |
| 1.1285 | B.151 | C.6 |
| 1.1286 | B.152 | C.6 |
| 1.1287 | B.153 | C.6 |
| 1.1288 | B.154 | C.6 |
| 1.1289 | B.155 | C.6 |
| 1.1290 | B.156 | C.6 |
| 1.1291 | B.157 | C.6 |
| 1.1292 | B.158 | C.6 |
| 1.1293 | B.159 | C.6 |
| 1.1294 | B.160 | C.6 |
| 1.1295 | B.161 | C.6 |
| 1.1296 | B.162 | C.6 |
| 1.1297 | B.163 | C.6 |
| 1.1298 | B.164 | C.6 |
| 1.1299 | B.165 | C.6 |
| 1.1300 | B.166 | C.6 |

TABLE 1-continued (compositions 1.1 to 1.3419):

| comp. no. | herbicide B | safener C |
|---|---|---|
| 1.1301 | B.167 | C.6 |
| 1.1302 | B.168 | C.6 |
| 1.1303 | B.169 | C.6 |
| 1.1304 | B.170 | C.6 |
| 1.1305 | B.171 | C.6 |
| 1.1306 | B.172 | C.6 |
| 1.1307 | B.173 | C.6 |
| 1.1308 | B.174 | C.6 |
| 1.1309 | B.175 | C.6 |
| 1.1310 | B.176 | C.6 |
| 1.1311 | B.177 | C.6 |
| 1.1312 | B.178 | C.6 |
| 1.1313 | B.179 | C.6 |
| 1.1314 | B.180 | C.6 |
| 1.1315 | B.181 | C.6 |
| 1.1316 | B.182 | C.6 |
| 1.1317 | B.183 | C.6 |
| 1.1318 | B.184 | C.6 |
| 1.1319 | B.185 | C.6 |
| 1.1320 | B.186 | C.6 |
| 1.1321 | B.187 | C.6 |
| 1.1322 | B.188 | C.6 |
| 1.1323 | B.189 | C.6 |
| 1.1324 | B.1 | C.7 |
| 1.1325 | B.2 | C.7 |
| 1.1326 | B.3 | C.7 |
| 1.1327 | B.4 | C.7 |
| 1.1328 | B.5 | C.7 |
| 1.1329 | B.6 | C.7 |
| 1.1330 | B.7 | C.7 |
| 1.1331 | B.8 | C.7 |
| 1.1332 | B.9 | C.7 |
| 1.1333 | B.10 | C.7 |
| 1.1334 | B.11 | C.7 |
| 1.1335 | B.12 | C.7 |
| 1.1336 | B.13 | C.7 |
| 1.1337 | B.14 | C.7 |
| 1.1338 | B.15 | C.7 |
| 1.1339 | B.16 | C.7 |
| 1.1340 | B.17 | C.7 |
| 1.1341 | B.18 | C.7 |
| 1.1342 | B.19 | C.7 |
| 1.1343 | B.20 | C.7 |
| 1.1344 | B.21 | C.7 |
| 1.1345 | B.22 | C.7 |
| 1.1346 | B.23 | C.7 |
| 1.1347 | B.24 | C.7 |
| 1.1348 | B.25 | C.7 |
| 1.1349 | B.26 | C.7 |
| 1.1350 | B.27 | C.7 |
| 1.1351 | B.28 | C.7 |
| 1.1352 | B.29 | C.7 |
| 1.1353 | B.30 | C.7 |
| 1.1354 | B.31 | C.7 |
| 1.1355 | B.32 | C.7 |
| 1.1356 | B.33 | C.7 |
| 1.1357 | B.34 | C.7 |
| 1.1358 | B.35 | C.7 |
| 1.1359 | B.36 | C.7 |
| 1.1360 | B.37 | C.7 |
| 1.1361 | B.38 | C.7 |
| 1.1362 | B.39 | C.7 |
| 1.1363 | B.40 | C.7 |
| 1.1364 | B.41 | C.7 |
| 1.1365 | B.42 | C.7 |
| 1.1366 | B.43 | C.7 |
| 1.1367 | B.44 | C.7 |
| 1.1368 | B.45 | C.7 |
| 1.1369 | B.46 | C.7 |
| 1.1370 | B.47 | C.7 |
| 1.1371 | B.48 | C.7 |
| 1.1372 | B.49 | C.7 |
| 1.1373 | B.50 | C.7 |
| 1.1374 | B.51 | C.7 |
| 1.1375 | B.52 | C.7 |
| 1.1376 | B.53 | C.7 |
| 1.1377 | B.54 | C.7 |
| 1.1378 | B.55 | C.7 |
| 1.1379 | B.56 | C.7 |
| 1.1380 | B.57 | C.7 |
| 1.1381 | B.58. | C.7 |
| 1.1382 | B.59 | C.7 |
| 1.1383 | B.60 | C.7 |
| 1.1384 | B.61 | C.7 |
| 1.1385 | B.62 | C.7 |
| 1.1386 | B.63 | C.7 |
| 1.1387 | B.64 | C.7 |
| 1.1388 | B.65 | C.7 |
| 1.1389 | B.66 | C.7 |
| 1.1390 | B.67 | C.7 |
| 1.1391 | B.68 | C.7 |
| 1.1392 | B.69 | C.7 |
| 1.1393 | B.70 | C.7 |
| 1.1394 | B.71 | C.7 |
| 1.1395 | B.72 | C.7 |
| 1.1396 | B.73 | C.7 |
| 1.1397 | B.74 | C.7 |
| 1.1398 | B.75 | C.7 |
| 1.1399 | B.76 | C.7 |
| 1.1400 | B.77 | C.7 |
| 1.1401 | B.78 | C.7 |
| 1.1402 | B.79 | C.7 |
| 1.1403 | B.80 | C.7 |
| 1.1404 | B.81 | C.7 |
| 1.1405 | B.82 | C.7 |
| 1.1406 | B.83 | C.7 |
| 1.1407 | B.84 | C.7 |
| 1.1408 | B.85 | C.7 |
| 1.1409 | B.86 | C.7 |
| 1.1410 | B.87 | C.7 |
| 1.1411 | B.88 | C.7 |
| 1.1412 | B.89 | C.7 |
| 1.1413 | B.90 | C.7 |
| 1.1414 | B.91 | C.7 |
| 1.1415 | B.92 | C.7 |
| 1.1416 | B.93 | C.7 |
| 1.1417 | B.94 | C.7 |
| 1.1418 | B.95 | C.7 |
| 1.1419 | B.96 | C.7 |
| 1.1420 | B.97 | C.7 |
| 1.1421 | B.98 | C.7 |
| 1.1422 | B.99 | C.7 |
| 1.1423 | B.100 | C.7 |
| 1.1424 | B.101 | C.7 |
| 1.1425 | B.102 | C.7 |
| 1.1426 | B.103 | C.7 |
| 1.1427 | B.104 | C.7 |
| 1.1428 | B.105 | C.7 |
| 1.1429 | B.106 | C.7 |
| 1.1430 | B.107 | C.7 |
| 1.1431 | B.108 | C.7 |
| 1.1432 | B.109 | C.7 |
| 1.1433 | B.110 | C.7 |
| 1.1434 | B.111 | C.7 |
| 1.1435 | B.112 | C.7 |
| 1.1436 | B.113 | C.7 |
| 1.1437 | B.114 | C.7 |
| 1.1438 | B.115 | C.7 |
| 1.1439 | B.116 | C.7 |
| 1.1440 | B.117 | C.7 |
| 1.1441 | B.118 | C.7 |
| 1.1442 | B.119 | C.7 |
| 1.1443 | B.120 | C.7 |
| 1.1444 | B.121 | C.7 |
| 1.1445 | B.122 | C.7 |
| 1.1446 | B.123 | C.7 |
| 1.1447 | B.124 | C.7 |
| 1.1448 | B.125 | C.7 |
| 1.1449 | B.126 | C.7 |
| 1.1450 | B.127 | C.7 |
| 1.1451 | B.128 | C.7 |
| 1.1452 | B.129 | C.7 |

TABLE 1-continued (compositions 1.1 to 1.3419):

| comp. no. | herbicide B | safener C |
|---|---|---|
| 1.1453 | B.130 | C.7 |
| 1.1454 | B.131 | C.7 |
| 1.1455 | B.132 | C.7 |
| 1.1456 | B.133 | C.7 |
| 1.1457 | B.134 | C.7 |
| 1.1458 | B.135 | C.7 |
| 1.1459 | B.136 | C.7 |
| 1.1460 | B.137 | C.7 |
| 1.1461 | B.138 | C.7 |
| 1.1462 | B.139 | C.7 |
| 1.1463 | B.140 | C.7 |
| 1.1464 | B.141 | C.7 |
| 1.1465 | B.142 | C.7 |
| 1.1466 | B.143 | C.7 |
| 1.1467 | B.144 | C.7 |
| 1.1468 | B.145 | C.7 |
| 1.1469 | B.146 | C.7 |
| 1.1470 | B.147 | C.7 |
| 1.1471 | B.148 | C.7 |
| 1.1472 | B.149 | C.7 |
| 1.1473 | B.150 | C.7 |
| 1.1474 | B.151 | C.7 |
| 1.1475 | B.152 | C.7 |
| 1.1476 | B.153 | C.7 |
| 1.1477 | B.154 | C.7 |
| 1.1478 | B.155 | C.7 |
| 1.1479 | B.156 | C.7 |
| 1.1480 | B.157 | C.7 |
| 1.1481 | B.158 | C.7 |
| 1.1482 | B.159 | C.7 |
| 1.1483 | B.160 | C.7 |
| 1.1484 | B.161 | C.7 |
| 1.1485 | B.162 | C.7 |
| 1.1486 | B.163 | C.7 |
| 1.1487 | B.164 | C.7 |
| 1.1488 | B.165 | C.7 |
| 1.1489 | B.166 | C.7 |
| 1.1490 | B.167 | C.7 |
| 1.1491 | B.168 | C.7 |
| 1.1492 | B.169 | C.7 |
| 1.1493 | B.170 | C.7 |
| 1.1494 | B.171 | C.7 |
| 1.1495 | B.172 | C.7 |
| 1.1496 | B.173 | C.7 |
| 1.1497 | B.174 | C.7 |
| 1.1498 | B.175 | C.7 |
| 1.1499 | B.176 | C.7 |
| 1.1500 | B.177 | C.7 |
| 1.1501 | B.178 | C.7 |
| 1.1502 | B.179 | C.7 |
| 1.1503 | B.180 | C.7 |
| 1.1504 | B.181 | C.7 |
| 1.1505 | B.182 | C.7 |
| 1.1506 | B.183 | C.7 |
| 1.1507 | B.184 | C.7 |
| 1.1508 | B.185 | C.7 |
| 1.1509 | B.186 | C.7 |
| 1.1510 | B.187 | C.7 |
| 1.1511 | B.188 | C.7 |
| 1.1512 | B.189 | C.7 |
| 1.1513 | B.1 | C.8 |
| 1.1514 | B.2 | C.8 |
| 1.1515 | B.3 | C.8 |
| 1.1516 | B.4 | C.8 |
| 1.1517 | B.5 | C.8 |
| 1.1518 | B.6 | C.8 |
| 1.1519 | B.7 | C.8 |
| 1.1520 | B.8 | C.8 |
| 1.1521 | B.9 | C.8 |
| 1.1522 | B.10 | C.8 |
| 1.1523 | B.11 | C.8 |
| 1.1524 | B.12 | C.8 |
| 1.1525 | B.13 | C.8 |
| 1.1526 | B.14 | C.8 |
| 1.1527 | B.15 | C.8 |
| 1.1528 | B.16 | C.8 |
| 1.1529 | B.17 | C.8 |
| 1.1530 | B.18 | C.8 |
| 1.1531 | B.19 | C.8 |
| 1.1532 | B.20 | C.8 |
| 1.1533 | B.21 | C.8 |
| 1.1534 | B.22 | C.8 |
| 1.1535 | B.23 | C.8 |
| 1.1536 | B.24 | C.8 |
| 1.1537 | B.25 | C.8 |
| 1.1538 | B.26 | C.8 |
| 1.1539 | B.27 | C.8 |
| 1.1540 | B.28 | C.8 |
| 1.1541 | B.29 | C.8 |
| 1.1542 | B.30 | C.8 |
| 1.1543 | B.31 | C.8 |
| 1.1544 | B.32 | C.8 |
| 1.1545 | B.33 | C.8 |
| 1.1546 | B.34 | C.8 |
| 1.1547 | B.35 | C.8 |
| 1.1548 | B.36 | C.8 |
| 1.1549 | B.37 | C.8 |
| 1.1550 | B.38 | C.8 |
| 1.1551 | B.39 | C.8 |
| 1.1552 | B.40 | C.8 |
| 1.1553 | B.41 | C.8 |
| 1.1554 | B.42 | C.8 |
| 1.1555 | B.43 | C.8 |
| 1.1556 | B.44 | C.8 |
| 1.1557 | B.45 | C.8 |
| 1.1558 | B.46 | C.8 |
| 1.1559 | B.47 | C.8 |
| 1.1560 | B.48 | C.8 |
| 1.1561 | B.49 | C.8 |
| 1.1562 | B.50 | C.8 |
| 1.1563 | B.51 | C.8 |
| 1.1564 | B.52 | C.8 |
| 1.1565 | B.53 | C.8 |
| 1.1566 | B.54 | C.8 |
| 1.1567 | B.55 | C.8 |
| 1.1568 | B.56 | C.8 |
| 1.1569 | B.57 | C.8 |
| 1.1570 | B.58. | C.8 |
| 1.1571 | B.59 | C.8 |
| 1.1572 | B.60 | C.8 |
| 1.1573 | B.61 | C.8 |
| 1.1574 | B.62 | C.8 |
| 1.1575 | B.63 | C.8 |
| 1.1576 | B.64 | C.8 |
| 1.1577 | B.65 | C.8 |
| 1.1578 | B.66 | C.8 |
| 1.1579 | B.67 | C.8 |
| 1.1580 | B.68 | C.8 |
| 1.1581 | B.69 | C.8 |
| 1.1582 | B.70 | C.8 |
| 1.1583 | B.71 | C.8 |
| 1.1584 | B.72 | C.8 |
| 1.1585 | B.73 | C.8 |
| 1.1586 | B.74 | C.8 |
| 1.1587 | B.75 | C.8 |
| 1.1588 | B.76 | C.8 |
| 1.1589 | B.77 | C.8 |
| 1.1590 | B.78 | C.8 |
| 1.1591 | B.79 | C.8 |
| 1.1592 | B.80 | C.8 |
| 1.1593 | B.81 | C.8 |
| 1.1594 | B.82 | C.8 |
| 1.1595 | B.83 | C.8 |
| 1.1596 | B.84 | C.8 |
| 1.1597 | B.85 | C.8 |
| 1.1598 | B.86 | C.8 |
| 1.1599 | B.87 | C.8 |
| 1.1600 | B.88 | C.8 |
| 1.1601 | B.89 | C.8 |
| 1.1602 | B.90 | C.8 |
| 1.1603 | B.91 | C.8 |
| 1.1604 | B.92 | C.8 |

TABLE 1-continued (compositions 1.1 to 1.3419):

| comp. no. | herbicide B | safener C |
|---|---|---|
| 1.1605 | B.93 | C.8 |
| 1.1606 | B.94 | C.8 |
| 1.1607 | B.95 | C.8 |
| 1.1608 | B.96 | C.8 |
| 1.1609 | B.97 | C.8 |
| 1.1610 | B.98 | C.8 |
| 1.1611 | B.99 | C.8 |
| 1.1612 | B.100 | C.8 |
| 1.1613 | B.101 | C.8 |
| 1.1614 | B.102 | C.8 |
| 1.1615 | B.103 | C.8 |
| 1.1616 | B.104 | C.8 |
| 1.1617 | B.105 | C.8 |
| 1.1618 | B.106 | C.8 |
| 1.1619 | B.107 | C.8 |
| 1.1620 | B.108 | C.8 |
| 1.1621 | B.109 | C.8 |
| 1.1622 | B.110 | C.8 |
| 1.1623 | B.111 | C.8 |
| 1.1624 | B.112 | C.8 |
| 1.1625 | B.113 | C.8 |
| 1.1626 | B.114 | C.8 |
| 1.1627 | B.115 | C.8 |
| 1.1628 | B.116 | C.8 |
| 1.1629 | B.117 | C.8 |
| 1.1630 | B.118 | C.8 |
| 1.1631 | B.119 | C.8 |
| 1.1632 | B.120 | C.8 |
| 1.1633 | B.121 | C.8 |
| 1.1634 | B.122 | C.8 |
| 1.1635 | B.123 | C.8 |
| 1.1636 | B.124 | C.8 |
| 1.1637 | B.125 | C.8 |
| 1.1638 | B.126 | C.8 |
| 1.1639 | B.127 | C.8 |
| 1.1640 | B.128 | C.8 |
| 1.1641 | B.129 | C.8 |
| 1.1642 | B.130 | C.8 |
| 1.1643 | B.131 | C.8 |
| 1.1644 | B.132 | C.8 |
| 1.1645 | B.133 | C.8 |
| 1.1646 | B.134 | C.8 |
| 1.1647 | B.135 | C.8 |
| 1.1648 | B.136 | C.8 |
| 1.1649 | B.137 | C.8 |
| 1.1650 | B.138 | C.8 |
| 1.1651 | B.139 | C.8 |
| 1.1652 | B.140 | C.8 |
| 1.1653 | B.141 | C.8 |
| 1.1654 | B.142 | C.8 |
| 1.1655 | B.143 | C.8 |
| 1.1656 | B.144 | C.8 |
| 1.1657 | B.145 | C.8 |
| 1.1658 | B.146 | C.8 |
| 1.1659 | B.147 | C.8 |
| 1.1660 | B.148 | C.8 |
| 1.1661 | B.149 | C.8 |
| 1.1662 | B.150 | C.8 |
| 1.1663 | B.151 | C.8 |
| 1.1664 | B.152 | C.8 |
| 1.1665 | B.153 | C.8 |
| 1.1666 | B.154 | C.8 |
| 1.1667 | B.155 | C.8 |
| 1.1668 | B.156 | C.8 |
| 1.1669 | B.157 | C.8 |
| 1.1670 | B.158 | C.8 |
| 1.1671 | B.159 | C.8 |
| 1.1672 | B.160 | C.8 |
| 1.1673 | B.161 | C.8 |
| 1.1674 | B.162 | C.8 |
| 1.1675 | B.163 | C.8 |
| 1.1676 | B.164 | C.8 |
| 1.1677 | B.165 | C.8 |
| 1.1678 | B.166 | C.8 |
| 1.1679 | B.167 | C.8 |
| 1.1680 | B.168 | C.8 |
| 1.1681 | B.169 | C.8 |
| 1.1682 | B.170 | C.8 |
| 1.1683 | B.171 | C.8 |
| 1.1684 | B.172 | C.8 |
| 1.1685 | B.173 | C.8 |
| 1.1686 | B.174 | C.8 |
| 1.1687 | B.175 | C.8 |
| 1.1688 | B.176 | C.8 |
| 1.1689 | B.177 | C.8 |
| 1.1690 | B.178 | C.8 |
| 1.1691 | B.179 | C.8 |
| 1.1692 | B.180 | C.8 |
| 1.1693 | B.181 | C.8 |
| 1.1694 | B.182 | C.8 |
| 1.1695 | B.183 | C.8 |
| 1.1696 | B.184 | C.8 |
| 1.1697 | B.185 | C.8 |
| 1.1698 | B.186 | C.8 |
| 1.1699 | B.187 | C.8 |
| 1.1700 | B.188 | C.8 |
| 1.1701 | B.189 | C.8 |
| 1.1702 | B.1 | C.9 |
| 1.1703 | B.2 | C.9 |
| 1.1704 | B.3 | C.9 |
| 1.1705 | B.4 | C.9 |
| 1.1706 | B.5 | C.9 |
| 1.1707 | B.6 | C.9 |
| 1.1708 | B.7 | C.9 |
| 1.1709 | B.8 | C.9 |
| 1.1710 | B.9 | C.9 |
| 1.1711 | B.10 | C.9 |
| 1.1712 | B.11 | C.9 |
| 1.1713 | B.12 | C.9 |
| 1.1714 | B.13 | C.9 |
| 1.1715 | B.14 | C.9 |
| 1.1716 | B.15 | C.9 |
| 1.1717 | B.16 | C.9 |
| 1.1718 | B.17 | C.9 |
| 1.1719 | B.18 | C.9 |
| 1.1720 | B.19 | C.9 |
| 1.1721 | B.20 | C.9 |
| 1.1722 | B.21 | C.9 |
| 1.1723 | B.22 | C.9 |
| 1.1724 | B.23 | C.9 |
| 1.1725 | B.24 | C.9 |
| 1.1726 | B.25 | C.9 |
| 1.1727 | B.26 | C.9 |
| 1.1728 | B.27 | C.9 |
| 1.1729 | B.28 | C.9 |
| 1.1730 | B.29 | C.9 |
| 1.1731 | B.30 | C.9 |
| 1.1732 | B.31 | C.9 |
| 1.1733 | B.32 | C.9 |
| 1.1734 | B.33 | C.9 |
| 1.1735 | B.34 | C.9 |
| 1.1736 | B.35 | C.9 |
| 1.1737 | B.36 | C.9 |
| 1.1738 | B.37 | C.9 |
| 1.1739 | B.38 | C.9 |
| 1.1740 | B.39 | C.9 |
| 1.1741 | B.40 | C.9 |
| 1.1742 | B.41 | C.9 |
| 1.1743 | B.42 | C.9 |
| 1.1744 | B.43 | C.9 |
| 1.1745 | B.44 | C.9 |
| 1.1746 | B.45 | C.9 |
| 1.1747 | B.46 | C.9 |
| 1.1748 | B.47 | C.9 |
| 1.1749 | B.48 | C.9 |
| 1.1750 | B.49 | C.9 |
| 1.1751 | B.50 | C.9 |
| 1.1752 | B.51 | C.9 |
| 1.1753 | B.52 | C.9 |
| 1.1754 | B.53 | C.9 |
| 1.1755 | B.54 | C.9 |
| 1.1756 | B.55 | C.9 |

TABLE 1-continued (compositions 1.1 to 1.3419):

| comp. no. | herbicide B | safener C |
|---|---|---|
| 1.1757 | B.56 | C.9 |
| 1.1758 | B.57 | C.9 |
| 1.1759 | B.58. | C.9 |
| 1.1760 | B.59 | C.9 |
| 1.1761 | B.60 | C.9 |
| 1.1762 | B.61 | C.9 |
| 1.1763 | B.62 | C.9 |
| 1.1764 | B.63 | C.9 |
| 1.1765 | B.64 | C.9 |
| 1.1766 | B.65 | C.9 |
| 1.1767 | B.66 | C.9 |
| 1.1768 | B.67 | C.9 |
| 1.1769 | B.68 | C.9 |
| 1.1770 | B.69 | C.9 |
| 1.1771 | B.70 | C.9 |
| 1.1772 | B.71 | C.9 |
| 1.1773 | B.72 | C.9 |
| 1.1774 | B.73 | C.9 |
| 1.1775 | B.74 | C.9 |
| 1.1776 | B.75 | C.9 |
| 1.1777 | B.76 | C.9 |
| 1.1778 | B.77 | C.9 |
| 1.1779 | B.78 | C.9 |
| 1.1780 | B.79 | C.9 |
| 1.1781 | B.80 | C.9 |
| 1.1782 | B.81 | C.9 |
| 1.1783 | B.82 | C.9 |
| 1.1784 | B.83 | C.9 |
| 1.1785 | B.84 | C.9 |
| 1.1786 | B.85 | C.9 |
| 1.1787 | B.86 | C.9 |
| 1.1788 | B.87 | C.9 |
| 1.1789 | B.88 | C.9 |
| 1.1790 | B.89 | C.9 |
| 1.1791 | B.90 | C.9 |
| 1.1792 | B.91 | C.9 |
| 1.1793 | B.92 | C.9 |
| 1.1794 | B.93 | C.9 |
| 1.1795 | B.94 | C.9 |
| 1.1796 | B.95 | C.9 |
| 1.1797 | B.96 | C.9 |
| 1.1798 | B.97 | C.9 |
| 1.1799 | B.98 | C.9 |
| 1.1800 | B.99 | C.9 |
| 1.1801 | B.100 | C.9 |
| 1.1802 | B.101 | C.9 |
| 1.1803 | B.102 | C.9 |
| 1.1804 | B.103 | C.9 |
| 1.1805 | B.104 | C.9 |
| 1.1806 | B.105 | C.9 |
| 1.1807 | B.106 | C.9 |
| 1.1808 | B.107 | C.9 |
| 1.1809 | B.108 | C.9 |
| 1.1810 | B.109 | C.9 |
| 1.1811 | B.110 | C.9 |
| 1.1812 | B.111 | C.9 |
| 1.1813 | B.112 | C.9 |
| 1.1814 | B.113 | C.9 |
| 1.1815 | B.114 | C.9 |
| 1.1816 | B.115 | C.9 |
| 1.1817 | B.116 | C.9 |
| 1.1818 | B.117 | C.9 |
| 1.1819 | B.118 | C.9 |
| 1.1820 | B.119 | C.9 |
| 1.1821 | B.120 | C.9 |
| 1.1822 | B.121 | C.9 |
| 1.1823 | B.122 | C.9 |
| 1.1824 | B.123 | C.9 |
| 1.1825 | B.124 | C.9 |
| 1.1826 | B.125 | C.9 |
| 1.1827 | B.126 | C.9 |
| 1.1828 | B.127 | C.9 |
| 1.1829 | B.128 | C.9 |
| 1.1830 | B.129 | C.9 |
| 1.1831 | B.130 | C.9 |
| 1.1832 | B.131 | C.9 |
| 1.1833 | B.132 | C.9 |
| 1.1834 | B.133 | C.9 |
| 1.1835 | B.134 | C.9 |
| 1.1836 | B.135 | C.9 |
| 1.1837 | B.136 | C.9 |
| 1.1838 | B.137 | C.9 |
| 1.1839 | B.138 | C.9 |
| 1.1840 | B.139 | C.9 |
| 1.1841 | B.140 | C.9 |
| 1.1842 | B.141 | C.9 |
| 1.1843 | B.142 | C.9 |
| 1.1844 | B.143 | C.9 |
| 1.1845 | B.144 | C.9 |
| 1.1846 | B.145 | C.9 |
| 1.1847 | B.146 | C.9 |
| 1.1848 | B.147 | C.9 |
| 1.1849 | B.148 | C.9 |
| 1.1850 | B.149 | C.9 |
| 1.1851 | B.150 | C.9 |
| 1.1852 | B.151 | C.9 |
| 1.1853 | B.152 | C.9 |
| 1.1854 | B.153 | C.9 |
| 1.1855 | B.154 | C.9 |
| 1.1856 | B.155 | C.9 |
| 1.1857 | B.156 | C.9 |
| 1.1858 | B.157 | C.9 |
| 1.1859 | B.158 | C.9 |
| 1.1860 | B.159 | C.9 |
| 1.1861 | B.160 | C.9 |
| 1.1862 | B.161 | C.9 |
| 1.1863 | B.162 | C.9 |
| 1.1864 | B.163 | C.9 |
| 1.1865 | B.164 | C.9 |
| 1.1866 | B.165 | C.9 |
| 1.1867 | B.166 | C.9 |
| 1.1868 | B.167 | C.9 |
| 1.1869 | B.168 | C.9 |
| 1.1870 | B.169 | C.9 |
| 1.1871 | B.170 | C.9 |
| 1.1872 | B.171 | C.9 |
| 1.1873 | B.172 | C.9 |
| 1.1874 | B.173 | C.9 |
| 1.1875 | B.174 | C.9 |
| 1.1876 | B.175 | C.9 |
| 1.1877 | B.176 | C.9 |
| 1.1878 | B.177 | C.9 |
| 1.1879 | B.178 | C.9 |
| 1.1880 | B.179 | C.9 |
| 1.1881 | B.180 | C.9 |
| 1.1882 | B.181 | C.9 |
| 1.1883 | B.182 | C.9 |
| 1.1884 | B.183 | C.9 |
| 1.1885 | B.184 | C.9 |
| 1.1886 | B.185 | C.9 |
| 1.1887 | B.186 | C.9 |
| 1.1888 | B.187 | C.9 |
| 1.1889 | B.188 | C.9 |
| 1.1890 | B.189 | C.9 |
| 1.1891 | B.1 | C.10 |
| 1.1892 | B.2 | C.10 |
| 1.1893 | B.3 | C.10 |
| 1.1894 | B.4 | C.10 |
| 1.1895 | B.5 | C.10 |
| 1.1896 | B.6 | C.10 |
| 1.1897 | B.7 | C.10 |
| 1.1898 | B.8 | C.10 |
| 1.1899 | B.9 | C.10 |
| 1.1900 | B.10 | C.10 |
| 1.1901 | B.11 | C.10 |
| 1.1902 | B.12 | C.10 |
| 1.1903 | B.13 | C.10 |
| 1.1904 | B.14 | C.10 |
| 1.1905 | B.15 | C.10 |
| 1.1906 | B.16 | C.10 |
| 1.1907 | B.17 | C.10 |
| 1.1908 | B.18 | C.10 |

TABLE 1-continued (compositions 1.1 to 1.3419):

| comp. no. | herbicide B | safener C |
|---|---|---|
| 1.1909 | B.19 | C.10 |
| 1.1910 | B.20 | C.10 |
| 1.1911 | B.21 | C.10 |
| 1.1912 | B.22 | C.10 |
| 1.1913 | B.23 | C.10 |
| 1.1914 | B.24 | C.10 |
| 1.1915 | B.25 | C.10 |
| 1.1916 | B.26 | C.10 |
| 1.1917 | B.27 | C.10 |
| 1.1918 | B.28 | C.10 |
| 1.1919 | B.29 | C.10 |
| 1.1920 | B.30 | C.10 |
| 1.1921 | B.31 | C.10 |
| 1.1922 | B.32 | C.10 |
| 1.1923 | B.33 | C.10 |
| 1.1924 | B.34 | C.10 |
| 1.1925 | B.35 | C.10 |
| 1.1926 | B.36 | C.10 |
| 1.1927 | B.37 | C.10 |
| 1.1928 | B.38 | C.10 |
| 1.1929 | B.39 | C.10 |
| 1.1930 | B.40 | C.10 |
| 1.1931 | B.41 | C.10 |
| 1.1932 | B.42 | C.10 |
| 1.1933 | B.43 | C.10 |
| 1.1934 | B.44 | C.10 |
| 1.1935 | B.45 | C.10 |
| 1.1936 | B.46 | C.10 |
| 1.1937 | B.47 | C.10 |
| 1.1938 | B.48 | C.10 |
| 1.1939 | B.49 | C.10 |
| 1.1940 | B.50 | C.10 |
| 1.1941 | B.51 | C.10 |
| 1.1942 | B.52 | C.10 |
| 1.1943 | B.53 | C.10 |
| 1.1944 | B.54 | C.10 |
| 1.1945 | B.55 | C.10 |
| 1.1946 | B.56 | C.10 |
| 1.1947 | B.57 | C.10 |
| 1.1948 | B.58. | C.10 |
| 1.1949 | B.59 | C.10 |
| 1.1950 | B.60 | C.10 |
| 1.1951 | B.61 | C.10 |
| 1.1952 | B.62 | C.10 |
| 1.1953 | B.63 | C.10 |
| 1.1954 | B.64 | C.10 |
| 1.1955 | B.65 | C.10 |
| 1.1956 | B.66 | C.10 |
| 1.1957 | B.67 | C.10 |
| 1.1958 | B.68 | C.10 |
| 1.1959 | B.69 | C.10 |
| 1.1960 | B.70 | C.10 |
| 1.1961 | B.71 | C.10 |
| 1.1962 | B.72 | C.10 |
| 1.1963 | B.73 | C.10 |
| 1.1964 | B.74 | C.10 |
| 1.1965 | B.75 | C.10 |
| 1.1966 | B.76 | C.10 |
| 1.1967 | B.77 | C.10 |
| 1.1968 | B.78 | C.10 |
| 1.1969 | B.79 | C.10 |
| 1.1970 | B.80 | C.10 |
| 1.1971 | B.81 | C.10 |
| 1.1972 | B.82 | C.10 |
| 1.1973 | B.83 | C.10 |
| 1.1974 | B.84 | C.10 |
| 1.1975 | B.85 | C.10 |
| 1.1976 | B.86 | C.10 |
| 1.1977 | B.87 | C.10 |
| 1.1978 | B.88 | C.10 |
| 1.1979 | B.89 | C.10 |
| 1.1980 | B.90 | C.10 |
| 1.1981 | B.91 | C.10 |
| 1.1982 | B.92 | C.10 |
| 1.1983 | B.93 | C.10 |
| 1.1984 | B.94 | C.10 |
| 1.1985 | B.95 | C.10 |
| 1.1986 | B.96 | C.10 |
| 1.1987 | B.97 | C.10 |
| 1.1988 | B.98 | C.10 |
| 1.1989 | B.99 | C.10 |
| 1.1990 | B.100 | C.10 |
| 1.1991 | B.101 | C.10 |
| 1.1992 | B.102 | C.10 |
| 1.1993 | B.103 | C.10 |
| 1.1994 | B.104 | C.10 |
| 1.1995 | B.105 | C.10 |
| 1.1996 | B.106 | C.10 |
| 1.1997 | B.107 | C.10 |
| 1.1998 | B.108 | C.10 |
| 1.1999 | B.109 | C.10 |
| 1.2000 | B.110 | C.10 |
| 1.2001 | B.111 | C.10 |
| 1.2002 | B.112 | C.10 |
| 1.2003 | B.113 | C.10 |
| 1.2004 | B.114 | C.10 |
| 1.2005 | B.115 | C.10 |
| 1.2006 | B.116 | C.10 |
| 1.2007 | B.117 | C.10 |
| 1.2008 | B.118 | C.10 |
| 1.2009 | B.119 | C.10 |
| 1.2010 | B.120 | C.10 |
| 1.2011 | B.121 | C.10 |
| 1.2012 | B.122 | C.10 |
| 1.2013 | B.123 | C.10 |
| 1.2014 | B.124 | C.10 |
| 1.2015 | B.125 | C.10 |
| 1.2016 | B.126 | C.10 |
| 1.2017 | B.127 | C.10 |
| 1.2018 | B.128 | C.10 |
| 1.2019 | B.129 | C.10 |
| 1.2020 | B.130 | C.10 |
| 1.2021 | B.131 | C.10 |
| 1.2022 | B.132 | C.10 |
| 1.2023 | B.133 | C.10 |
| 1.2024 | B.134 | C.10 |
| 1.2025 | B.135 | C.10 |
| 1.2026 | B.136 | C.10 |
| 1.2027 | B.137 | C.10 |
| 1.2028 | B.138 | C.10 |
| 1.2029 | B.139 | C.10 |
| 1.2030 | B.140 | C.10 |
| 1.2031 | B.141 | C.10 |
| 1.2032 | B.142 | C.10 |
| 1.2033 | B.143 | C.10 |
| 1.2034 | B.144 | C.10 |
| 1.2035 | B.145 | C.10 |
| 1.2036 | B.146 | C.10 |
| 1.2037 | B.147 | C.10 |
| 1.2038 | B.148 | C.10 |
| 1.2039 | B.149 | C.10 |
| 1.2040 | B.150 | C.10 |
| 1.2041 | B.151 | C.10 |
| 1.2042 | B.152 | C.10 |
| 1.2043 | B.153 | C.10 |
| 1.2044 | B.154 | C.10 |
| 1.2045 | B.155 | C.10 |
| 1.2046 | B.156 | C.10 |
| 1.2047 | B.157 | C.10 |
| 1.2048 | B.158 | C.10 |
| 1.2049 | B.159 | C.10 |
| 1.2050 | B.160 | C.10 |
| 1.2051 | B.161 | C.10 |
| 1.2052 | B.162 | C.10 |
| 1.2053 | B.163 | C.10 |
| 1.2054 | B.164 | C.10 |
| 1.2055 | B.165 | C.10 |
| 1.2056 | B.166 | C.10 |
| 1.2057 | B.167 | C.10 |
| 1.2058 | B.168 | C.10 |
| 1.2059 | B.169 | C.10 |
| 1.2060 | B.170 | C.10 |

TABLE 1-continued (compositions 1.1 to 1.3419):

| comp. no. | herbicide B | safener C |
|---|---|---|
| 1.2061 | B.171 | C.10 |
| 1.2062 | B.172 | C.10 |
| 1.2063 | B.173 | C.10 |
| 1.2064 | B.174 | C.10 |
| 1.2065 | B.175 | C.10 |
| 1.2066 | B.176 | C.10 |
| 1.2067 | B.177 | C.10 |
| 1.2068 | B.178 | C.10 |
| 1.2069 | B.179 | C.10 |
| 1.2070 | B.180 | C.10 |
| 1.2071 | B.181 | C.10 |
| 1.2072 | B.182 | C.10 |
| 1.2073 | B.183 | C.10 |
| 1.2074 | B.184 | C.10 |
| 1.2075 | B.185 | C.10 |
| 1.2076 | B.186 | C.10 |
| 1.2077 | B.187 | C.10 |
| 1.2078 | B.188 | C.10 |
| 1.2079 | B.189 | C.10 |
| 1.2080 | B.1 | C.11 |
| 1.2081 | B.2 | C.11 |
| 1.2082 | B.3 | C.11 |
| 1.2083 | B.4 | C.11 |
| 1.2084 | B.5 | C.11 |
| 1.2085 | B.6 | C.11 |
| 1.2086 | B.7 | C.11 |
| 1.2087 | B.8 | C.11 |
| 1.2088 | B.9 | C.11 |
| 1.2089 | B.10 | C.11 |
| 1.2090 | B.11 | C.11 |
| 1.2091 | B.12 | C.11 |
| 1.2092 | B.13 | C.11 |
| 1.2093 | B.14 | C.11 |
| 1.2094 | B.15 | C.11 |
| 1.2095 | B.16 | C.11 |
| 1.2096 | B.17 | C.11 |
| 1.2097 | B.18 | C.11 |
| 1.2098 | B.19 | C.11 |
| 1.2099 | B.20 | C.11 |
| 1.2100 | B.21 | C.11 |
| 1.2101 | B.22 | C.11 |
| 1.2102 | B.23 | C.11 |
| 1.2103 | B.24 | C.11 |
| 1.2104 | B.25 | C.11 |
| 1.2105 | B.26 | C.11 |
| 1.2106 | B.27 | C.11 |
| 1.2107 | B.28 | C.11 |
| 1.2108 | B.29 | C.11 |
| 1.2109 | B.30 | C.11 |
| 1.2110 | B.31 | C.11 |
| 1.2111 | B.32 | C.11 |
| 1.2112 | B.33 | C.11 |
| 1.2113 | B.34 | C.11 |
| 1.2114 | B.35 | C.11 |
| 1.2115 | B.36 | C.11 |
| 1.2116 | B.37 | C.11 |
| 1.2117 | B.38 | C.11 |
| 1.2118 | B.39 | C.11 |
| 1.2119 | B.40 | C.11 |
| 1.2120 | B.41 | C.11 |
| 1.2121 | B.42 | C.11 |
| 1.2122 | B.43 | C.11 |
| 1.2123 | B.44 | C.11 |
| 1.2124 | B.45 | C.11 |
| 1.2125 | B.46 | C.11 |
| 1.2126 | B.47 | C.11 |
| 1.2127 | B.48 | C.11 |
| 1.2128 | B.49 | C.11 |
| 1.2129 | B.50 | C.11 |
| 1.2130 | B.51 | C.11 |
| 1.2131 | B.52 | C.11 |
| 1.2132 | B.53 | C.11 |
| 1.2133 | B.54 | C.11 |
| 1.2134 | B.55 | C.11 |
| 1.2135 | B.56 | C.11 |
| 1.2136 | B.57 | C.11 |
| 1.2137 | B.58. | C.11 |
| 1.2138 | B.59 | C.11 |
| 1.2139 | B.60 | C.11 |
| 1.2140 | B.61 | C.11 |
| 1.2141 | B.62 | C.11 |
| 1.2142 | B.63 | C.11 |
| 1.2143 | B.64 | C.11 |
| 1.2144 | B.65 | C.11 |
| 1.2145 | B.66 | C.11 |
| 1.2146 | B.67 | C.11 |
| 1.2147 | B.68 | C.11 |
| 1.2148 | B.69 | C.11 |
| 1.2149 | B.70 | C.11 |
| 1.2150 | B.71 | C.11 |
| 1.2151 | B.72 | C.11 |
| 1.2152 | B.73 | C.11 |
| 1.2153 | B.74 | C.11 |
| 1.2154 | B.75 | C.11 |
| 1.2155 | B.76 | C.11 |
| 1.2156 | B.77 | C.11 |
| 1.2157 | B.78 | C.11 |
| 1.2158 | B.79 | C.11 |
| 1.2159 | B.80 | C.11 |
| 1.2160 | B.81 | C.11 |
| 1.2161 | B.82 | C.11 |
| 1.2162 | B.83 | C.11 |
| 1.2163 | B.84 | C.11 |
| 1.2164 | B.85 | C.11 |
| 1.2165 | B.86 | C.11 |
| 1.2166 | B.87 | C.11 |
| 1.2167 | B.88 | C.11 |
| 1.2168 | B.89 | C.11 |
| 1.2169 | B.90 | C.11 |
| 1.2170 | B.91 | C.11 |
| 1.2171 | B.92 | C.11 |
| 1.2172 | B.93 | C.11 |
| 1.2173 | B.94 | C.11 |
| 1.2174 | B.95 | C.11 |
| 1.2175 | B.96 | C.11 |
| 1.2176 | B.97 | C.11 |
| 1.2177 | B.98 | C.11 |
| 1.2178 | B.99 | C.11 |
| 1.2179 | B.100 | C.11 |
| 1.2180 | B.101 | C.11 |
| 1.2181 | B.102 | C.11 |
| 1.2182 | B.103 | C.11 |
| 1.2183 | B.104 | C.11 |
| 1.2184 | B.105 | C.11 |
| 1.2185 | B.106 | C.11 |
| 1.2186 | B.107 | C.11 |
| 1.2187 | B.108 | C.11 |
| 1.2188 | B.109 | C.11 |
| 1.2189 | B.110 | C.11 |
| 1.2190 | B.111 | C.11 |
| 1.2191 | B.112 | C.11 |
| 1.2192 | B.113 | C.11 |
| 1.2193 | B.114 | C.11 |
| 1.2194 | B.115 | C.11 |
| 1.2195 | B.116 | C.11 |
| 1.2196 | B.117 | C.11 |
| 1.2197 | B.118 | C.11 |
| 1.2198 | B.119 | C.11 |
| 1.2199 | B.120 | C.11 |
| 1.2200 | B.121 | C.11 |
| 1.2201 | B.122 | C.11 |
| 1.2202 | B.123 | C.11 |
| 1.2203 | B.124 | C.11 |
| 1.2204 | B.125 | C.11 |
| 1.2205 | B.126 | C.11 |
| 1.2206 | B.127 | C.11 |
| 1.2207 | B.128 | C.11 |
| 1.2208 | B.129 | C.11 |
| 1.2209 | B.130 | C.11 |
| 1.2210 | B.131 | C.11 |
| 1.2211 | B.132 | C.11 |
| 1.2212 | B.133 | C.11 |

TABLE 1-continued (compositions 1.1 to 1.3419):

| comp. no. | herbicide B | safener C |
|---|---|---|
| 1.2213 | B.134 | C.11 |
| 1.2214 | B.135 | C.11 |
| 1.2215 | B.136 | C.11 |
| 1.2216 | B.137 | C.11 |
| 1.2217 | B.138 | C.11 |
| 1.2218 | B.139 | C.11 |
| 1.2219 | B.140 | C.11 |
| 1.2220 | B.141 | C.11 |
| 1.2221 | B.142 | C.11 |
| 1.2222 | B.143 | C.11 |
| 1.2223 | B.144 | C.11 |
| 1.2224 | B.145 | C.11 |
| 1.2225 | B.146 | C.11 |
| 1.2226 | B.147 | C.11 |
| 1.2227 | B.148 | C.11 |
| 1.2228 | B.149 | C.11 |
| 1.2229 | B.150 | C.11 |
| 1.2230 | B.151 | C.11 |
| 1.2231 | B.152 | C.11 |
| 1.2232 | B.153 | C.11 |
| 1.2233 | B.154 | C.11 |
| 1.2234 | B.155 | C.11 |
| 1.2235 | B.156 | C.11 |
| 1.2236 | B.157 | C.11 |
| 1.2237 | B.158 | C.11 |
| 1.2238 | B.159 | C.11 |
| 1.2239 | B.160 | C.11 |
| 1.2240 | B.161 | C.11 |
| 1.2241 | B.162 | C.11 |
| 1.2242 | B.163 | C.11 |
| 1.2243 | B.164 | C.11 |
| 1.2244 | B.165 | C.11 |
| 1.2245 | B.166 | C.11 |
| 1.2246 | B.167 | C.11 |
| 1.2247 | B.168 | C.11 |
| 1.2248 | B.169 | C.11 |
| 1.2249 | B.170 | C.11 |
| 1.2250 | B.171 | C.11 |
| 1.2251 | B.172 | C.11 |
| 1.2252 | B.173 | C.11 |
| 1.2253 | B.174 | C.11 |
| 1.2254 | B.175 | C.11 |
| 1.2255 | B.176 | C.11 |
| 1.2256 | B.177 | C.11 |
| 1.2257 | B.178 | C.11 |
| 1.2258 | B.179 | C.11 |
| 1.2259 | B.180 | C.11 |
| 1.2260 | B.181 | C.11 |
| 1.2261 | B.182 | C.11 |
| 1.2262 | B.183 | C.11 |
| 1.2263 | B.184 | C.11 |
| 1.2264 | B.185 | C.11 |
| 1.2265 | B.186 | C.11 |
| 1.2266 | B.187 | C.11 |
| 1.2267 | B.188 | C.11 |
| 1.2268 | B.189 | C.11 |
| 1.2269 | B.1 | C.12 |
| 1.2270 | B.2 | C.12 |
| 1.2271 | B.3 | C.12 |
| 1.2272 | B.4 | C.12 |
| 1.2273 | B.5 | C.12 |
| 1.2274 | B.6 | C.12 |
| 1.2275 | B.7 | C.12 |
| 1.2276 | B.8 | C.12 |
| 1.2277 | B.9 | C.12 |
| 1.2278 | B.10 | C.12 |
| 1.2279 | B.11 | C.12 |
| 1.2280 | B.12 | C.12 |
| 1.2281 | B.13 | C.12 |
| 1.2282 | B.14 | C.12 |
| 1.2283 | B.15 | C.12 |
| 1.2284 | B.16 | C.12 |
| 1.2285 | B.17 | C.12 |
| 1.2286 | B.18 | C.12 |
| 1.2287 | B.19 | C.12 |
| 1.2288 | B.20 | C.12 |
| 1.2289 | B.21 | C.12 |
| 1.2290 | B.22 | C.12 |
| 1.2291 | B.23 | C.12 |
| 1.2292 | B.24 | C.12 |
| 1.2293 | B.25 | C.12 |
| 1.2294 | B.26 | C.12 |
| 1.2295 | B.27 | C.12 |
| 1.2296 | B.28 | C.12 |
| 1.2297 | B.29 | C.12 |
| 1.2298 | B.30 | C.12 |
| 1.2299 | B.31 | C.12 |
| 1.2300 | B.32 | C.12 |
| 1.2301 | B.33 | C.12 |
| 1.2302 | B.34 | C.12 |
| 1.2303 | B.35 | C.12 |
| 1.2304 | B.36 | C.12 |
| 1.2305 | B.37 | C.12 |
| 1.2306 | B.38 | C.12 |
| 1.2307 | B.39 | C.12 |
| 1.2308 | B.40 | C.12 |
| 1.2309 | B.41 | C.12 |
| 1.2310 | B.42 | C.12 |
| 1.2311 | B.43 | C.12 |
| 1.2312 | B.44 | C.12 |
| 1.2313 | B.45 | C.12 |
| 1.2314 | B.46 | C.12 |
| 1.2315 | B.47 | C.12 |
| 1.2316 | B.48 | C.12 |
| 1.2317 | B.49 | C.12 |
| 1.2318 | B.50 | C.12 |
| 1.2319 | B.51 | C.12 |
| 1.2320 | B.52 | C.12 |
| 1.2321 | B.53 | C.12 |
| 1.2322 | B.54 | C.12 |
| 1.2323 | B.55 | C.12 |
| 1.2324 | B.56 | C.12 |
| 1.2325 | B.57 | C.12 |
| 1.2326 | B.58. | C.12 |
| 1.2327 | B.59 | C.12 |
| 1.2328 | B.60 | C.12 |
| 1.2329 | B.61 | C.12 |
| 1.2330 | B.62 | C.12 |
| 1.2331 | B.63 | C.12 |
| 1.2332 | B.64 | C.12 |
| 1.2333 | B.65 | C.12 |
| 1.2334 | B.66 | C.12 |
| 1.2335 | B.67 | C.12 |
| 1.2336 | B.68 | C.12 |
| 1.2337 | B.69 | C.12 |
| 1.2338 | B.70 | C.12 |
| 1.2339 | B.71 | C.12 |
| 1.2340 | B.72 | C.12 |
| 1.2341 | B.73 | C.12 |
| 1.2342 | B.74 | C.12 |
| 1.2343 | B.75 | C.12 |
| 1.2344 | B.76 | C.12 |
| 1.2345 | B.77 | C.12 |
| 1.2346 | B.78 | C.12 |
| 1.2347 | B.79 | C.12 |
| 1.2348 | B.80 | C.12 |
| 1.2349 | B.81 | C.12 |
| 1.2350 | B.82 | C.12 |
| 1.2351 | B.83 | C.12 |
| 1.2352 | B.84 | C.12 |
| 1.2353 | B.85 | C.12 |
| 1.2354 | B.86 | C.12 |
| 1.2355 | B.87 | C.12 |
| 1.2356 | B.88 | C.12 |
| 1.2357 | B.89 | C.12 |
| 1.2358 | B.90 | C.12 |
| 1.2359 | B.91 | C.12 |
| 1.2360 | B.92 | C.12 |
| 1.2361 | B.93 | C.12 |
| 1.2362 | B.94 | C.12 |
| 1.2363 | B.95 | C.12 |
| 1.2364 | B.96 | C.12 |

TABLE 1-continued (compositions 1.1 to 1.3419):

| comp. no. | herbicide B | safener C |
|---|---|---|
| 1.2365 | B.97 | C.12 |
| 1.2366 | B.98 | C.12 |
| 1.2367 | B.99 | C.12 |
| 1.2368 | B.100 | C.12 |
| 1.2369 | B.101 | C.12 |
| 1.2370 | B.102 | C.12 |
| 1.2371 | B.103 | C.12 |
| 1.2372 | B.104 | C.12 |
| 1.2373 | B.105 | C.12 |
| 1.2374 | B.106 | C.12 |
| 1.2375 | B.107 | C.12 |
| 1.2376 | B.108 | C.12 |
| 1.2377 | B.109 | C.12 |
| 1.2378 | B.110 | C.12 |
| 1.2379 | B.111 | C.12 |
| 1.2380 | B.112 | C.12 |
| 1.2381 | B.113 | C.12 |
| 1.2382 | B.114 | C.12 |
| 1.2383 | B.115 | C.12 |
| 1.2384 | B.116 | C.12 |
| 1.2385 | B.117 | C.12 |
| 1.2386 | B.118 | C.12 |
| 1.2387 | B.119 | C.12 |
| 1.2388 | B.120 | C.12 |
| 1.2389 | B.121 | C.12 |
| 1.2390 | B.122 | C.12 |
| 1.2391 | B.123 | C.12 |
| 1.2392 | B.124 | C.12 |
| 1.2393 | B.125 | C.12 |
| 1.2394 | B.126 | C.12 |
| 1.2395 | B.127 | C.12 |
| 1.2396 | B.128 | C.12 |
| 1.2397 | B.129 | C.12 |
| 1.2398 | B.130 | C.12 |
| 1.2399 | B.131 | C.12 |
| 1.2400 | B.132 | C.12 |
| 1.2401 | B.133 | C.12 |
| 1.2402 | B.134 | C.12 |
| 1.2403 | B.135 | C.12 |
| 1.2404 | B.136 | C.12 |
| 1.2405 | B.137 | C.12 |
| 1.2406 | B.138 | C.12 |
| 1.2407 | B.139 | C.12 |
| 1.2408 | B.140 | C.12 |
| 1.2409 | B.141 | C.12 |
| 1.2410 | B.142 | C.12 |
| 1.2411 | B.143 | C.12 |
| 1.2412 | B.144 | C.12 |
| 1.2413 | B.145 | C.12 |
| 1.2414 | B.146 | C.12 |
| 1.2415 | B.147 | C.12 |
| 1.2416 | B.148 | C.12 |
| 1.2417 | B.149 | C.12 |
| 1.2418 | B.150 | C.12 |
| 1.2419 | B.151 | C.12 |
| 1.2420 | B.152 | C.12 |
| 1.2421 | B.153 | C.12 |
| 1.2422 | B.154 | C.12 |
| 1.2423 | B.155 | C.12 |
| 1.2424 | B.156 | C.12 |
| 1.2425 | B.157 | C.12 |
| 1.2426 | B.158 | C.12 |
| 1.2427 | B.159 | C.12 |
| 1.2428 | B.160 | C.12 |
| 1.2429 | B.161 | C.12 |
| 1.2430 | B.162 | C.12 |
| 1.2431 | B.163 | C.12 |
| 1.2432 | B.164 | C.12 |
| 1.2433 | B.165 | C.12 |
| 1.2434 | B.166 | C.12 |
| 1.2435 | B.167 | C.12 |
| 1.2436 | B.168 | C.12 |
| 1.2437 | B.169 | C.12 |
| 1.2438 | B.170 | C.12 |
| 1.2439 | B.171 | C.12 |
| 1.2440 | B.172 | C.12 |
| 1.2441 | B.173 | C.12 |
| 1.2442 | B.174 | C.12 |
| 1.2443 | B.175 | C.12 |
| 1.2444 | B.176 | C.12 |
| 1.2445 | B.177 | C.12 |
| 1.2446 | B.178 | C.12 |
| 1.2447 | B.179 | C.12 |
| 1.2448 | B.180 | C.12 |
| 1.2449 | B.181 | C.12 |
| 1.2450 | B.182 | C.12 |
| 1.2451 | B.183 | C.12 |
| 1.2452 | B.184 | C.12 |
| 1.2453 | B.185 | C.12 |
| 1.2454 | B.186 | C.12 |
| 1.2455 | B.187 | C.12 |
| 1.2456 | B.188 | C.12 |
| 1.2457 | B.189 | C.12 |
| 1.2458 | B.1 | C.13 |
| 1.2459 | B.2 | C.13 |
| 1.2460 | B.3 | C.13 |
| 1.2461 | B.4 | C.13 |
| 1.2462 | B.5 | C.13 |
| 1.2463 | B.6 | C.13 |
| 1.2464 | B.7 | C.13 |
| 1.2465 | B.8 | C.13 |
| 1.2466 | B.9 | C.13 |
| 1.2467 | B.10 | C.13 |
| 1.2468 | B.11 | C.13 |
| 1.2469 | B.12 | C.13 |
| 1.2470 | B.13 | C.13 |
| 1.2471 | B.14 | C.13 |
| 1.2472 | B.15 | C.13 |
| 1.2473 | B.16 | C.13 |
| 1.2474 | B.17 | C.13 |
| 1.2475 | B.18 | C.13 |
| 1.2476 | B.19 | C.13 |
| 1.2477 | B.20 | C.13 |
| 1.2478 | B.21 | C.13 |
| 1.2479 | B.22 | C.13 |
| 1.2480 | B.23 | C.13 |
| 1.2481 | B.24 | C.13 |
| 1.2482 | B.25 | C.13 |
| 1.2483 | B.26 | C.13 |
| 1.2484 | B.27 | C.13 |
| 1.2485 | B.28 | C.13 |
| 1.2486 | B.29 | C.13 |
| 1.2487 | B.30 | C.13 |
| 1.2488 | B.31 | C.13 |
| 1.2489 | B.32 | C.13 |
| 1.2490 | B.33 | C.13 |
| 1.2491 | B.34 | C.13 |
| 1.2492 | B.35 | C.13 |
| 1.2493 | B.36 | C.13 |
| 1.2494 | B.37 | C.13 |
| 1.2495 | B.38 | C.13 |
| 1.2496 | B.39 | C.13 |
| 1.2497 | B.40 | C.13 |
| 1.2498 | B.41 | C.13 |
| 1.2499 | B.42 | C.13 |
| 1.2500 | B.43 | C.13 |
| 1.2501 | B.44 | C.13 |
| 1.2502 | B.45 | C.13 |
| 1.2503 | B.46 | C.13 |
| 1.2504 | B.47 | C.13 |
| 1.2505 | B.48 | C.13 |
| 1.2506 | B.49 | C.13 |
| 1.2507 | B.50 | C.13 |
| 1.2508 | B.51 | C.13 |
| 1.2509 | B.52 | C.13 |
| 1.2510 | B.53 | C.13 |
| 1.2511 | B.54 | C.13 |
| 1.2512 | B.55 | C.13 |
| 1.2513 | B.56 | C.13 |
| 1.2514 | B.57 | C.13 |
| 1.2515 | B.58. | C.13 |
| 1.2516 | B.59 | C.13 |

TABLE 1-continued (compositions 1.1 to 1.3419):

| comp. no. | herbicide B | safener C |
|---|---|---|
| 1.2517 | B.60 | C.13 |
| 1.2518 | B.61 | C.13 |
| 1.2519 | B.62 | C.13 |
| 1.2520 | B.63 | C.13 |
| 1.2521 | B.64 | C.13 |
| 1.2522 | B.65 | C.13 |
| 1.2523 | B.66 | C.13 |
| 1.2524 | B.67 | C.13 |
| 1.2525 | B.68 | C.13 |
| 1.2526 | B.69 | C.13 |
| 1.2527 | B.70 | C.13 |
| 1.2528 | B.71 | C.13 |
| 1.2529 | B.72 | C.13 |
| 1.2530 | B.73 | C.13 |
| 1.2531 | B.74 | C.13 |
| 1.2532 | B.75 | C.13 |
| 1.2533 | B.76 | C.13 |
| 1.2534 | B.77 | C.13 |
| 1.2535 | B.78 | C.13 |
| 1.2536 | B.79 | C.13 |
| 1.2537 | B.80 | C.13 |
| 1.2538 | B.81 | C.13 |
| 1.2539 | B.82 | C.13 |
| 1.2540 | B.83 | C.13 |
| 1.2541 | B.84 | C.13 |
| 1.2542 | B.85 | C.13 |
| 1.2543 | B.86 | C.13 |
| 1.2544 | B.87 | C.13 |
| 1.2545 | B.88 | C.13 |
| 1.2546 | B.89 | C.13 |
| 1.2547 | B.90 | C.13 |
| 1.2548 | B.91 | C.13 |
| 1.2549 | B.92 | C.13 |
| 1.2550 | B.93 | C.13 |
| 1.2551 | B.94 | C.13 |
| 1.2552 | B.95 | C.13 |
| 1.2553 | B.96 | C.13 |
| 1.2554 | B.97 | C.13 |
| 1.2555 | B.98 | C.13 |
| 1.2556 | B.99 | C.13 |
| 1.2557 | B.100 | C.13 |
| 1.2558 | B.101 | C.13 |
| 1.2559 | B.102 | C.13 |
| 1.2560 | B.103 | C.13 |
| 1.2561 | B.104 | C.13 |
| 1.2562 | B.105 | C.13 |
| 1.2563 | B.106 | C.13 |
| 1.2564 | B.107 | C.13 |
| 1.2565 | B.108 | C.13 |
| 1.2566 | B.109 | C.13 |
| 1.2567 | B.110 | C.13 |
| 1.2568 | B.111 | C.13 |
| 1.2569 | B.112 | C.13 |
| 1.2570 | B.113 | C.13 |
| 1.2571 | B.114 | C.13 |
| 1.2572 | B.115 | C.13 |
| 1.2573 | B.116 | C.13 |
| 1.2574 | B.117 | C.13 |
| 1.2575 | B.118 | C.13 |
| 1.2576 | B.119 | C.13 |
| 1.2577 | B.120 | C.13 |
| 1.2578 | B.121 | C.13 |
| 1.2579 | B.122 | C.13 |
| 1.2580 | B.123 | C.13 |
| 1.2581 | B.124 | C.13 |
| 1.2582 | B.125 | C.13 |
| 1.2583 | B.126 | C.13 |
| 1.2584 | B.127 | C.13 |
| 1.2585 | B.128 | C.13 |
| 1.2586 | B.129 | C.13 |
| 1.2587 | B.130 | C.13 |
| 1.2588 | B.131 | C.13 |
| 1.2589 | B.132 | C.13 |
| 1.2590 | B.133 | C.13 |
| 1.2591 | B.134 | C.13 |
| 1.2592 | B.135 | C.13 |
| 1.2593 | B.136 | C.13 |
| 1.2594 | B.137 | C.13 |
| 1.2595 | B.138 | C.13 |
| 1.2596 | B.139 | C.13 |
| 1.2597 | B.140 | C.13 |
| 1.2598 | B.141 | C.13 |
| 1.2599 | B.142 | C.13 |
| 1.2600 | B.143 | C.13 |
| 1.2601 | B.144 | C.13 |
| 1.2602 | B.145 | C.13 |
| 1.2603 | B.146 | C.13 |
| 1.2604 | B.147 | C.13 |
| 1.2605 | B.148 | C.13 |
| 1.2606 | B.149 | C.13 |
| 1.2607 | B.150 | C.13 |
| 1.2608 | B.151 | C.13 |
| 1.2609 | B.152 | C.13 |
| 1.2610 | B.153 | C.13 |
| 1.2611 | B.154 | C.13 |
| 1.2612 | B.155 | C.13 |
| 1.2613 | B.156 | C.13 |
| 1.2614 | B.157 | C.13 |
| 1.2615 | B.158 | C.13 |
| 1.2616 | B.159 | C.13 |
| 1.2617 | B.160 | C.13 |
| 1.2618 | B.161 | C.13 |
| 1.2619 | B.162 | C.13 |
| 1.2620 | B.163 | C.13 |
| 1.2621 | B.164 | C.13 |
| 1.2622 | B.165 | C.13 |
| 1.2623 | B.166 | C.13 |
| 1.2624 | B.167 | C.13 |
| 1.2625 | B.168 | C.13 |
| 1.2626 | B.169 | C.13 |
| 1.2627 | B.170 | C.13 |
| 1.2628 | B.171 | C.13 |
| 1.2629 | B.172 | C.13 |
| 1.2630 | B.173 | C.13 |
| 1.2631 | B.174 | C.13 |
| 1.2632 | B.175 | C.13 |
| 1.2633 | B.176 | C.13 |
| 1.2634 | B.177 | C.13 |
| 1.2635 | B.178 | C.13 |
| 1.2636 | B.179 | C.13 |
| 1.2637 | B.180 | C.13 |
| 1.2638 | B.181 | C.13 |
| 1.2639 | B.182 | C.13 |
| 1.2640 | B.183 | C.13 |
| 1.2641 | B.184 | C.13 |
| 1.2642 | B.185 | C.13 |
| 1.2643 | B.186 | C.13 |
| 1.2644 | B.187 | C.13 |
| 1.2645 | B.188 | C.13 |
| 1.2646 | B.189 | C.13 |
| 1.2647 | B.1 | C.14 |
| 1.2648 | B.2 | C.14 |
| 1.2649 | B.3 | C.14 |
| 1.2650 | B.4 | C.14 |
| 1.2651 | B.5 | C.14 |
| 1.2652 | B.6 | C.14 |
| 1.2653 | B.7 | C.14 |
| 1.2654 | B.8 | C.14 |
| 1.2655 | B.9 | C.14 |
| 1.2656 | B.10 | C.14 |
| 1.2657 | B.11 | C.14 |
| 1.2658 | B.12 | C.14 |
| 1.2659 | B.13 | C.14 |
| 1.2660 | B.14 | C.14 |
| 1.2661 | B.15 | C.14 |
| 1.2662 | B.16 | C.14 |
| 1.2663 | B.17 | C.14 |
| 1.2664 | B.18 | C.14 |
| 1.2665 | B.19 | C.14 |
| 1.2666 | B.20 | C.14 |
| 1.2667 | B.21 | C.14 |
| 1.2668 | B.22 | C.14 |

TABLE 1-continued (compositions 1.1 to 1.3419):

| comp. no. | herbicide B | safener C |
|---|---|---|
| 1.2669 | B.23 | C.14 |
| 1.2670 | B.24 | C.14 |
| 1.2671 | B.25 | C.14 |
| 1.2672 | B.26 | C.14 |
| 1.2673 | B.27 | C.14 |
| 1.2674 | B.28 | C.14 |
| 1.2675 | B.29 | C.14 |
| 1.2676 | B.30 | C.14 |
| 1.2677 | B.31 | C.14 |
| 1.2678 | B.32 | C.14 |
| 1.2679 | B.33 | C.14 |
| 1.2680 | B.34 | C.14 |
| 1.2681 | B.35 | C.14 |
| 1.2682 | B.36 | C.14 |
| 1.2683 | B.37 | C.14 |
| 1.2684 | B.38 | C.14 |
| 1.2685 | B.39 | C.14 |
| 1.2686 | B.40 | C.14 |
| 1.2687 | B.41 | C.14 |
| 1.2688 | B.42 | C.14 |
| 1.2689 | B.43 | C.14 |
| 1.2690 | B.44 | C.14 |
| 1.2691 | B.45 | C.14 |
| 1.2692 | B.46 | C.14 |
| 1.2693 | B.47 | C.14 |
| 1.2694 | B.48 | C.14 |
| 1.2695 | B.49 | C.14 |
| 1.2696 | B.50 | C.14 |
| 1.2697 | B.51 | C.14 |
| 1.2698 | B.52 | C.14 |
| 1.2699 | B.53 | C.14 |
| 1.2700 | B.54 | C.14 |
| 1.2701 | B.55 | C.14 |
| 1.2702 | B.56 | C.14 |
| 1.2703 | B.57 | C.14 |
| 1.2704 | B.58. | C.14 |
| 1.2705 | B.59 | C.14 |
| 1.2706 | B.60 | C.14 |
| 1.2707 | B.61 | C.14 |
| 1.2708 | B.62 | C.14 |
| 1.2709 | B.63 | C.14 |
| 1.2710 | B.64 | C.14 |
| 1.2711 | B.65 | C.14 |
| 1.2712 | B.66 | C.14 |
| 1.2713 | B.67 | C.14 |
| 1.2714 | B.68 | C.14 |
| 1.2715 | B.69 | C.14 |
| 1.2716 | B.70 | C.14 |
| 1.2717 | B.71 | C.14 |
| 1.2718 | B.72 | C.14 |
| 1.2719 | B.73 | C.14 |
| 1.2720 | B.74 | C.14 |
| 1.2721 | B.75 | C.14 |
| 1.2722 | B.76 | C.14 |
| 1.2723 | B.77 | C.14 |
| 1.2724 | B.78 | C.14 |
| 1.2725 | B.79 | C.14 |
| 1.2726 | B.80 | C.14 |
| 1.2727 | B.81 | C.14 |
| 1.2728 | B.82 | C.14 |
| 1.2729 | B.83 | C.14 |
| 1.2730 | B.84 | C.14 |
| 1.2731 | B.85 | C.14 |
| 1.2732 | B.86 | C.14 |
| 1.2733 | B.87 | C.14 |
| 1.2734 | B.88 | C.14 |
| 1.2735 | B.89 | C.14 |
| 1.2736 | B.90 | C.14 |
| 1.2737 | B.91 | C.14 |
| 1.2738 | B.92 | C.14 |
| 1.2739 | B.93 | C.14 |
| 1.2740 | B.94 | C.14 |
| 1.2741 | B.95 | C.14 |
| 1.2742 | B.96 | C.14 |
| 1.2743 | B.97 | C.14 |
| 1.2744 | B.98 | C.14 |
| 1.2745 | B.99 | C.14 |
| 1.2746 | B.100 | C.14 |
| 1.2747 | B.101 | C.14 |
| 1.2748 | B.102 | C.14 |
| 1.2749 | B.103 | C.14 |
| 1.2750 | B.104 | C.14 |
| 1.2751 | B.105 | C.14 |
| 1.2752 | B.106 | C.14 |
| 1.2753 | B.107 | C.14 |
| 1.2754 | B.108 | C.14 |
| 1.2755 | B.109 | C.14 |
| 1.2756 | B.110 | C.14 |
| 1.2757 | B.111 | C.14 |
| 1.2758 | B.112 | C.14 |
| 1.2759 | B.113 | C.14 |
| 1.2760 | B.114 | C.14 |
| 1.2761 | B.115 | C.14 |
| 1.2762 | B.116 | C.14 |
| 1.2763 | B.117 | C.14 |
| 1.2764 | B.118 | C.14 |
| 1.2765 | B.119 | C.14 |
| 1.2766 | B.120 | C.14 |
| 1.2767 | B.121 | C.14 |
| 1.2768 | B.122 | C.14 |
| 1.2769 | B.123 | C.14 |
| 1.2770 | B.124 | C.14 |
| 1.2771 | B.125 | C.14 |
| 1.2772 | B.126 | C.14 |
| 1.2773 | B.127 | C.14 |
| 1.2774 | B.128 | C.14 |
| 1.2775 | B.129 | C.14 |
| 1.2776 | B.130 | C.14 |
| 1.2777 | B.131 | C.14 |
| 1.2778 | B.132 | C.14 |
| 1.2779 | B.133 | C.14 |
| 1.2780 | B.134 | C.14 |
| 1.2781 | B.135 | C.14 |
| 1.2782 | B.136 | C.14 |
| 1.2783 | B.137 | C.14 |
| 1.2784 | B.138 | C.14 |
| 1.2785 | B.139 | C.14 |
| 1.2786 | B.140 | C.14 |
| 1.2787 | B.141 | C.14 |
| 1.2788 | B.142 | C.14 |
| 1.2789 | B.143 | C.14 |
| 1.2790 | B.144 | C.14 |
| 1.2791 | B.145 | C.14 |
| 1.2792 | B.146 | C.14 |
| 1.2793 | B.147 | C.14 |
| 1.2794 | B.148 | C.14 |
| 1.2795 | B.149 | C.14 |
| 1.2796 | B.150 | C.14 |
| 1.2797 | B.151 | C.14 |
| 1.2798 | B.152 | C.14 |
| 1.2799 | B.153 | C.14 |
| 1.2800 | B.154 | C.14 |
| 1.2801 | B.155 | C.14 |
| 1.2802 | B.156 | C.14 |
| 1.2803 | B.157 | C.14 |
| 1.2804 | B.158 | C.14 |
| 1.2805 | B.159 | C.14 |
| 1.2806 | B.160 | C.14 |
| 1.2807 | B.161 | C.14 |
| 1.2808 | B.162 | C.14 |
| 1.2809 | B.163 | C.14 |
| 1.2810 | B.164 | C.14 |
| 1.2811 | B.165 | C.14 |
| 1.2812 | B.166 | C.14 |
| 1.2813 | B.167 | C.14 |
| 1.2814 | B.168 | C.14 |
| 1.2815 | B.169 | C.14 |
| 1.2816 | B.170 | C.14 |
| 1.2817 | B.171 | C.14 |
| 1.2818 | B.172 | C.14 |
| 1.2819 | B.173 | C.14 |
| 1.2820 | B.174 | C.14 |

TABLE 1-continued (compositions 1.1 to 1.3419):

| comp. no. | herbicide B | safener C |
|---|---|---|
| 1.2821 | B.175 | C.14 |
| 1.2822 | B.176 | C.14 |
| 1.2823 | B.177 | C.14 |
| 1.2824 | B.178 | C.14 |
| 1.2825 | B.179 | C.14 |
| 1.2826 | B.180 | C.14 |
| 1.2827 | B.181 | C.14 |
| 1.2828 | B.182 | C.14 |
| 1.2829 | B.183 | C.14 |
| 1.2830 | B.184 | C.14 |
| 1.2831 | B.185 | C.14 |
| 1.2832 | B.186 | C.14 |
| 1.2833 | B.187 | C.14 |
| 1.2834 | B.188 | C.14 |
| 1.2835 | B.189 | C.14 |
| 1.2836 | B.1 | C.15 |
| 1.2837 | B.2 | C.15 |
| 1.2838 | B.3 | C.15 |
| 1.2839 | B.4 | C.15 |
| 1.2840 | B.5 | C.15 |
| 1.2841 | B.6 | C.15 |
| 1.2842 | B.7 | C.15 |
| 1.2843 | B.8 | C.15 |
| 1.2844 | B.9 | C.15 |
| 1.2845 | B.10 | C.15 |
| 1.2846 | B.11 | C.15 |
| 1.2847 | B.12 | C.15 |
| 1.2848 | B.13 | C.15 |
| 1.2849 | B.14 | C.15 |
| 1.2850 | B.15 | C.15 |
| 1.2851 | B.16 | C.15 |
| 1.2852 | B.17 | C.15 |
| 1.2853 | B.18 | C.15 |
| 1.2854 | B.19 | C.15 |
| 1.2855 | B.20 | C.15 |
| 1.2856 | B.21 | C.15 |
| 1.2857 | B.22 | C.15 |
| 1.2858 | B.23 | C.15 |
| 1.2859 | B.24 | C.15 |
| 1.2860 | B.25 | C.15 |
| 1.2861 | B.26 | C.15 |
| 1.2862 | B.27 | C.15 |
| 1.2863 | B.28 | C.15 |
| 1.2864 | B.29 | C.15 |
| 1.2865 | B.30 | C.15 |
| 1.2866 | B.31 | C.15 |
| 1.2867 | B.32 | C.15 |
| 1.2868 | B.33 | C.15 |
| 1.2869 | B.34 | C.15 |
| 1.2870 | B.35 | C.15 |
| 1.2871 | B.36 | C.15 |
| 1.2872 | B.37 | C.15 |
| 1.2873 | B.38 | C.15 |
| 1.2874 | B.39 | C.15 |
| 1.2875 | B.40 | C.15 |
| 1.2876 | B.41 | C.15 |
| 1.2877 | B.42 | C.15 |
| 1.2878 | B.43 | C.15 |
| 1.2879 | B.44 | C.15 |
| 1.2880 | B.45 | C.15 |
| 1.2881 | B.46 | C.15 |
| 1.2882 | B.47 | C.15 |
| 1.2883 | B.48 | C.15 |
| 1.2884 | B.49 | C.15 |
| 1.2885 | B.50 | C.15 |
| 1.2886 | B.51 | C.15 |
| 1.2887 | B.52 | C.15 |
| 1.2888 | B.53 | C.15 |
| 1.2889 | B.54 | C.15 |
| 1.2890 | B.55 | C.15 |
| 1.2891 | B.56 | C.15 |
| 1.2892 | B.57 | C.15 |
| 1.2893 | B.58. | C.15 |
| 1.2894 | B.59 | C.15 |
| 1.2895 | B.60 | C.15 |
| 1.2896 | B.61 | C.15 |
| 1.2897 | B.62 | C.15 |
| 1.2898 | B.63 | C.15 |
| 1.2899 | B.64 | C.15 |
| 1.2900 | B.65 | C.15 |
| 1.2901 | B.66 | C.15 |
| 1.2902 | B.67 | C.15 |
| 1.2903 | B.68 | C.15 |
| 1.2904 | B.69 | C.15 |
| 1.2905 | B.70 | C.15 |
| 1.2906 | B.71 | C.15 |
| 1.2907 | B.72 | C.15 |
| 1.2908 | B.73 | C.15 |
| 1.2909 | B.74 | C.15 |
| 1.2910 | B.75 | C.15 |
| 1.2911 | B.76 | C.15 |
| 1.2912 | B.77 | C.15 |
| 1.2913 | B.78 | C.15 |
| 1.2914 | B.79 | C.15 |
| 1.2915 | B.80 | C.15 |
| 1.2916 | B.81 | C.15 |
| 1.2917 | B.82 | C.15 |
| 1.2918 | B.83 | C.15 |
| 1.2919 | B.84 | C.15 |
| 1.2920 | B.85 | C.15 |
| 1.2921 | B.86 | C.15 |
| 1.2922 | B.87 | C.15 |
| 1.2923 | B.88 | C.15 |
| 1.2924 | B.89 | C.15 |
| 1.2925 | B.90 | C.15 |
| 1.2926 | B.91 | C.15 |
| 1.2927 | B.92 | C.15 |
| 1.2928 | B.93 | C.15 |
| 1.2929 | B.94 | C.15 |
| 1.2930 | B.95 | C.15 |
| 1.2931 | B.96 | C.15 |
| 1.2932 | B.97 | C.15 |
| 1.2933 | B.98 | C.15 |
| 1.2934 | B.99 | C.15 |
| 1.2935 | B.100 | C.15 |
| 1.2936 | B.101 | C.15 |
| 1.2937 | B.102 | C.15 |
| 1.2938 | B.103 | C.15 |
| 1.2939 | B.104 | C.15 |
| 1.2940 | B.105 | C.15 |
| 1.2941 | B.106 | C.15 |
| 1.2942 | B.107 | C.15 |
| 1.2943 | B.108 | C.15 |
| 1.2944 | B.109 | C.15 |
| 1.2945 | B.110 | C.15 |
| 1.2946 | B.111 | C.15 |
| 1.2947 | B.112 | C.15 |
| 1.2948 | B.113 | C.15 |
| 1.2949 | B.114 | C.15 |
| 1.2950 | B.115 | C.15 |
| 1.2951 | B.116 | C.15 |
| 1.2952 | B.117 | C.15 |
| 1.2953 | B.118 | C.15 |
| 1.2954 | B.119 | C.15 |
| 1.2955 | B.120 | C.15 |
| 1.2956 | B.121 | C.15 |
| 1.2957 | B.122 | C.15 |
| 1.2958 | B.123 | C.15 |
| 1.2959 | B.124 | C.15 |
| 1.2960 | B.125 | C.15 |
| 1.2961 | B.126 | C.15 |
| 1.2962 | B.127 | C.15 |
| 1.2963 | B.128 | C.15 |
| 1.2964 | B.129 | C.15 |
| 1.2965 | B.130 | C.15 |
| 1.2966 | B.131 | C.15 |
| 1.2967 | B.132 | C.15 |
| 1.2968 | B.133 | C.15 |
| 1.2969 | B.134 | C.15 |
| 1.2970 | B.135 | C.15 |
| 1.2971 | B.136 | C.15 |
| 1.2972 | B.137 | C.15 |

TABLE 1-continued (compositions 1.1 to 1.3419):

| comp. no. | herbicide B | safener C |
|---|---|---|
| 1.2973 | B.138 | C.15 |
| 1.2974 | B.139 | C.15 |
| 1.2975 | B.140 | C.15 |
| 1.2976 | B.141 | C.15 |
| 1.2977 | B.142 | C.15 |
| 1.2978 | B.143 | C.15 |
| 1.2979 | B.144 | C.15 |
| 1.2980 | B.145 | C.15 |
| 1.2981 | B.146 | C.15 |
| 1.2982 | B.147 | C.15 |
| 1.2983 | B.148 | C.15 |
| 1.2984 | B.149 | C.15 |
| 1.2985 | B.150 | C.15 |
| 1.2986 | B.151 | C.15 |
| 1.2987 | B.152 | C.15 |
| 1.2988 | B.153 | C.15 |
| 1.2989 | B.154 | C.15 |
| 1.2990 | B.155 | C.15 |
| 1.2991 | B.156 | C.15 |
| 1.2992 | B.157 | C.15 |
| 1.2993 | B.158 | C.15 |
| 1.2994 | B.159 | C.15 |
| 1.2995 | B.160 | C.15 |
| 1.2996 | B.161 | C.15 |
| 1.2997 | B.162 | C.15 |
| 1.2998 | B.163 | C.15 |
| 1.2999 | B.164 | C.15 |
| 1.3000 | B.165 | C.15 |
| 1.3001 | B.166 | C.15 |
| 1.3002 | B.167 | C.15 |
| 1.3003 | B.168 | C.15 |
| 1.3004 | B.169 | C.15 |
| 1.3005 | B.170 | C.15 |
| 1.3006 | B.171 | C.15 |
| 1.3007 | B.172 | C.15 |
| 1.3008 | B.173 | C.15 |
| 1.3009 | B.174 | C.15 |
| 1.3010 | B.175 | C.15 |
| 1.3011 | B.176 | C.15 |
| 1.3012 | B.177 | C.15 |
| 1.3013 | B.178 | C.15 |
| 1.3014 | B.179 | C.15 |
| 1.3015 | B.180 | C.15 |
| 1.3016 | B.181 | C.15 |
| 1.3017 | B.182 | C.15 |
| 1.3018 | B.183 | C.15 |
| 1.3019 | B.184 | C.15 |
| 1.3020 | B.185 | C.15 |
| 1.3021 | B.186 | C.15 |
| 1.3022 | B.187 | C.15 |
| 1.3023 | B.188 | C.15 |
| 1.3024 | B.189 | C.15 |
| 1.3025 | B.1 | C.16 |
| 1.3026 | B.2 | C.16 |
| 1.3027 | B.3 | C.16 |
| 1.3028 | B.4 | C.16 |
| 1.3029 | B.5 | C.16 |
| 1.3030 | B.6 | C.16 |
| 1.3031 | B.7 | C.16 |
| 1.3032 | B.8 | C.16 |
| 1.3033 | B.9 | C.16 |
| 1.3034 | B.10 | C.16 |
| 1.3035 | B.11 | C.16 |
| 1.3036 | B.12 | C.16 |
| 1.3037 | B.13 | C.16 |
| 1.3038 | B.14 | C.16 |
| 1.3039 | B.15 | C.16 |
| 1.3040 | B.16 | C.16 |
| 1.3041 | B.17 | C.16 |
| 1.3042 | B.18 | C.16 |
| 1.3043 | B.19 | C.16 |
| 1.3044 | B.20 | C.16 |
| 1.3045 | B.21 | C.16 |
| 1.3046 | B.22 | C.16 |
| 1.3047 | B.23 | C.16 |
| 1.3048 | B.24 | C.16 |
| 1.3049 | B.25 | C.16 |
| 1.3050 | B.26 | C.16 |
| 1.3051 | B.27 | C.16 |
| 1.3052 | B.28 | C.16 |
| 1.3053 | B.29 | C.16 |
| 1.3054 | B.30 | C.16 |
| 1.3055 | B.31 | C.16 |
| 1.3056 | B.32 | C.16 |
| 1.3057 | B.33 | C.16 |
| 1.3058 | B.34 | C.16 |
| 1.3059 | B.35 | C.16 |
| 1.3060 | B.36 | C.16 |
| 1.3061 | B.37 | C.16 |
| 1.3062 | B.38 | C.16 |
| 1.3063 | B.39 | C.16 |
| 1.3064 | B.40 | C.16 |
| 1.3065 | B.41 | C.16 |
| 1.3066 | B.42 | C.16 |
| 1.3067 | B.43 | C.16 |
| 1.3068 | B.44 | C.16 |
| 1.3069 | B.45 | C.16 |
| 1.3070 | B.46 | C.16 |
| 1.3071 | B.47 | C.16 |
| 1.3072 | B.48 | C.16 |
| 1.3073 | B.49 | C.16 |
| 1.3074 | B.50 | C.16 |
| 1.3075 | B.51 | C.16 |
| 1.3076 | B.52 | C.16 |
| 1.3077 | B.53 | C.16 |
| 1.3078 | B.54 | C.16 |
| 1.3079 | B.55 | C.16 |
| 1.3080 | B.56 | C.16 |
| 1.3081 | B.57 | C.16 |
| 1.3082 | B.58. | C.16 |
| 1.3083 | B.59 | C.16 |
| 1.3084 | B.60 | C.16 |
| 1.3085 | B.61 | C.16 |
| 1.3086 | B.62 | C.16 |
| 1.3087 | B.63 | C.16 |
| 1.3088 | B.64 | C.16 |
| 1.3089 | B.65 | C.16 |
| 1.3090 | B.66 | C.16 |
| 1.3091 | B.67 | C.16 |
| 1.3092 | B.68 | C.16 |
| 1.3093 | B.69 | C.16 |
| 1.3094 | B.70 | C.16 |
| 1.3095 | B.71 | C.16 |
| 1.3096 | B.72 | C.16 |
| 1.3097 | B.73 | C.16 |
| 1.3098 | B.74 | C.16 |
| 1.3099 | B.75 | C.16 |
| 1.3100 | B.76 | C.16 |
| 1.3101 | B.77 | C.16 |
| 1.3102 | B.78 | C.16 |
| 1.3103 | B.79 | C.16 |
| 1.3104 | B.80 | C.16 |
| 1.3105 | B.81 | C.16 |
| 1.3106 | B.82 | C.16 |
| 1.3107 | B.83 | C.16 |
| 1.3108 | B.84 | C.16 |
| 1.3109 | B.85 | C.16 |
| 1.3110 | B.86 | C.16 |
| 1.3111 | B.87 | C.16 |
| 1.3112 | B.88 | C.16 |
| 1.3113 | B.89 | C.16 |
| 1.3114 | B.90 | C.16 |
| 1.3115 | B.91 | C.16 |
| 1.3116 | B.92 | C.16 |
| 1.3117 | B.93 | C.16 |
| 1.3118 | B.94 | C.16 |
| 1.3119 | B.95 | C.16 |
| 1.3120 | B.96 | C.16 |
| 1.3121 | B.97 | C.16 |
| 1.3122 | B.98 | C.16 |
| 1.3123 | B.99 | C.16 |
| 1.3124 | B.100 | C.16 |

TABLE 1-continued (compositions 1.1 to 1.3419):

| comp. no. | herbicide B | safener C |
|---|---|---|
| 1.3125 | B.101 | C.16 |
| 1.3126 | B.102 | C.16 |
| 1.3127 | B.103 | C.16 |
| 1.3128 | B.104 | C.16 |
| 1.3129 | B.105 | C.16 |
| 1.3130 | B.106 | C.16 |
| 1.3131 | B.107 | C.16 |
| 1.3132 | B.108 | C.16 |
| 1.3133 | B.109 | C.16 |
| 1.3134 | B.110 | C.16 |
| 1.3135 | B.111 | C.16 |
| 1.3136 | B.112 | C.16 |
| 1.3137 | B.113 | C.16 |
| 1.3138 | B.114 | C.16 |
| 1.3139 | B.115 | C.16 |
| 1.3140 | B.116 | C.16 |
| 1.3141 | B.117 | C.16 |
| 1.3142 | B.118 | C.16 |
| 1.3143 | B.119 | C.16 |
| 1.3144 | B.120 | C.16 |
| 1.3145 | B.121 | C.16 |
| 1.3146 | B.122 | C.16 |
| 1.3147 | B.123 | C.16 |
| 1.3148 | B.124 | C.16 |
| 1.3149 | B.125 | C.16 |
| 1.3150 | B.126 | C.16 |
| 1.3151 | B.127 | C.16 |
| 1.3152 | B.128 | C.16 |
| 1.3153 | B.129 | C.16 |
| 1.3154 | B.130 | C.16 |
| 1.3155 | B.131 | C.16 |
| 1.3156 | B.132 | C.16 |
| 1.3157 | B.133 | C.16 |
| 1.3158 | B.134 | C.16 |
| 1.3159 | B.135 | C.16 |
| 1.3160 | B.136 | C.16 |
| 1.3161 | B.137 | C.16 |
| 1.3162 | B.138 | C.16 |
| 1.3163 | B.139 | C.16 |
| 1.3164 | B.140 | C.16 |
| 1.3165 | B.141 | C.16 |
| 1.3166 | B.142 | C.16 |
| 1.3167 | B.143 | C.16 |
| 1.3168 | B.144 | C.16 |
| 1.3169 | B.145 | C.16 |
| 1.3170 | B.146 | C.16 |
| 1.3171 | B.147 | C.16 |
| 1.3172 | B.148 | C.16 |
| 1.3173 | B.149 | C.16 |
| 1.3174 | B.150 | C.16 |
| 1.3175 | B.151 | C.16 |
| 1.3176 | B.152 | C.16 |
| 1.3177 | B.153 | C.16 |
| 1.3178 | B.154 | C.16 |
| 1.3179 | B.155 | C.16 |
| 1.3180 | B.156 | C.16 |
| 1.3181 | B.157 | C.16 |
| 1.3182 | B.158 | C.16 |
| 1.3183 | B.159 | C.16 |
| 1.3184 | B.160 | C.16 |
| 1.3185 | B.161 | C.16 |
| 1.3186 | B.162 | C.16 |
| 1.3187 | B.163 | C.16 |
| 1.3188 | B.164 | C.16 |
| 1.3189 | B.165 | C.16 |
| 1.3190 | B.166 | C.16 |
| 1.3191 | B.167 | C.16 |
| 1.3192 | B.168 | C.16 |
| 1.3193 | B.169 | C.16 |
| 1.3194 | B.170 | C.16 |
| 1.3195 | B.171 | C.16 |
| 1.3196 | B.172 | C.16 |
| 1.3197 | B.173 | C.16 |
| 1.3198 | B.174 | C.16 |
| 1.3199 | B.175 | C.16 |
| 1.3200 | B.176 | C.16 |
| 1.3201 | B.177 | C.16 |
| 1.3202 | B.178 | C.16 |
| 1.3203 | B.179 | C.16 |
| 1.3204 | B.180 | C.16 |
| 1.3205 | B.181 | C.16 |
| 1.3206 | B.182 | C.16 |
| 1.3207 | B.183 | C.16 |
| 1.3208 | B.184 | C.16 |
| 1.3209 | B.185 | C.16 |
| 1.3210 | B.186 | C.16 |
| 1.3211 | B.187 | C.16 |
| 1.3212 | B.188 | C.16 |
| 1.3213 | B.189 | C.16 |
| 1.3214 | B.1 | C.17 |
| 1.3215 | B.2 | C.17 |
| 1.3216 | B.3 | C.17 |
| 1.3217 | B.4 | C.17 |
| 1.3218 | B.5 | C.17 |
| 1.3219 | B.6 | C.17 |
| 1.3220 | B.7 | C.17 |
| 1.3221 | B.8 | C.17 |
| 1.3222 | B.9 | C.17 |
| 1.3223 | B.10 | C.17 |
| 1.3224 | B.11 | C.17 |
| 1.3225 | B.12 | C.17 |
| 1.3226 | B.13 | C.17 |
| 1.3227 | B.14 | C.17 |
| 1.3228 | B.15 | C.17 |
| 1.3229 | B.16 | C.17 |
| 1.3230 | B.17 | C.17 |
| 1.3231 | B.18 | C.17 |
| 1.3232 | B.19 | C.17 |
| 1.3233 | B.20 | C.17 |
| 1.3234 | B.21 | C.17 |
| 1.3235 | B.22 | C.17 |
| 1.3236 | B.23 | C.17 |
| 1.3237 | B.24 | C.17 |
| 1.3238 | B.25 | C.17 |
| 1.3239 | B.26 | C.17 |
| 1.3240 | B.27 | C.17 |
| 1.3241 | B.28 | C.17 |
| 1.3242 | B.29 | C.17 |
| 1.3243 | B.30 | C.17 |
| 1.3244 | B.31 | C.17 |
| 1.3245 | B.32 | C.17 |
| 1.3246 | B.33 | C.17 |
| 1.3247 | B.34 | C.17 |
| 1.3248 | B.35 | C.17 |
| 1.3249 | B.36 | C.17 |
| 1.3250 | B.37 | C.17 |
| 1.3251 | B.38 | C.17 |
| 1.3252 | B.39 | C.17 |
| 1.3253 | B.40 | C.17 |
| 1.3254 | B.41 | C.17 |
| 1.3255 | B.42 | C.17 |
| 1.3256 | B.43 | C.17 |
| 1.3257 | B.44 | C.17 |
| 1.3258 | B.45 | C.17 |
| 1.3259 | B.46 | C.17 |
| 1.3260 | B.47 | C.17 |
| 1.3261 | B.48 | C.17 |
| 1.3262 | B.49 | C.17 |
| 1.3263 | B.50 | C.17 |
| 1.3264 | B.51 | C.17 |
| 1.3265 | B.52 | C.17 |
| 1.3266 | B.53 | C.17 |
| 1.3267 | B.54 | C.17 |
| 1.3268 | B.55 | C.17 |
| 1.3269 | B.56 | C.17 |
| 1.3270 | B.57 | C.17 |
| 1.3271 | B.58. | C.17 |
| 1.3272 | B.59 | C.17 |
| 1.3273 | B.60 | C.17 |
| 1.3274 | B.61 | C.17 |
| 1.3275 | B.62 | C.17 |
| 1.3276 | B.63 | C.17 |

TABLE 1-continued (compositions 1.1 to 1.3419):

| comp. no. | herbicide B | safener C |
|---|---|---|
| 1.3277 | B.64 | C.17 |
| 1.3278 | B.65 | C.17 |
| 1.3279 | B.66 | C.17 |
| 1.3280 | B.67 | C.17 |
| 1.3281 | B.68 | C.17 |
| 1.3282 | B.69 | C.17 |
| 1.3283 | B.70 | C.17 |
| 1.3284 | B.71 | C.17 |
| 1.3285 | B.72 | C.17 |
| 1.3286 | B.73 | C.17 |
| 1.3287 | B.74 | C.17 |
| 1.3288 | B.75 | C.17 |
| 1.3289 | B.76 | C.17 |
| 1.3290 | B.77 | C.17 |
| 1.3291 | B.78 | C.17 |
| 1.3292 | B.79 | C.17 |
| 1.3293 | B.80 | C.17 |
| 1.3294 | B.81 | C.17 |
| 1.3295 | B.82 | C.17 |
| 1.3296 | B.83 | C.17 |
| 1.3297 | B.84 | C.17 |
| 1.3298 | B.85 | C.17 |
| 1.3299 | B.86 | C.17 |
| 1.3300 | B.87 | C.17 |
| 1.3301 | B.88 | C.17 |
| 1.3302 | B.89 | C.17 |
| 1.3303 | B.90 | C.17 |
| 1.3304 | B.91 | C.17 |
| 1.3305 | B.92 | C.17 |
| 1.3306 | B.93 | C.17 |
| 1.3307 | B.94 | C.17 |
| 1.3308 | B.95 | C.17 |
| 1.3309 | B.96 | C.17 |
| 1.3310 | B.97 | C.17 |
| 1.3311 | B.98 | C.17 |
| 1.3312 | B.99 | C.17 |
| 1.3313 | B.100 | C.17 |
| 1.3314 | B.101 | C.17 |
| 1.3315 | B.102 | C.17 |
| 1.3316 | B.103 | C.17 |
| 1.3317 | B.104 | C.17 |
| 1.3318 | B.105 | C.17 |
| 1.3319 | B.106 | C.17 |
| 1.3320 | B.107 | C.17 |
| 1.3321 | B.108 | C.17 |
| 1.3322 | B.109 | C.17 |
| 1.3323 | B.110 | C.17 |
| 1.3324 | B.111 | C.17 |
| 1.3325 | B.112 | C.17 |
| 1.3326 | B.113 | C.17 |
| 1.3327 | B.114 | C.17 |
| 1.3328 | B.115 | C.17 |
| 1.3329 | B.116 | C.17 |
| 1.3330 | B.117 | C.17 |
| 1.3331 | B.118 | C.17 |
| 1.3332 | B.119 | C.17 |
| 1.3333 | B.120 | C.17 |
| 1.3334 | B.121 | C.17 |
| 1.3335 | B.122 | C.17 |
| 1.3336 | B.123 | C.17 |
| 1.3337 | B.124 | C.17 |
| 1.3338 | B.125 | C.17 |
| 1.3339 | B.126 | C.17 |
| 1.3340 | B.127 | C.17 |
| 1.3341 | B.128 | C.17 |
| 1.3342 | B.129 | C.17 |
| 1.3343 | B.130 | C.17 |
| 1.3344 | B.131 | C.17 |
| 1.3345 | B.132 | C.17 |
| 1.3346 | B.133 | C.17 |
| 1.3347 | B.134 | C.17 |
| 1.3348 | B.135 | C.17 |
| 1.3349 | B.136 | C.17 |
| 1.3350 | B.137 | C.17 |
| 1.3351 | B.138 | C.17 |
| 1.3352 | B.139 | C.17 |
| 1.3353 | B.140 | C.17 |
| 1.3354 | B.141 | C.17 |
| 1.3355 | B.142 | C.17 |
| 1.3356 | B.143 | C.17 |
| 1.3357 | B.144 | C.17 |
| 1.3358 | B.145 | C.17 |
| 1.3359 | B.146 | C.17 |
| 1.3360 | B.147 | C.17 |
| 1.3361 | B.148 | C.17 |
| 1.3362 | B.149 | C.17 |
| 1.3363 | B.150 | C.17 |
| 1.3364 | B.151 | C.17 |
| 1.3365 | B.152 | C.17 |
| 1.3366 | B.153 | C.17 |
| 1.3367 | B.154 | C.17 |
| 1.3368 | B.155 | C.17 |
| 1.3369 | B.156 | C.17 |
| 1.3370 | B.157 | C.17 |
| 1.3371 | B.158 | C.17 |
| 1.3372 | B.159 | C.17 |
| 1.3373 | B.160 | C.17 |
| 1.3374 | B.161 | C.17 |
| 1.3375 | B.162 | C.17 |
| 1.3376 | B.163 | C.17 |
| 1.3377 | B.164 | C.17 |
| 1.3378 | B.165 | C.17 |
| 1.3379 | B.166 | C.17 |
| 1.3380 | B.167 | C.17 |
| 1.3381 | B.168 | C.17 |
| 1.3382 | B.169 | C.17 |
| 1.3383 | B.170 | C.17 |
| 1.3384 | B.171 | C.17 |
| 1.3385 | B.172 | C.17 |
| 1.3386 | B.173 | C.17 |
| 1.3387 | B.174 | C.17 |
| 1.3388 | B.175 | C.17 |
| 1.3389 | B.176 | C.17 |
| 1.3390 | B.177 | C.17 |
| 1.3391 | B.178 | C.17 |
| 1.3392 | B.179 | C.17 |
| 1.3393 | B.180 | C.17 |
| 1.3394 | B.181 | C.17 |
| 1.3395 | B.182 | C.17 |
| 1.3396 | B.183 | C.17 |
| 1.3397 | B.184 | C.17 |
| 1.3398 | B.185 | C.17 |
| 1.3399 | B.186 | C.17 |
| 1.3400 | B.187 | C.17 |
| 1.3401 | B.188 | C.17 |
| 1.3402 | B.189 | C.17 |
| 1.3403 | — | C.1 |
| 1.3404 | — | C.2 |
| 1.3405 | — | C.3 |
| 1.3406 | — | C.4 |
| 1.3407 | — | C.5 |
| 1.3408 | — | C.6 |
| 1.3409 | — | C.7 |
| 1.3410 | — | C.8 |
| 1.3411 | — | C.9 |
| 1.3412 | — | C.10 |
| 1.3413 | — | C.11 |
| 1.3414 | — | C.12 |
| 1.3415 | — | C.13 |
| 1.3416 | — | C.14 |
| 1.3417 | — | C.15 |
| 1.3418 | — | C.16 |
| 1.3419 | — | C.17 |

The specific number for each single composition is deductible as follows:

Composition 1.777 for example comprises the phenylpyridine of formula (I.a.200), cloransulam-methyl (B.21) and cyprosulfamide (C.4) (see table 1, entry 1.777; as well as table B, entry B.21 and table C, entry C.4).

Composition 2.777 for example comprises the phenylpyridine of formula (I.a.207) (see the definition for compositions 2.1 to 2.3419 below), cloransulam-methyl (B.21) and cyprosulfamide (C.4) (see table 1, entry 1.777; as well as table B, entry B.21 and table C, entry C.4).

Composition 7.777 for example comprises saflufenacil (B.92) (see the definition for compositions 7.1 to 7.3383 below), and the compound (I.a.200), cloransulam-methyl (B.21) and cyprosulfamide (C.4) (see table 1, entry 1.777; as well as table B, entry B.21 and table C, entry C.4).

Also especially preferred are compositions 2.1. to 2.3419 which differ from the corresponding compositions 1.1 to 1.3419 only in that they comprise as the active compound A (I.a.207).

Also especially preferred are compositions 3.1. to 3.3419 which differ from the corresponding compositions 1.1 to 1.3419 only in that they comprise as the active compound A (I.a.214).

Also especially preferred are compositions 4.1. to 4.3419 which differ from the corresponding compositions 1.1 to 1.3419 only in that they comprise as the active compound A (I.a.228).

Also especially preferred are compositions 5.1. to 5.3419 which differ from the corresponding compositions 1.1 to 1.3419 only in that they comprise as the active compound A (I.a.234).

Also especially preferred are compositions 6.1. to 6.3419 which differ from the corresponding compositions 1.1 to 1.3419 only in that they additionally comprise B.88 as further herbicide B.

Also especially preferred are compositions 7.1. to 7.3419 which differ from the corresponding compositions 1.1 to 1.3419 only in that they additionally comprise B.92 as further herbicide B.

Also especially preferred are compositions 8.1. to 8.3419 which differ from the corresponding compositions 1.1 to 1.3419 only in that they additionally comprise B.95 as further herbicide B.

Also especially preferred are compositions 9.1. to 9.3419 which differ from the corresponding compositions 1.1 to 1.3419 only in that they additionally comprise B.116 as further herbicide B.

Also especially preferred are compositions 10.1. to 10.3419 which differ from the corresponding compositions 1.1 to 1.3419 only in that they additionally comprise B.125 as further herbicide B.

Also especially preferred are compositions 11.1. to 11.3419 which differ from the corresponding compositions 1.1 to 1.3419 only in that they additionally comprise B.151 as further herbicide B.

Also especially preferred are compositions 12.1. to 12.3419 which differ from the corresponding compositions 1.1 to 1.3419 only in that they additionally comprise B.88 and B.116 as further herbicides B.

Also especially preferred are compositions 13.1. to 13.3419 which differ from the corresponding compositions 1.1 to 1.3419 only in that they additionally comprise B.92 and B.116 as further herbicides B.

Also especially preferred are compositions 14.1. to 14.3419 which differ from the corresponding compositions 1.1 to 1.3419 only in that they additionally comprise B.95 and B.116 as further herbicides B.

Also especially preferred are compositions 15.1. to 15.3419 which differ from the corresponding compositions 1.1 to 1.3419 only in that they additionally comprise B.116 and B.125 as further herbicides B.

Also especially preferred are compositions 16.1. to 16.3419 which differ from the corresponding compositions 1.1 to 1.3419 only in that they additionally comprise B.116 and B.151 as further herbicides B.

Also especially preferred are compositions 17.1. to 17.3419 which differ from the corresponding compositions 1.1 to 1.3419 only in that they additionally comprise B.88, B.92 and B.116 as further herbicides B.

Also especially preferred are compositions 18.1. to 18.3419 which differ from the corresponding compositions 1.1 to 1.3419 only in that they additionally comprise B.95, B.92 and B.116 as further herbicides B.

Also especially preferred are compositions 19.1. to 19.3419 which differ from the corresponding compositions 1.1 to 1.3419 only in that they additionally comprise B.92, B.116 and B.125 as further herbicides B.

Also especially preferred are compositions 20.1. to 20.3419 which differ from the corresponding compositions 1.1 to 1.3419 only in that they additionally comprise B.92, B.116 and B.151 as further herbicides B.

The invention also relates to agrochemical compositions comprising at least an auxiliary and at least one phenylpyridine of formula (I) according to the invention.

An agrochemical composition comprises a pesticidally effective amount of a phenylpyridine of formula (I). The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific phenylpyridine of formula (I) used.

The phenylpyridines of formula (I) and their salts can be converted into customary types of agrochemical compositions, e. g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, 6$^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof.

Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinyl-alcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetaines and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the phenylpyridines of formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidones, polyvinylacetates, polyvinyl alcohols, polyacrylates, biological or synthetic waxes, and cellulose ethers.

Examples for agrochemical composition types and their preparation are:

i) Water-Soluble Concentrates (SL, LS)

10-60 wt % of a phenylpyridine of formula (I) or a herbicidal composition comprising at least one phenylpyridine of formula (I) (component A) and at least one further compound selected from the herbicidal compounds B (component B) and safeners C (component C) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a phenylpyridine of formula (I) or a herbicidal composition comprising at least one phenylpyridine of formula (I) (component A) and at least one further compound selected from the herbicidal compounds B (component B) and safeners C (component C) according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a phenylpyridine of formula (I) or a herbicidal composition comprising at least one phenylpyridine of formula (I) (component A) and at least one further compound selected from the herbicidal compounds B (component B) and safeners C (component C) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a phenylpyridine of formula (I) or a herbicidal composition comprising at least one phenylpyridine of formula (I) (component A) and at least one further compound selected from the herbicidal compounds B (component B) and safeners C (component C) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a phenylpyridine of formula (I) or a herbicidal composition comprising at least one phenylpyridine of formula (I) (component A) and at least one further compound selected from the herbicidal compounds B (component B) and safeners C (component C) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a phenylpyridine of formula (I) or a herbicidal composition comprising at least one phenylpyridine of formula (I) (component A) and at least one further compound selected from the herbicidal compounds B (component B) and safeners C (component C) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a phenylpyridine of formula (I) or a herbicidal composition comprising at least one phenylpyridine of formula (I) (component A) and at least one further compound selected from the herbicidal compounds B (component B) and safeners C (component C) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a phenylpyridine of formula (I) or a herbicidal composition comprising at least one phenylpyridine of formula (I) (component A) and at least one further compound selected from the herbicidal compounds B (component B) and safeners C (component C) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a phenylpyridine of formula (I) or a herbicidal composition comprising at least one phenylpyridine of formula (I) (component A) and at least one further compound selected from the herbicidal compounds B (component B) and safeners C (component C) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a phenylpyridine of formula (I) or a herbicidal composition comprising at least one phenylpyridine of formula (I) (component A) and at least one further compound selected from the herbicidal compounds B (component B) and safeners C (component C) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a phenylpyridine of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of a phenylpyridine of formula (I) or a herbicidal composition comprising at least one phenylpyridine of formula (I) (component A) and at least one further compound selected from the herbicidal compounds B (component B) and safeners C (component C)) according to the invention are ground finely and mixed intimately with solid carrier (e.g. finely divided kaolin) ad 100 wt %.

x) Granules (GR, FG)

0.5-30 wt % of a phenylpyridine of formula (I) or a herbicidal composition comprising at least one phenylpyridine of formula (I) (component A) and at least one further compound selected from the herbicidal compounds B (component B) and safeners C (component C) according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a phenylpyridine of formula (I) or a herbicidal composition comprising at least one phenylpyridine of formula (I) (component A) and at least one further compound selected from the herbicidal compounds B (component B) and safeners C (component C) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions and/or herbicidal compositions comprising generally comprise between 0.01 and 95%, preferably between 0.1 and 90%, and in particular between 0.5 and 75%, by weight of the phenylpyridine of formula (I). The phenylpyridines of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying phenylpyridines of formula (I), agrochemical compositions and/or herbicidal compositions thereof, on to plant propagation material, especially seeds, include dressing, coating, pelleting, dusting, soaking and in-furrow application methods of the propagation material. Preferably, phenylpyridines of formula (I), agrochemical compositions and/or herbicidal compositions thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the phenylpyridines of formula (I), the agrochemical compositions and/or the herbicidal compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the phenylpyridines of formula (I) according to the invention, the agrochemical compositions and/or the herbicidal compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. components comprising phenylpyridines of formula (I) and optionally active substances from the groups B and/or C), may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g components comprising phenylpyridines of formula (I) and optionally active substances from the groups B and/or C), can be applied jointly (e.g. after tank mix) or consecutively.

The phenylpyridines of formula (I), are suitable as herbicides. They are suitable as such, as an appropriately formulated composition (agrochemical composition) or as an herbicidal composition in combination with at least one further compound selected from the herbicidal active compounds B (component B) and safeners C (component C).

The phenylpyridines of formula (I), or the agrochemical compositions and/or herbicidal compositions comprising the phenylpyridines of formula (I), control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The phenylpyridines of formula (I), or the agrochemical compositions and/or the herbicidal compositions comprising them, are applied to the plants mainly by spraying the leaves. Here, the application can be carried out using, for example, water as carrier by customary spraying techniques using spray liquor amounts of from about 100 to 1000 l/ha (for example from 300 to 400 l/ha). The phenylpyridines of formula (I), or the agrochemical compositions and/or the herbicidal compositions comprising them, may also be applied by the low-volume or the ultra-low-volume method, or in the form of microgranules.

Application of the phenylpyridines of formula (I), or the agrochemical compositions and/or the herbicidal compositions comprising them, can be done before, during and/or after, preferably during and/or after, the emergence of the undesirable plants.

The phenylpyridines of formula (I), or the agrochemical compositions and/or the herbicidal compositions comprising them, can be applied pre-, post-emergence or pre-plant, or together with the seed of a crop plant. It is also possible to apply the phenylpyridines of formula (I), or the agrochemical compositions and/or the herbicidal compositions comprising them, by applying seed, pretreated with the phenylpyridines of formula (I), or the agrochemical compositions and/or the herbicidal compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the phenylpyridines of formula (I), or the agrochemical compositions and/or the herbicidal compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the phenylpyridines of formula (I), or the agrochemical compositions and/or the herbicidal compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the phenylpyridines of formula (I), component B and, if appropriate, component C without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha of active substance (a.s.).

In another embodiment of the invention, the application rate of the phenylpyridines of formula (I), component B and, if appropriate, component C, is from 0.001 to 3 kg/ha, preferably from 0.005 to 2.5 kg/ha and in particular from 0.01 to 2 kg/ha of active substance (a.s.).

In another preferred embodiment of the invention, the rates of application of the phenylpyridines of formula (I) according to the present invention (total amount of phenylpyridines of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the phenylpyridines of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the phenylpyridines of formula (I) is 0.1 to 1000 g/ha, preferably 1 to 750 g/ha, more preferably 5 to 500 g/ha.

The required application rates of herbicidal compounds B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safeners C are generally in the range of from 0.0005 kg/ha to 2.5 kg/ha and preferably in the range of from 0.005 kg/ha to 2 kg/ha or 0.01 kg/ha to 1.5 kg/h of a.s.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the phenylpyridines of formula (I), component B and, if appropriate, component C are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

In case of herbicidal compositions according to the present invention it is immaterial whether the phenylpyridines of formula (I), and the further component B and/or the component C are formulated and applied jointly or separately.

In the case of separate application it is of minor importance, in which order the application takes place. It is only necessary, that the phenylpyridines of formula (I), and the further component B and/or the component C are applied in a time frame that allows simultaneous action of the active ingredients on the plants, preferably within a timeframe of at most 14 days, in particular at most 7 days.

Depending on the application method in question, the phenylpyridines of formula (I), or the agrochemical compositions and/or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticum aestivum, Triticale, Triticum durum, Vicia faba, Vitis vinifera* and *Zea mays.*

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), *Triticale, Triticum aestivum, Triticum durum, Vicia faba, Vitis vinifera* and *Zea mays.*

Especially preferred crops are crops of cereals, corn, soybeans, rice, oilseed rape, cotton, potatoes, peanuts or permanent crops.

The phenylpyridines of formula (I) according to the invention, or the agrochemical compositions and/or herbicidal compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modi-fied plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the phenylpyridines of formula (I) according to the invention, or the agrochemical compositions and/or herbicidal compositions comprising them, are also suitable for the defoliation and/or desiccation of plant parts, for which crop plants such as cotton, potato, oilseed rape, sunflower, soybean or field beans, in particular cotton, are suitable. In this regard, agrochemical compositions and/or herbicidal compositions for the desiccation and/or defoliation of plants, processes for preparing these agrochemical compositions and/or herbicidal compositions and methods for desiccating and/or defoliating plants using the phenylpyridines of formula (I) have been found.

As desiccants, the phenylpyridines of formula (I) are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The preparation of the phenylpyridines of formula (I) is illustrated by examples; however, the subject matter of the present invention is not limited to the examples given.

A PREPARATION EXAMPLES

Example 1

Methyl 2-[2-chloro-5-[3-chloro-5-(trifluoromethyl)-2-pyridyl]-4-fluoro-phenoxy]-2-methoxy-acetate (I.a.200)

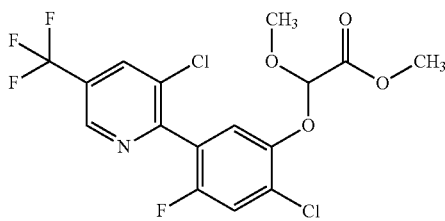 [SMILES: COC(=O)C(OC)Oc1cc(-c2ncc(C(F)(F)F)cc2Cl)c(F)cc1Cl]

1.5 g (4.60 mmol) 2-chloro-5-[3-chloro-5-(trifluoromethyl)-2-pyridyl]-4-fluoro-phenol (CAS180153-43-9) was dissolved in 50 ml dimethylformamide, 1.91 g (13.8 mmol) $K_2CO_3$ was added and after stirring for 5 min at room temperature 1.68 g (9.20 mmol) methyl 2-chloro-2-methoxy-acetate (CAS 13157-96-5) dissolved in 5 ml DMF was added. The suspension was heated for 12 h to 50° C. After cooling the suspension was filtered, the filtrate washed with ethylacetate and the combined liquid phases evaporated. The residue was 1.17 g methyl 2-[2-chloro-5-[3-chloro-5-(trifluoromethyl)-2-pyridyl]-4-fluoro-phenoxy]-2-methoxy-acetate as a colorless oil.

$^1$H-NMR (d$^6$-DMSO, ppm): 9.1 (s, 1H); 8.7 (s, 1H); 7.8 (d, 1H); 7.5 (d, 1H); 5.9 (s, 1H); 3.8 (s, 3H); 3.6 (s, 3H).

m/z=428.1; Rt=1.332 min

Example 2

2-[2-chloro-5-[3-chloro-5-(trifluoromethyl)-2-pyridyl]-4-fluoro-phenoxy]-2-ethoxy-acetic acid (I.a.232)

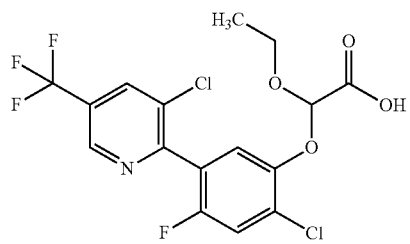 [SMILES: CCOC(Oc1cc(-c2ncc(C(F)(F)F)cc2Cl)c(F)cc1Cl)C(=O)O]

300 mg (0.66 mmol) ethyl 2-[2-chloro-5-[3-chloro-5-(trifluoromethyl)-2-pyridyl]-4-fluoro-phenoxy]-2-ethoxy-acetate, dissolved in 3 ml tetrahydrofurane, was added to 79 mg (3.3 mmol) lithium hydroxide in 3 ml water. The solution was stirred for 12 h at room temperature. The solvents were evaporated and the residue dissolved in water. The aqueous phase was acidified with 1N HCl and extracted with dichloromethane. The organic phase was evaporated resulting in 281 mg 2-[2-chloro-5-[3-chloro-5-(trifluoromethyl)-2-pyridyl]-4-fluoro-phenoxy]-2-ethoxy-acetic acid as colorless oil.

$^1$H-NMR (d$^6$-DMSO, ppm): 9.1 (s, 1H); 8.7 (s, 1H); 7.6 (d, 1H); 7.3 (d, 1H); 5.1 (s, 1H); 3.8 (m, 1H); 3.6 (m, 1H); 1.1 (t, 3H).

m/z=429.5; Rt=1.218 min

Example 3

Ethyl 2-[2-chloro-5-[3-chloro-5-(trifluoromethyl)-2-pyridyl]-4-fluoro-phenoxy]-2-ethoxy-acetate (I.a.234)

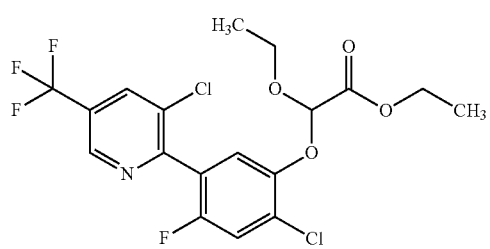 [SMILES: CCOC(=O)C(OCC)Oc1cc(-c2ncc(C(F)(F)F)cc2Cl)c(F)cc1Cl]

1.0 g (3.07 mmol) 2-chloro-5-[3-chloro-5-(trifluoromethyl)-2-pyridyl]-4-fluoro-phenol (CAS 180153-43-9) was dissolved in 35 ml dimethylformamide, 1.27 g (9.20 mmol) $K_2CO_3$ was added and after stirring for 5 min at room temperature 1.02 g (6.12 mmol) ethyl 2-chloro-2-ethoxy-acetate (CAS 34006-60-5) dissolved in 5 ml dimethylformamide was added. The suspension was heated for 12 h to 50° C. After cooling the suspension was filtered, the filtrate washed with ethylacetate and the combined organic phases evaporated. The residue was 1.17 g ethyl 2-[2-chloro-5-[3-chloro-5-(trifluoromethyl)-2-pyridyl]-4-fluoro-phenoxy]-2-ethoxy-acetate as a colorless oil.

$^1$H-NMR (d$^6$-DMSO, ppm): 9.1 (s, 1H); 8.7 (s, 1H); 7.7 (d, 1H); 7.4 (d, 1H); 5.9 (s, 1H); 4.2 (q, 2H); 3.8 (m, 2H); 1.2 (m, 6H).

m/z=456.6; Rt=1.421 min

Example 4

2-[2-chloro-5-[3-chloro-5-(trifluoromethyl)-2-pyridyl]-4-fluoro-phenoxy]-2-ethoxy-N-methylsulfonyl-acetamide (I.a.261)

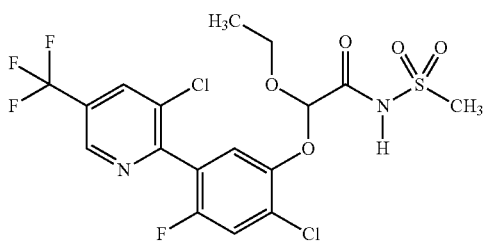 [SMILES: CCOC(Oc1cc(-c2ncc(C(F)(F)F)cc2Cl)c(F)cc1Cl)C(=O)NS(C)(=O)=O]

81 mg (0.19 mmol) 2-[2-chloro-5-[3-chloro-5-(trifluoromethyl)-2-pyridyl]-4-fluoro-phenoxy]-2-ethoxy-acetic acid was dissolved in 3 ml tetrahydrofurane. 62 mg (0.38 mmol) 1,1-carbonyldiimidazole was added and the solution heated to reflux for 1 h. After cooling 35 mg (0.38 mmol) methanesulfonamide and 58 mg (0.38 mmol) diazabicycloundecene was added and the solution was stirred for 12 h at room temperature. The solution was added to 10% aqueous HCl and extracted with methyl-tert-butylether. The organic phase was evaporated resulting in 80 mg 2-[2-chloro-5-[3-chloro-5-(trifluoromethyl)-2-pyridyl]-4-fluoro-phenoxy]-2-ethoxy-N-methylsulfonyl-acetamide 5 as colorless oil.

$^1$H-NMR (d$^6$-DMSO, ppm): 9.1 (s, 1H); 8.7 (s, 1H); 7.8 (d, 1H); 7.3 (d, 1H); 6.8 (s, 1H); 5.1 (s, 1H); 3.8 (m, 1H); 3.6 (m, 1H); 2.5 (s, 3H); 1.1 (m, 3H).

m/z=506.5; Rt=1.203 min

Example 5

Methyl 2-[2-chloro-5-[3-chloro-5-(trifluoromethyl)-2-pyridyl]-4-fluoro-phenoxy]-2-methylsulfanyl-acetate

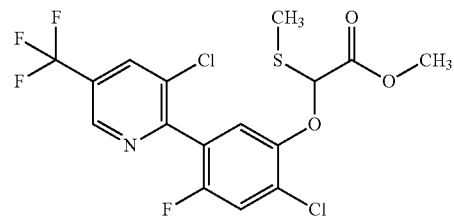 [SMILES: COC(=O)C(Oc1cc(-c2ncc(C(F)(F)F)cc2Cl)c(F)cc1Cl)SC]

300 mg (0.92 mmol) 2-chloro-5-[3-chloro-5-(trifluoromethyl)-2-pyridyl]-4-fluoro-phenol (CAS180153-43-9) was dissolved in 10 ml dimethylformamide, 267 mg (1.92 mmol) K$_2$CO$_3$ was added and after stirring for 5 min at room temperature 320 mg (1.61 mmol) methyl 2-chloro-2-thiomethoxy-acetate (CAS 62383-81-7) dissolved in 5 ml DMF was added. The suspension was heated for 12 h to 50° C. After cooling the suspension was filtered, the filtrate washed with ethylacetate and the combined liquid phases evaporated. The residue was 410 mg methyl 2-[2-chloro-5-[3-chloro-5-(trifluoromethyl)-2-pyridyl]-4-fluoro-phenoxy]-2-methylsulfanyl-acetate as a colorless oil.

$^1$H-NMR (d$^6$-DMSO, ppm): 8.9 (s, 1H); 8.1 (s, 1H); 7.4 (d, 1H); 7.2 (d, 1H); 5.6 (s, 1H); 3.9 (s, 3H); 2.3 (s, 3H).

m/z=443.9; Rt=1.372 min

The compounds listed below in table 2 can be prepared similarly to the examples mentioned above:

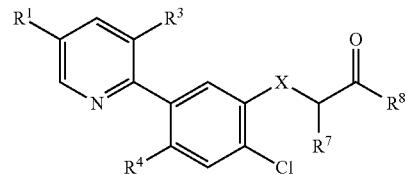

(I), wherein R$^2$ is H, R$^5$ is Cl, R$^6$ is H and Y is O

TABLE 2

| Ex | R$^1$ | R$^3$ | R$^4$ | R$^7$ | R$^8$ | X | m/z | R$_t$ [min] |
|---|---|---|---|---|---|---|---|---|
| 6 | Cl | Cl | H | OCH$_3$ | OCH$_3$ | O | 377.7 | 1.296 |
| 7 | CHF$_2$ | Cl | F | OCH$_3$ | OCH$_3$ | O | 409.3 | 1.348 |
| 8 | CF$_3$ | F | F | OCH$_3$ | OCH$_3$ | O | 411.1 | 1.212 |
| 9 | CF$_3$ | F | F | OCH$_3$ | NHSO$_2$CH$_3$ | O | 474.1 | 1.117 |
| 10 | CF$_3$ | Cl | H | OCH$_3$ | OCH$_3$ | O | 409.7 | 1.318 |
| 11 | CF$_3$ | Cl | F | OCH$_3$ | OH | O | 413.8 | 1.17 |
| 12 | CF$_3$ | Cl | F | OCH$_3$ | OCH$_2$CH$_3$ | O | 441.8 | 1.358 |
| 13 | CF$_3$ | Cl | F | OCH$_3$ | OCH$_2$CH$_2$CH$_3$ | O | 455.9 | 1.404 |
| 14 | CF$_3$ | Cl | F | OCH$_3$ | OCH(CH$_2$CH$_3$)$_2$ | O | 483.8 | 1.491 |
| 15 | CF$_3$ | Cl | F | OCH$_3$ | OCH$_2$C(CH$_3$)CH$_2$ | O | 467.8 | 1.418 |
| 16 | CF$_3$ | Cl | F | OCH$_3$ | OCH$_2$CH=CH$_2$ | O | 453.9 | 1.374 |
| 17 | CF$_3$ | Cl | F | OCH$_3$ | OCH$_2$C≡CH | O | 451.9 | 1.328 |
| 18 | CF$_3$ | Cl | F | OCH$_3$ | OCH$_2$C≡CCH$_3$ | O | 465.9 | 1.355 |
| 19 | CF$_3$ | Cl | F | OCH$_3$ | OCH$_2$CH$_2$CH$_2$C≡CH | O | 481.3 | 1.415 |
| 20 | CF$_3$ | Cl | F | OCH$_3$ | OCH$_2$CHF$_2$ | O | 477.8 | 1.334 |
| 21 | CF$_3$ | Cl | F | OCH$_3$ | OCH$_2$CH$_2$Cl | O | 475.7 | 1.35 |
| 22 | CF$_3$ | Cl | F | OCH$_3$ | OCH$_2$CHCl$_2$ | O | 511.8 | 1.401 |
| 23 | CF$_3$ | Cl | F | OCH$_3$ | OCH$_2$CH$_2$OCH$_3$ | O | 471.8 | 1.312 |
| 24 | CF$_3$ | Cl | F | OCH$_3$ | OCH$_2$CH$_2$CH$_2$OCH$_3$ | O | 485.9 | 1.325 |
| 25 | CF$_3$ | Cl | F | OCH$_3$ | OCH$_2$CH$_2$OCH$_2$CH$_3$ | O | 485.9 | 1.364 |
| 26 | CF$_3$ | Cl | F | OCH$_3$ | OCH$_2$CH$_2$OCH(CH$_3$)$_2$ | O | 500 | 1.409 |
| 27 | CF$_3$ | Cl | F | OCH$_3$ | OCH$_2$CH(OCH$_3$)$_2$ | O | 469.8 | 1.323 |

TABLE 2-continued

| Ex | R¹ | R³ | R⁴ | R⁷ | R⁸ | X | m/z | R_t [min] |
|---|---|---|---|---|---|---|---|---|
| 28 | CF₃ | Cl | F | OCH₃ | OCH₂CH(OCH₂CH₃)₂ | O | 483.9 | 1.408 |
| 29 | CF₃ | Cl | F | OCH₃ | OCH₂COOCH₃ | O | 485.8 | 1.228 |
| 30 | CF₃ | Cl | F | OCH₃ | OCH(CH₃)COOCH₃ | O | 499.9 | 1.331 |
| 31 | CF₃ | Cl | F | OCH₃ | O—c-C₄H₇ | O | 467.9 | 1.425 |
| 32 | CF₃ | Cl | F | OCH₃ | OCH₂—c-C₃H₅ | O | 467.9 | 1.401 |
| 33 | CF₃ | Cl | F | OCH₃ | OCH₂—c-C₄H₇ | O | 481.9 | 1.453 |
| 34 | CF₃ | Cl | F | OCH₃ | OCH₂-(2-furyl) | O | 493.8 | 1.373 |
| 35 | CF₃ | Cl | F | OCH₃ | OCH₂C₆H₅ | O | 503.9 | 1.42 |
| 36 | CF₃ | Cl | F | OCH₃ | O[(2-OCH₂CH₃)C₆H₄] | O | 533.6 | 1.413 |
| 37 | CF₃ | Cl | F | OCH₃ | OCH₃ | S | 443.9 | 1.349 |
| 38 | CF₃ | Cl | F | OCH₃ | NHCH₃ | O | 90 | 1.18 |
| 39 | CF₃ | Cl | F | OCH₃ | NHCH₂C≡CH | O | 450.8 | 1.224 |
| 40 | CF₃ | Cl | F | OCH₃ | NHSO₂CH₃ | O | 491.1 | 1.207 |
| 41 | CF₃ | Cl | F | OCH₃ | NHSO₂N(CH₃)(CH(CH₂)₂) | O | 547.9 | 1.313 |
| 42 | CF₃ | Cl | F | SCH₃ | OCH₃ | S | 460 | 1.441 |
| 43 | CF₃ | Cl | F | OCH₃ | NCH₂[(3-OCH₃)C₆H₄] | O | 533 | 1.332 |
| 44 | CF₃ | Cl | F | OCH₃ | NCH₂[(4-OCH₃)C₆H₄] | O | 533 | 1.327 |
| 45 | CF₃ | Cl | F | OCH₃ | NCH₂C₆H₅ | O | 503 | 1.337 |
| 46 | CF₃ | Cl | F | OCH₃ | NCH₂CH₂CH₂OCH₃ | O | 485 | 1.242 |
| 47 | CF₃ | Cl | F | OCH₃ | NCH₂CH₂OCH₃ | O | 471 | 1.219 |
| 48 | CF₃ | Cl | F | OCH₃ | NCH₂—c-C₃H₅ | O | 467 | 1.301 |
| 49 | CF₃ | Cl | F | OCH₃ | NCH₂CH=CH₂ | O | 453 | 1.264 |
| 50 | CF₃ | Cl | F | OCH₃ | NCH₂CH₃ | O | 441 | 1.237 |
| 51 | CF₃ | Cl | F | OCH₃ | N(CH₃)CH₂CN | O | 465.9 | 1.224 |
| 52 | CF₃ | Cl | F | OCH₃ | 2,5-dihydropyrrol-1-yl | O | 465 | 1.265 |
| 53 | CF₃ | Cl | F | OCH₃ | N(CH₃)CH(CH₃)₂ | O | 469 | 1.329 |
| 54 | CF₃ | Cl | F | OCH₃ | N(CH₃)CH₂CH=CH₂ | O | 467 | 1.312 |
| 55 | CF₃ | Cl | F | OCH₃ | N(CH₃)CH₂CH₂CH₃ | O | 469 | 1.334 |
| 56 | CF₃ | Cl | F | OCH₃ | N(CH₃)CH₂C≡CH | O | 465 | 1.274 |
| 57 | CF₃ | Cl | F | OCH₃ | N(CH₃)CH₂CH₂OCH₃ | O | 485 | 1.253 |
| 58 | CF₃ | Cl | F | OCH₃ | thiomorpholine | O | 498.9 | 1.322 |
| 59 | CF₃ | Cl | F | OCH₃ | 1-piperidyl | O | 481 | 1.356 |
| 60 | CF₃ | Cl | F | OCH₃ | O(tetrahydropyran-4-yl) | O | 498 | 1.319 |
| 61 | CF₃ | Cl | F | OCH₃ | O—c-C₃H₅ | O | 453.9 | 1.357 |
| 62 | CF₃ | Cl | F | OCH₃ | O—c-C₆H₁₁ | O | 496 | 1.5 |
| 63 | CF₃ | Cl | F | OCH₃ | O—c-C₅H₉ | O | 481.9 | 1.453 |
| 64 | CF₃ | Cl | F | OCH₃ | OCH(CH₃)₂ | O | 456 | 1.389 |
| 65 | CF₃ | Cl | F | OCH₃ | NH₂ | O | 412.9 | 1.133 |
| 66 | CF₃ | Cl | F | OCH₃ | OCH₂COOCH(CH₃)₂ | O | 514 | 1.399 |
| 67 | CF₃ | Cl | F | OCH₃ | OCH₂COOCH₂CH₃ | O | 500 | 1.358 |
| 68 | CF₃ | Cl | F | OCH₃ | OCH₂CH(CH₃)₂ | O | 470.1 | 1.466 |
| 69 | CF₃ | Cl | F | OCH₃ | morpholino | O | 483 | 1.224 |
| 70 | CF₃ | Cl | F | OCH₃ | pyrrolidin-1-yl | O | 467 | 1.272 |
| 71 | CF₃ | Cl | F | OCH₃ | azetidin-1-yl | O | 453 | 1.228 |
| 72 | CF₃ | Cl | F | OCH₃ | N(CH₃)₂ | O | 441 | 1.229 |
| 73 | CF₃ | Cl | F | OCH₃ | 1-methyl-4-piperidyl | O | 511 | 1.009 |
| 74 | CF₃ | Cl | F | OCH₃ | O(oxetan-3-yl) | O | 469.9 | 1.259 |

The compounds listed below in table 3 can be prepared similarly to the examples mentioned above:

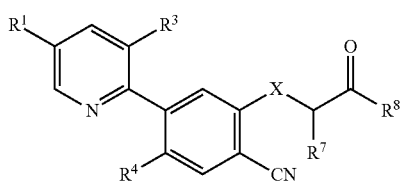

(I), wherein R² is H, R⁵ is CN, R⁶ is H and Y is O

TABLE 3

| Ex | R¹ | R³ | R⁴ | R⁷ | R⁸ | X | m/z | R_t [min] |
|---|---|---|---|---|---|---|---|---|
| 75 | CF₃ | Cl | F | OCH₃ | OCH₃ | O | 418.9 | 1.231 |
| 76 | CF₃ | Cl | F | OCH₃ | OH | O | 404.6 | 1.114 |

B USE EXAMPLES

The herbicidal activity of the phenylpyridines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments were of the following species:

| Bayer code | Scientific name |
|---|---|
| AMARE | *Amaranthus retroflexus* |
| CHEAL | *Chenopodium album* |
| SETVI | *Setaria viridis* |

At an application rate of 16 g/ha, example 6, applied by the post-emergence method, showed very good herbicidal activity against *Amaranthus retroflexus* and *Setaria viridis*, and good herbicidal activity against *Chenopodium album*.

At an application rate of 16 g/ha, examples 1, 2, 3, 4, 7, 8, 10, 11, 12, 13, 14, 15, 16, 17, 18, 19, 20, 21, 22, 23, 24, 25, 26, 27, 28, 29, 30, 31, 32, 33, 34, 35, 36, 38, 39, 40 and 41 applied by the post-emergence method, showed very good herbicidal activity against *Amaranthus retroflexus, Chenopodium album* and *Setaria viridis*.

At an application rate of 16 g/ha, example 44, applied by the post-emergence method, showed very good herbicidal activity against *Amaranthus retroflexus* and *Chenopodium album*, and good herbicidal activity against *Setaria viridis*.

At an application rate of 16 g/ha, examples 43, 45, 46, 47, 48, 49, 50, 56, 57, 59, 60, 61, 62, 63, 64, 65, 66, 67, 68, 72, 73, 74 and 75 applied by the post-emergence method, showed very good herbicidal activity against *Amaranthus retroflexus, Chenopodium album* and *Setaria viridis*.

At an application rate of 16 g/ha, examples 51, 52, 53, 54, 55, 58, 69, 70 and 71 applied by the post-emergence method, showed very good herbicidal activity against *Amaranthus retroflexus* and *Chenopodium album*.

The invention claimed is:
1. A compound of formula (I)

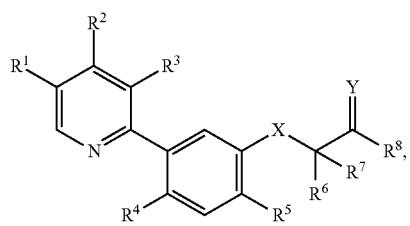

(I)

wherein the variables have the following meanings:
$R^1$ halogen, $C_1$-$C_4$-haloalkyl or $SO_2CH_3$;
$R^2$ H, $CH_3$ or $NH_2$;
$R^3$ halogen;
$R^4$ H or halogen;
$R^5$ halogen or CN;
$R^6$ H or $CH_3$;
$R^7$ $C_1$-$C_6$-alkoxy, $C_1$-$C_6$-haloalkoxy, $C_3$-$C_6$-alkenyloxy, or $C_3$-$C_6$-alkynyloxy;
$R^8$ $OR^9$, $SR^9$, $NR^{10}R^{11}$, $NR^9S(O)R^{10}$, $NR^9S(O)_2R^{10}$, $NR^9S(O)NR^{10}R^{11}$, or $NR^9S(O)_2NR^{10}R^{11}$,
wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
—N=$CR^{12}R^{13}$, wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6-membered heteroaryl,
wherein each phenyl or heteroaryl ring can be substituted by one to four substituents selected from $R^{14}$ or a 3- to 7-membered carbocycle, which carbocycle optionally has in addition to carbon atoms one or two ring members selected from the group consisting of —N($R^{12}$)—, —N=N—, —C(=O)—, —O— and —S—, and
which carbocycle is optionally substituted with one to four substituents selected from $R^{14}$;
wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxy-carbonyl;
$R^{10}$, $R^{11}$ independently of one another are $R^9$, or together form a 3- to 7-membered carbocycle,
which carbocycle optionally has in addition to carbon atoms one or two ring members selected from the group consisting of —N($R^{12}$)—, —N=N—, —C(=O)—, —O— and —S—, and
which carbocycle is optionally substituted with one to four substituents selected from $R^{14}$;
X O or S; and
Y O or S;
or an agriculturally acceptable salt thereof.
2. The compound of claim 1, wherein $R^1$ is $C_1$-$C_4$-haloalkyl.
3. The compound of claim 1, wherein $R^2$ is H.
4. The compound of claim 1, wherein $R^3$ is F, Cl or Br.
5. The compound of claim 1, wherein $R^6$ is H.
6. The compound of claim 1, wherein $R^7$ is $C_1$-$C_6$-alkoxy or $C_1$-$C_6$-haloalkoxy.
7. The compound of claim 1, wherein $R^8$ is $OR^9$ or $NR^9S(O)_2R^9$.
8. The compound of claim 1, which corresponds to the formula (I.a)

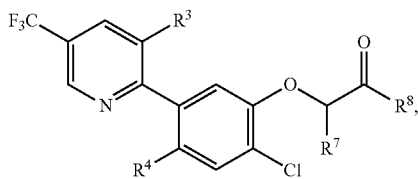

wherein $R^3$, $R^4$, $R^7$ and $R^8$ are as defined in claim 1.

9. A process for the preparation of the compound of claim 1, wherein an acid chloride (II)

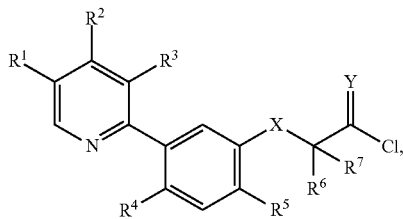

is reacted with a compound (III)

$$H—R^8 \quad (III),$$

in the presence of a base, wherein $R^1$, $R^2$, $R^3$, $R^4$, $R^5$, $R^6$, $R^7$ and $R^8$ are as defined in claim 1.

10. A herbicidal composition comprising an herbicidally active amount of at least one phenylpyridine of formula (I) as claimed in claim 1 and at least one inert liquid and/or solid carrier and, if appropriate, at least one surface-active substance.

11. A process for the preparation of herbicidal active compositions, which comprises mixing an herbicidally active amount of at least one phenylpyridine of formula (I) as claimed in claim 1 and at least one inert liquid and/or solid carrier and, if desired, at least one surface-active substance.

12. A method of controlling undesired vegetation, which comprises allowing an herbicidally active amount of at least one compound of claim 1 to act on plants, their environment or on seed.

13. The method of claim 12, wherein $R^1$ is $C_1$-$C_4$-haloalkyl.

14. The method of claim 12, wherein $R^2$ is H.

15. The method of claim 12, wherein $R^3$ is F Cl or Br.

16. The method of claim 12, wherein $R^6$ is H.

17. The method of claim 12, wherein $R^7$ is $C_1$-$C_6$-alkoxy or $C_1$-$C_6$-haloalkoxy.

18. The method of claim 12, wherein $R^8$ is $OR^9$ or $NR^9S(O)_2R^9$.

19. Acid chlorides of formula (II)

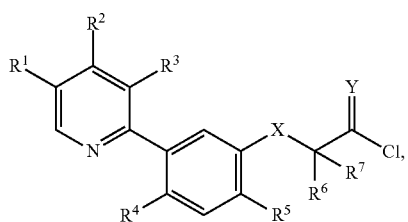

wherein the variables have the following meanings:
$R^1$ halogen, $C_1$-$C_4$-haloalkyl or $SO_2CH_3$;
$R^2$ H, $CH_3$ or $NH_2$;
$R^3$ halogen;
$R^4$ H or halogen;
$R^5$ halogen or CN;
$R^6$ H or $CH_3$;
$R^7$ $C_1$-$C_6$-alkoxy, $C_1$-$C_6$-haloalkoxy, $C_3$-$C_6$-alkenyloxy, or $C_3$-$C_6$-alkynyloxy;
X O or S; and
Y O or S.

* * * * *